US011750555B2

(12) United States Patent
Gaon

(10) Patent No.: US 11,750,555 B2
(45) Date of Patent: Sep. 5, 2023

(54) SYSTEMS AND METHODS FOR USER MATCHING

(71) Applicant: WISDO LTD., Ramat-Gan (IL)

(72) Inventor: Boaz Gaon, Ramat-Gan (IL)

(73) Assignee: WISDO LTD., Ramat-Gan (IL)

( * ) Notice: Subject to any disclaimer, the term of this patent is extended or adjusted under 35 U.S.C. 154(b) by 469 days.

(21) Appl. No.: 16/760,620

(22) PCT Filed: Oct. 29, 2018

(86) PCT No.: PCT/IL2018/051154
§ 371 (c)(1),
(2) Date: Apr. 30, 2020

(87) PCT Pub. No.: WO2019/087182
PCT Pub. Date: May 9, 2019

(65) Prior Publication Data
US 2020/0351234 A1   Nov. 5, 2020

Related U.S. Application Data

(60) Provisional application No. 62/579,027, filed on Oct. 30, 2017, provisional application No. 62/579,780, filed on Oct. 31, 2017.

(51) Int. Cl.
*G06F 15/16* (2006.01)
*H04L 51/52* (2022.01)
(Continued)

(52) U.S. Cl.
CPC .......... *H04L 51/52* (2022.05); *G06F 16/9535* (2019.01); *G06F 16/9536* (2019.01);
(Continued)

(58) Field of Classification Search
CPC . H04L 51/52; G06F 16/9535; G06F 16/9536; G06N 3/04; G06Q 50/01; G16H 10/60; G16H 80/00
See application file for complete search history.

(56) References Cited

U.S. PATENT DOCUMENTS

| 9,720,707 | B1 * | 8/2017 | Shook | G06F 9/451 |
| 2014/0280553 | A1 * | 9/2014 | Hernandez | H04W 4/023 709/204 |
| 2017/0024656 | A1 * | 1/2017 | Gilon | G16H 10/20 |

FOREIGN PATENT DOCUMENTS

WO    WO 2012/071354    5/2012

OTHER PUBLICATIONS

International Search Report for PCT Application No. PCT/IL2018/051154, dated Jan. 31, 2019.

* cited by examiner

*Primary Examiner* — Wing F Chan
*Assistant Examiner* — Joseph R Maniwang
(74) *Attorney, Agent, or Firm* — PEARL COHEN ZEDEK LATZER BARATZ LLP

(57) ABSTRACT

Systems and methods are provided herein for matching between a plurality of users. A computer-implemented method for matching between a plurality of users may be provided. The method may include receiving input data from a plurality of devices associated with the plurality of users, analyzing the input data to determine, for each user and life event, which step(s) on a timeline of the life event that each user (a) has experienced, (b) is currently experiencing, or (c) likely to experience in the future; and matching the plurality of users with one another.

17 Claims, 32 Drawing Sheets

(51) Int. Cl.
  G06F 16/9535 (2019.01)
  G06F 16/9536 (2019.01)
  G06N 3/04 (2023.01)
  G06Q 50/00 (2012.01)
  *G16H 10/60* (2018.01)
  *G16H 80/00* (2018.01)
(52) U.S. Cl.
  CPC ............... G06N 3/04 (2013.01); G06Q 50/01 (2013.01); *G16H 10/60* (2018.01); *G16H 80/00* (2018.01)

| | SV | | SL | | DL | | DV | | Other |
|---|---|---|---|---|---|---|---|---|---|
| | Ask | Answer | Ask | Answer | Ask | Answer | Ask | Answer | Greetings, Comments, Statements, General Replies |
| Breast Cancer Group Chat | 9 | 51 | 7 | 42 | 2 | 18 | 0 | 0 | 131 |

FIG. 17B

| Persona | Anger | Disgust | Fear | Happiness | Sadness | Surprise |
|---|---|---|---|---|---|---|
| Pam "The Sick and Anxious" | ✓ | ✓ | ✓ | | | |
| Emily "The Lonely Intelligent Millennial" | ✓ | ✓ | | | ✓ | |
| Alexis "The Optimist Introvert" | ✓ | | | ✓ | ✓ | |
| Kristin "The Explorer" | ✓ | | ✓ | ✓ | | ✓ |
| Michelle "The Comfortable in Her Own Skin" | | ✓ | ✓ | ✓ | | |
| Maria "The Inexperienced" | | | | | | ✓ |
| Anika "The Been There, Done That" | | | | | | ✓ |

FIG. 19

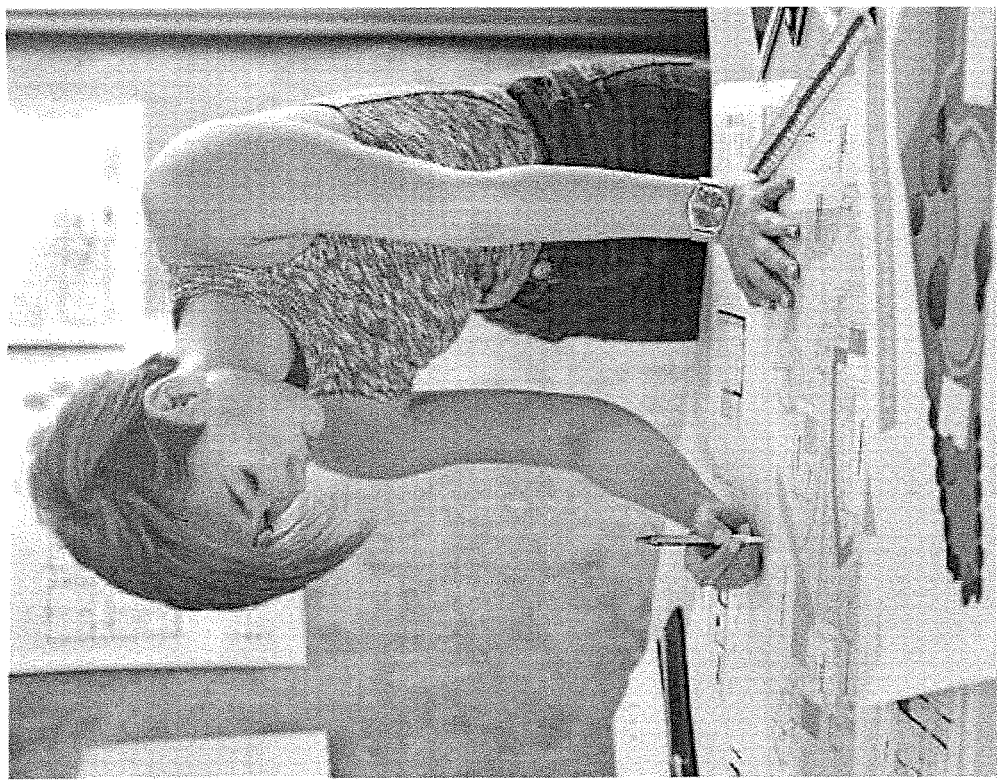

FIG. 20A

Persona sensitive notification cycle – Kirsten

Notification Cycle

Kristin will respond best to Notifications that feed her underlying intent and mirror her emotional state.

| Emotion | Notification | Effect | Frequency |
|---|---|---|---|
| Surprise | "Did you know .....?" | Triggers surprise with user and engages them to take whatever suggested next step is (reopen app to use product) | 1x / day |
| Sadness | New Match<br>New Match Group<br>New Connection<br>New Member in Group<br>Reaction | Triggers sadness with user as they empathize with the new match/group/connection and what they're going through. This will build guilt if the user ignores the notification and should help them return for a new use. | 1x/day |
| Fear | New Message<br>New Match<br>New Match Group<br>New Connection<br>New Member Group<br>Reaction<br>Something New<br>New Share | Triggers the user to feel FOMO (fear of missing out) | Instantly |
| Anger | Reaction<br>New Message<br>New Share<br>Something new in conversation | Triggers the user to engage out of anger and react to the notification trigger. User will return to the product for another use and will continue to check to ensure that the thing they reacted to doesn't make them angry again. | Instantly |

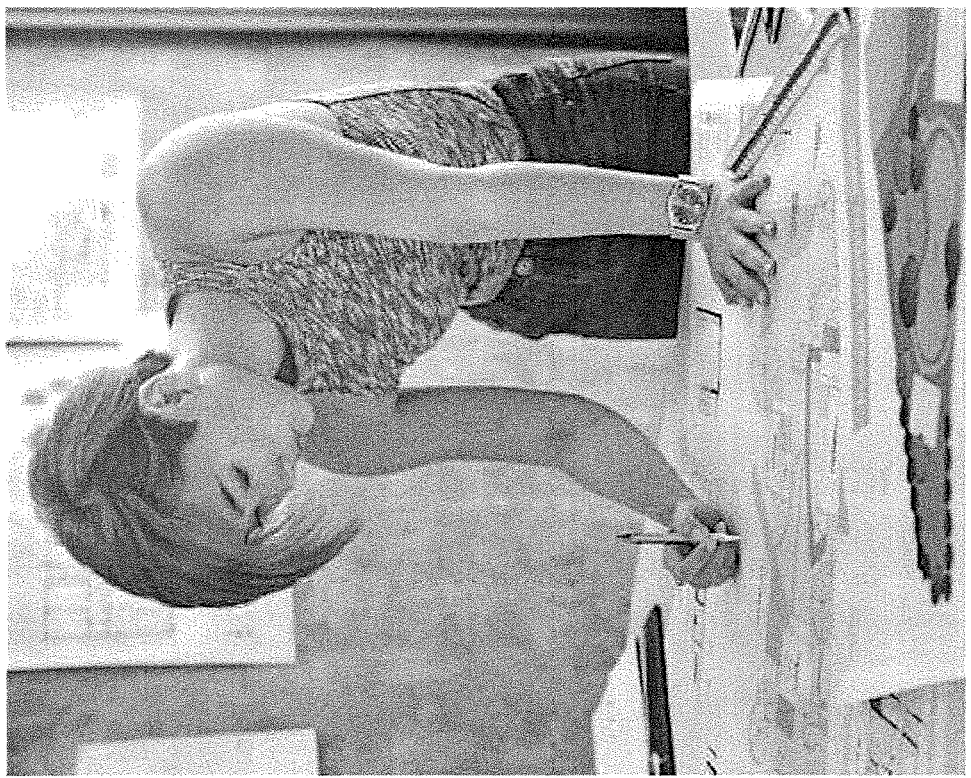

Persona sensitive notification cycle – Kirsten

Prompt Cycle

Kristin will respond best to Prompts that model the following behaviours:

| Habit | Prompt | Effect | Frequency |
|---|---|---|---|
| Surprise | "Did you know ....?" | Triggers surprise with user and engages them to take whatever suggested next step is. | 1 per session upon login |
| Sadness | Unanswered Question<br>Reaction<br>Comment/Post<br>Message | Prompt will trigger user to take action based upon guilt of other being in a state of sadness or need. | Instantly |
| Fear | "Something just occurred..."<br>"Did you know?" | Prompt triggers a user to be afraid of missing out on a new connection, message, reaction or conversation that relates to the topical areas that she's engaged in. | Instantly |
| Anger | Reaction<br>New Message<br>New Share<br>Something new in conversation | Let the user know what has happened and prompt them to take action based upon what has occurred. | Instantly |

FIG. 20B

| Top Mutual Journey | N Worst conv. | N Top conv. | % top conversations |
|---|---|---|---|
| Heartbreak | 24 | 38 | 61% |
| Get Motivated | 20 | 30 | 60% |
| Anxiety | 110 | 122 | 53% |
| Coping with Depressio | 256 | 265 | 51% |
| Sexual Assault | 17 | 17 | 50% |
| LGBTQ+ | 43 | 40 | 48% |
| Relationship Advice | 119 | 109 | 48% |
| Body Positive | 34 | 23 | 40% |

FIG. 24

SYSTEMS AND METHODS FOR USER MATCHING

CROSS-REFERENCE

This application is a national phase application of International Application PCT/IL2018/051154, filed on Oct. 29, 2018 which claims the benefit of U.S. Provisional Application No. 62/579,027 filed on Oct. 30, 2017 and U.S. Provisional Application No. 62/579,780 filed on Oct. 31, 2017, which applications are incorporated herein by reference in their entirety.

BACKGROUND

When people experience a significant life transition (SLT) or life event, they often turn to one or more of the following sources of information: (1) search engines, (2) social networks, (3) paid professionals, (4) friends and family, (5) content/media, and/or (6) support groups.

This has some shortcomings. For example, none of the information sources above may be capable of providing proactive guidance to people undergoing SLTs. The information obtained through those information sources may not be personalized. In many instances, a substantial part of the information may not even be relevant or applicable to a person. Furthermore, the practical wisdom of knowledgeable individuals may not be easily accessible/available to those in need because it is typically embedded within a plethora of other irrelevant information. In addition, the existing information sources may not be capable of proactively providing people with answers to questions that even they themselves do not know to ask. Nor are the existing information sources capable of generating a map of milestones for the life event on a timeline that is relevant and highly personalized to each person. Thus, existing software solutions may not be personalized to match the person's needs. Although paid professionals can provide professional advice (e.g., legal advice or medical advice), they are often unable to address the non-professional aspects (e.g., emotional well-being of the person) during the SLTs.

Additionally, when faced with new life events, people may often feel lost since they may not know whom they can rely upon for advice regarding the new life events. Traditional searches lack a step by step structure and cannot anticipate what and whom people should know. Despite an abundance of online "friends," people still struggle to find trustworthy people who have the same or similar sets of experiences. When people experience a life event, they may often want to connect with other users, who have either experienced, are currently experiencing, or are about to experience the same or similar steps, to assist one another in navigating the life event.

Thus, there is a need for systems and methods that can capture valuable community wisdom, connect users with other users to assist one another in navigating different life events, and inform users on what they need to know, when they need to know certain information, thus helping them improve management of significant life transitions (or events) in a step-wise fashion.

SUMMARY

In some instances, a user may be faced with an event such as a significant life transition ("SLT"). During those moments, the user may lack the experience and tools to make informed decisions at an appropriate time, in a quick and efficient manner.

Accordingly, a need exists to identify a life event based on input from the user, and to determine a plurality of milestones or steps associated with the event. Another need exists to provide personalized insights to the user to address each milestone or step. A further need exists to connect users with other users, who have either experienced, are currently experiencing, or are about to experience the same milestones or steps, to assist one another in navigating the life event. A further need exists to help people take on life's experiences by relying on the wisdom of people who have been there (i.e. undergone those experiences). A further need exists to provide a platform that provides guidance to users for a variety of life events, anticipating what and whom people should know, every step of the way.

To achieve this, people's lives experiences may be crowdsourced into timelines and steps, users may be mapped to their respective steps on different timelines, and people may be matched with what and whom they should know and when they need to know certain information. To create a guide for life, people may yearn for an experienced and available person to connect to. The person can be someone one just like the user, someone who knows the road ahead, someone who cares about what the user has been through, someone who can connect the user to those others whom they know, someone the user wants to spend time with, and/or someone the user wants to talk to in order to seek advice on certain life events. The connections can be created through videos. The connections can also be created by recruiting community leaders, evangelists, and endorsements. The connections can rise above social noise, with impactful videos. The crowdsourcing cycle may be a scalable, cross-vertical cycle which can convert consumers to editors following the classic crowdsourcing model, wherein consumers may constitute 80%, contributors may constitute 18%, and editors may constitute 2% of the user base. Such cycle may generate the supply and demand for timely experienced-based wisdom. In each cycle, the timeline may be 100%, the chat of insight consumer may be 40%, the chat of insight creator may be 20%, and the insightful contributions saved may be 6%. In each cycle, there may be guides and editors, and timelines moderated community measured for "helpfulness." Seeker and sharers of wisdom may create a community that is safer and more rewarding than other online communities.

The different life journeys or events that users may crowdsource may comprise mental illness, breast cancer, marriage, in vitro fertilization ("IVF"), autism, wellness, deaf and hard of hearing ("HOH"), chronic pain, lesbian, gay, bisexual, transgender and queer ("LGBTQ"), parenting, adoption, relocation, retirement, college, finding a dream job, among others. For adoption of a child, the various steps of the life journey may comprise telling existing children that they are about to have siblings, raising funds for adoption, waiting for the call, locating a child independently, managing stress and anxiety, and meeting the birth parents. For deafness or HOH, the various steps may comprise experiencing sudden hearing loss, receiving a name sign, accepting a name sign, accepting a "no known cause" diagnosis, reading body language, managing stress and anxiety, and meeting the birth parents. For bipolar disorder, the various steps may comprise behaving recklessly, denying something is wrong, grieving loss of manic episodes, enjoying remissions, relationship loss, and coping with the feeling of injustice of the condition.

According to some embodiments of the disclosure, a computer-implemented method for matching between a plurality of users is provided.

In an aspect, a computer-implemented method for matching between a plurality of users comprises: receiving input data from a plurality of devices associated with the plurality of users, wherein the input data comprises queries, comments or insights from different users relating to the one or more life events, wherein each life event comprises a plurality of different steps on a timeline; analyzing the input data to determine, for each user and life event, which step(s) on the timeline that each user (a) has experienced, (b) is currently experiencing, or (c) likely to experience in the future; and matching the plurality of users with one another, based on the life events and the steps that the users have experienced, are currently experiencing, or likely to experience in the future, in order to assist each user in navigating the one or more life events.

In some embodiments, receiving the input data comprises crowdsourcing the input data from the users and information from a plurality of external sources. In some embodiments, matching the plurality of users with one another comprises comparing the users to one another based on the steps on the individual timeline of each user. In some embodiments, matching the plurality of users with one another comprises matching (i) a first user who is likely to experience a selected step on the timeline in the future with (ii) a second user who has already experienced the selected step, or matching the second user with the first user.

In some embodiments, the method further comprises, after the first and second users are matched with one another: (1) providing a recommendation to the first user to connect with the second user and obtain insights about the selected step from the second user; and/or (2) providing a recommendation to the second user to connect with the first user to share insights about the selected step with the first user.

In some embodiments, matching the plurality of users with one another comprises matching (i) a first user who had already experienced a selected step on the timeline for a life event with (ii) a second user who had also already experienced the selected step.

In some embodiments, the method further comprises, after the first and second users are matched with one another: providing a recommendation to the first and second users to connect with one another to share their personal experiences about the selected step.

In some embodiments, matching the plurality of users with one another comprises matching (i) a first user who is likely to experience a selected step on the timeline for a life event with (ii) a second user who is also likely to experience the selected step.

In some embodiments, the method further comprises, after the first and second users are matched with one another: providing a recommendation to the first and second users to connect with one another regarding the selected step. In some embodiments, the method further comprises: providing an electronic interface or platform for enabling the first and second users to connect with one another, after the first and second users are matched with one another.

In some embodiments, the recommendation to the first user is provided on a graphical display of a first device associated with the first user, and the recommendation to the second user is provided on a graphical display of a second device associated with the second user. In some embodiments, the recommendations are provided to the first and second users at substantially the same time. In some embodiments, the recommendations are provided to the first and second users at different time instances.

In some embodiments, the method further comprises: enabling the first and second users to communicate with one another via the electronic interface or platform, after the first and second users are connected with one another. In some embodiments, the electronic interface or platform is configured to enable to the first and second users to communicate with one another substantially in real-time. In some embodiments, the method further comprises: monitoring a duration, level, or frequency of communications between the first and second users after they are connected with one another.

In some embodiments, the electronic interface or platform is configured to allow the first and second users to connect by adding each other as a new contact. In some embodiments, the electronic interface or platform is configured to allow the first and second users to share comments, insights or experiences about the selected step with one another. In some embodiments, the electronic interface or platform is configured to allow the first and second users to add additional comments, insights or experiences about the selected step or other steps on the timeline for the life event. In some embodiments, the electronic interface or platform is configured to allow the first user to view the second user's experiences relating to the selected event, if the second user has already experienced the selected event. In some embodiments, the electronic interface or platform is configured to allow the first and second users to view each other's experiences relating to the selected event, if both the first and second users have already experienced the selected event. In some embodiments, the electronic interface or platform is configured to allow the first user to view the second user's timeline and steps, and/or the second user to view the first user's timeline and steps.

In some embodiments, the electronic interface or platform is configured to allow the first user to view changes to the second user's timeline as the second user undergoes the life event, or allow the second user to view changes to the first user's timeline as the first user undergoes the life event. In some embodiments, the electronic interface or platform is configured to allow the first and second user to view changes to each other's timeline as the first and second users respectively undergo the life event.

In some embodiments, the recommendation to the first user comprises a first suggested conversation starter to connect with the second user, and the recommendation to the second user comprises a second suggested conversation starter to connect with the first user. In some embodiments, the first suggested conversation starter is personalized for the first user, and the second suggested conversation starter is personalized for the second user. In some embodiments, the first suggested conversation starter is different from the second suggested conversation starter. In some embodiments, the first and second suggested conversation starters are the same.

In some embodiments, the method further comprises: (1) matching the second user with a first group of users who are likely to experience the selected step, and (2) matching the first user with a second group of users who have already experienced the selected step. In some embodiments, the method further comprises: matching the first and second users with a group of users who have already experienced the selected step. In some embodiments, the method further comprises: matching the first and second users with a group of users who are likely to experience the selected step. In some embodiments, the method further comprises: providing an electronic interface or platform configured to allow (1) the first user to connect with one or more users from the second group, and/or (2) the second user to connect with one or more users from the first group.

In some embodiments, the method further comprises: providing an electronic interface or platform configured to allow the first and second users to connect with one or more users from the group of users. In some embodiments, the method further comprises: (1) providing information about the second group of users on a graphical display of a first device associated with the first user, and/or (2) providing information about the first group of users on a graphical display of a second device associated with the second user. In some embodiments, the method further comprises: providing information about the group of users on a graphical display of a device associated with each of the first and second users.

In some embodiments, matching the plurality of users with one another comprises, for each life event: generating, for a first user, a plurality of scores relative to a second user, wherein the first and second users are undergoing the same life event; and using the plurality of scores to determine a level of match of the second user to the first user.

In some embodiments, the method further comprises: determining whether to provide a recommendation of the second user to the first user based on the level of match. In some embodiments, the method further comprises: providing the recommendation to the first user when the level of match is equal to or above a threshold. In some embodiments, the recommendation is not provided to the first user when the level of match is below a threshold.

In some embodiments, the second user is not a current friend or contact of the first user. In some embodiments, the second user is new to the first user. In some embodiments, the first user comprises one or more users, and the second user comprises one or more users.

In some embodiments, the plurality of scores comprises a first score based on (i) a first set of steps experienced by the first user and (ii) a second set of steps experienced by the second user. In some embodiments, the first score is calculated based on a percentage of (a) a number of common steps between the first and second sets of steps over (b) a number of steps in the first set for the first user.

In some embodiments, the plurality of scores comprises a second score based on (i) a first set of steps experienced by the first user and (ii) a second set of steps that the second user is following and likely to experience. In some embodiments, the second score is calculated based on a percentage of (a) a number of common steps between the first and second sets of steps over (b) a number of steps in the first set for the first user. In some embodiments, the plurality of scores comprises a third score based on (i) a first set of steps that the first user is following and likely to experience and (ii) a second set of steps that are experienced by the second user. In some embodiments, the third score is calculated based on a percentage of (a) a number of common steps between the first and second sets of steps over (b) a number of steps in the first set for the first user.

In some embodiments, the plurality of scores comprises a fourth score that is based on (i) first set of steps that the first user is following and likely to experience and (ii) a second set of steps that the second user is following and likely to experience. In some embodiments, the fourth score is calculated based on a percentage of (a) a number of common steps between the first and second sets of steps over (b) a number of steps in the first set for the first user. In some embodiments, the first score, second score, third score, and fourth score are calculated using in part a parameter that imposes a penalty on score(s) that have lower absolute numbers of common steps. In some embodiments, the parameter is used to enhance score(s) that have higher absolute numbers of common steps.

In some embodiments, the method further comprises: transforming the first score, second score, third score, and fourth score respectively into a first metric, a second metric, a third metric, and a fourth metric that are normalized with respect to one another. In some embodiments, the transformation of the scores into the metrics allows score biases to be reduced.

In some embodiments, the method further comprises: comparing two or more the first, second, third, and fourth metrics to determine the level of match of the second user to the first user. In some embodiments, the method further comprises: comparing only the first, second, and third metrics to determine the level of match of the second user to the first user. In some embodiments, the method further comprises: comparing all of the first, second, third, and fourth metrics to determine the level of match of the second user to the first user.

In some embodiments, the method further comprises: comparing values of two or more of the first, second, third, and fourth metrics; and using the metric with the highest value to determine the level of match of the second user to the first user. In some embodiments, the plurality of scores are generated or updated substantially in real-time as the first user and/or the second user are experiencing different steps in the life event. In some embodiments, the level of match is determined or updated substantially in real-time as the first user and/or the second user are experiencing different steps in the life event.

In an aspect, a computer-implemented system for matching between a plurality of users comprises: a server in communication with a plurality of devices associated with the plurality of users; and a memory storing instructions that, when executed by the server, cause the server to perform operations comprising: receiving input data from the plurality of devices, wherein the input data comprises queries, comments or insights from different users relating to the one or more life events, wherein each life event comprises a plurality of different steps on a timeline; analyzing the input data to determine, for each user and life event, which steps on the timeline that each user (a) has experienced, (b) is currently experiencing, or (c) likely to experience in the future; and matching the plurality of users with one another, based on the life events and the steps that the users have experienced, are currently experiencing, or likely to experience in the future, in order to assist the users in navigating one or more life events.

In an aspect, a non-transitory computer-readable storage medium includes instructions that, when executed by a server, cause the server to perform operations comprising: receiving input data from the plurality of devices, wherein the input data comprises queries, comments or insights from different users relating to the one or more life events, wherein each life event comprises a plurality of different steps on a timeline; analyzing the input data to determine, for each user and life event, which steps on the timeline that each user (a) has experienced, (b) is currently experiencing, or (c) likely to experience in the future; and matching the plurality of users with one another, based on the life events and the steps that the users have experienced, are currently experiencing, or likely to experience in the future, in order to assist the users in navigating one or more life events.

It shall be understood that different aspects of the invention can be appreciated individually, collectively, or in combination with each other. Various aspects of the invention described herein may be applied to any of the particular applications set forth below or for any other types of energy monitoring systems and methods.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 17B shows an example of conversation coded by type;

FIG. 19 shows an example of emotional states of the users;

FIG. 20A shows an example of persona sensitive notification cycle for Kirsten;

FIG. 20B shows the same example of persona sensitive notification cycle for Kirsten;

FIG. 23A illustrates for a plurality of users is match success of a match between a second user and a first user (Y) as a function of the average number of threads the second user replied to;

FIG. 23B illustrates for a plurality of users the match success of a match between a second user and a first user (Y) as a function of the total number of threads the second user started;

FIG. 23C illustrates for a plurality of users the match success of a match between a second user and a first user involving each user (Y) as a function of the average number of threads the user started;

FIG. 24 illustrates data representing importance of users sharing particular top journeys match success of a match between a second user and a first user;

DETAILED DESCRIPTION

Figure 1:
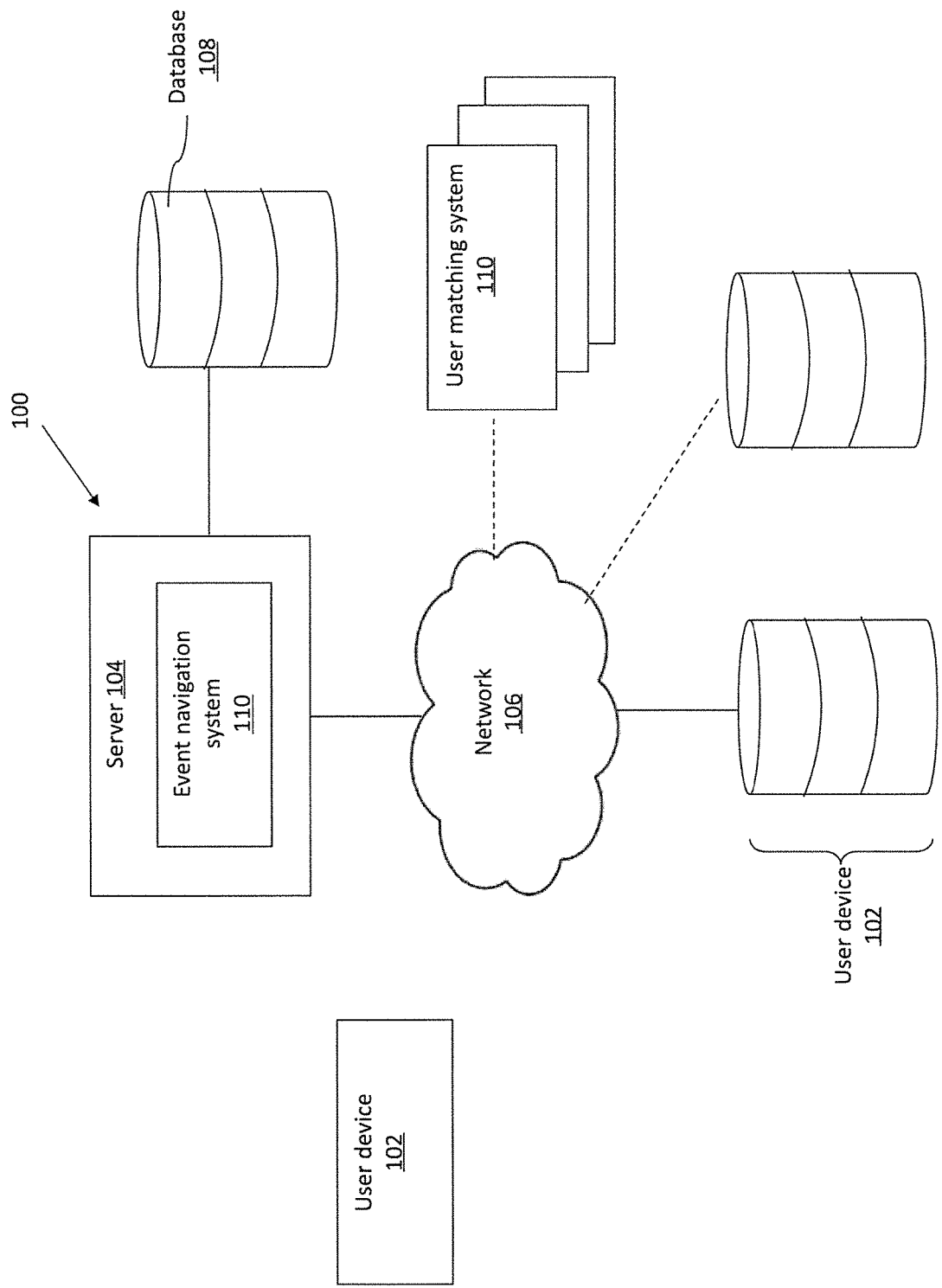
FIG. 1 illustrates an exemplary network layout, in accordance with some embodiments.

Reference will now be made in detail to some exemplary embodiments of the invention, examples of which are illustrated in the accompanying drawings. Wherever possible, the same reference numbers will be used throughout the drawings and disclosure to refer to the same or like parts.

Introduction

In life, people may experience a variety of significant life transitions (SLTs) or life events. SLTs can occur in series or in parallel. They can occur as a consequence of a previous or simultaneous SLT. SLTs may be characterized as, or result in, a journey in an individual's life. Such journey can be long or short. They can be simple or complex. A journey can include one or multiple milestones, steps, or phases. A milestone as described herein may be referred to interchangeably as a step. A SLT as described herein may be referred to interchangeably as a life event or a life journey. A SLT can result in other SLTs or journeys (e.g., loss of a partner can lead to depression or other mental illness). Non-limiting examples of SLTs may include starting and/or attending college, starting a new career, getting married, having children, starting a business, getting divorced, retirement, relocation, or being diagnosed with a serious/chronic illness.

When an SLT occurs, one generally lacks the required experience to make the best decisions, at the right time, quickly and efficiently. Indeed, when one searches the Internet for information to help one make the right decisions, one may find the information available to be unstructured, not personalized, not fitting to the specific problem or issue at hand, and/or nor available in a timely manner. Additionally, it may be difficult for one to find and connect with other users who have either experienced, are currently experiencing, or are about to experience the same or similar steps in a life event, to share experiences and/or learn from one another.

The present disclosure can address at least the above problems, by providing a user matching platform that can match between a plurality of users and make collective community (crowdsourced) wisdom accessible to a user in need of such advice. The term "user" or "end user" as used herein may refer to individuals who are about to go through, are currently going through, an event such as a significant life transition. These are individuals who may generally need help with navigating the life event. Wisdom as used herein may refer to time-sensitive, location-dependent, and content appropriate advice on what a person should know regarding a life event and/or any of its milestones or steps. Wisdom may include insights and advice from other people who have experienced or are currently experiencing the same or similar steps in the life event. In particular, the system and method disclosed herein can connect a user with other users and provide users with information they need to know, when they need to know it, as the users go through different milestones or steps of a life event. Accordingly, the system and methods disclosed herein can help users to make informed decisions, and help them to optimally navigate through the life events by allowing them to sharing their needs, questions, comments, and insights with other uses, and obtain insights from other users who are at different milestones during the same life journey.

User Matching Platforms

In an aspect, a user matching platform is provided. The platform may be configured to perform a computer-implemented method for matching between a plurality of users. The method may comprise receiving input data from a plurality of devices associated with the plurality of users. The input data may comprise queries, comments or insights from different users relating to the one or more life events. Each life event may comprise a plurality of different steps on a timeline. The method may also comprise analyzing the input data to determine, for each user and life event, which step(s) on the timeline that each user (a) has experienced, (b) is currently experiencing, or (c) likely to experience in the future. The method may further comprise matching the plurality of users with one another, based on the life events and the steps that the users have experienced, are currently experiencing, or likely to experience in the future, in order to assist each user in navigating the one or more life events.

The number of the plurality of users may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, 1000000, 100000000, or greater. In other instances, the number of the plurality of users may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, 10, or less.

The plurality of devices may comprise any type of device, for example, but not limited to, consumer electronics, telecommunication devices, or medical equipment. The consumer electronics may comprise TVs, photo equipment and accessories, cameras (video or film), speaker, radio/hi-fi systems, or video projectors. The telecommunication devices may comprise mobile phones, modems, router, phone cards, or telephones. The medical equipment may comprise stethoscope, suction device, thermometer, tongue depressor, transfusion kit, tuning fork, ventilator, watch, stopwatch, weighing scale, crocodile forceps, bedpan, cannula, cardioverter, defibrillator, catheter, dialyzer, electrocardiograph machine, enema equipment, endoscope, gas cylinder, gauze sponge, hypodermic needle, syringe, infection control equipment, an oximeter or oximeters that monitors oxygen levels of the user, instrument sterilizer, kidney dish, measuring tape, medical halogen penlight, nasogastric tube, nebulizer, opthalmoscope, otoscope, oxygen mask and tubes, pipette, dropper, proctoscope, reflex hammer, and sphygmomanometer. The device may be an electronic device. The electronic device may comprise a portable electronic device. The electronic devices may be mobile phones, PCs, tablets, printers, consumer electronics, and appliances. The number of the plurality of devices may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000, or greater. In other instances, the number of the plurality of devices may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, 10, or less.

The input data may comprise queries, comments or insights from different users relating to the one or more life events. The input data may further include data that is directly inputted by the user. In some embodiments, the input data may be a question. Alternatively, the input data may be an online social interaction. In some embodiments, the input data may comprise questions, answers, comments, and/or insights in the form of text, audio, video, and/or photographs that are (1) provided by the plurality of users and (2) associated with the one or more life events. The input data may also be obtained from a social media or a social networking website visited by the plurality of users. In some embodiments, the input data may be analyzed using a natural language processing (NLP) algorithm, as described elsewhere herein. In some embodiments, the input data may further comprise information indicative of the physical locations of the plurality of users. The physical locations of the users are extracted from the input data, as described elsewhere herein. The information indicative of the physical locations of the users may be dynamically updated in real-time as the users move between different places.

The input data may be categorized based on the one or more life events. For instance, the input data may comprise data related to starting and/or attending college, starting a new career, getting married, having children, starting a business, getting divorced, retirement, relocation, or being diagnosed with a serious/chronic illness.

The input data may be stored in a database. A database can be stored in computer readable format. A computer processor may be configured to access the data stored in the computer readable memory. A computer system may be used to analyze the data to obtain a result. The result may be stored remotely or internally on storage medium and communicated to users. The computer system may be operatively coupled with components for transmitting the result. Components for transmitting can include wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples of wireless communication components can include a Wi-Fi receiver, a component for accessing a mobile data standard such as a 3G or 4G LTE data signal, or a Bluetooth receiver. In some embodiments, all data in the storage medium are collected and archived to build a data warehouse. In some embodiments, the database may comprise an external database.

Each life event may comprise a plurality of different steps on a timeline. It should be noted that the term "life events" as used herein may be referred to interchangeably as significant life transitions (SLTs). Similarly, the term "steps" as used herein may be referred to interchangeably as milestones. For instance, if the life event is relocation, the steps may comprise, but are not limited to, finding the desired relocation place, finding a place to live in the relocation place, connecting with friends or family members in the relocation place, selling the current house before relocation, booking the transportation to the relocation place, contacting a moving company, cleaning the current house, arriving at the relocation place. A timeline with different milestones may be generated specific to the user's needs. Each milestone on the user's timeline may include questions and insights addressing those questions. The number of the plurality of different steps may be at least about 1, 5, 10, 15, 20, 25, 30, 35, 40, or greater. In other instances, the number of the plurality of different steps may be at most about 40, 35, 30, 25, 20, 15, 10, 5, or less.

The analyzing process may comprise analyzing the input data to determine, for each user and life event, which step(s) on the timeline that each user (a) has experienced, (b) is currently experiencing, or (c) likely to experience in the future.

The matching may comprise matching the plurality of users with one another, based on the life events and the steps that the users have experienced, are currently experiencing, or likely to experience in the future, in order to assist each user in navigating the one or more life events. The matching may comprise matching users who have experienced certain life events or steps, with one or more other users who have also experienced the same life events. The matching may also comprise matching users who have experienced certain life events or steps, with one or more other users who are currently experiencing the same life events or steps. The matching may also comprise matching users who have experienced certain life events or steps, with one or more users who are likely to experience in the future the same life events or steps. The matching may also comprise matching users who are currently experiencing certain life events or steps, with one or more other users who are currently experiencing the same life events or steps. The matching may also comprise matching users who are currently experiencing certain life events or steps, with one or more other users who are likely to experience in the future the same life events or steps. The matching may also comprise matching users who are likely to experience certain life events or steps in the future, with one or more other users who are likely to experience in the future the same life events or steps. Any matching between different users, who are at the same or different steps of a life event (or multiple life events), may be contemplated in accordance with the embodiments disclosed herein.

Receiving the input data may comprise crowdsourcing the input data from the users and information from a plurality of external sources. The number of the plurality of external sources may be at least about 1, 5, 10, 15, 20, 25, 30, 35, 40, or greater. In other instances, the number of the plurality of external sources may be at most about 40, 35, 30, 25, 20, 15, 10, 5, or less. The external sources may comprise a website channel, email channel, text message channel, Facebook channel, Twilio SMS channel, Skype channel, Slack channel, WeChat channel, Telegram channel, Viber channel, Line channel, Microsoft Team channel, Cisco Spark channel, Amazon Chime channel, among others.

Matching the plurality of users with one another may comprise comparing the users to one another based on the steps on the individual timeline of each user. The comparing may comprise comparing users who have experienced the life events or steps, with one or more other different users who have also experienced the same life events. Additionally or optionally, the comparing may comprise comparing users who have experienced the life events or steps, with one or more different users who are experiencing the same life events or steps. Additionally or optionally, the comparing may comprise comparing users who have experienced the life events or steps, with one or more different users who are likely to experience in the future the same life events or steps. Additionally or optionally, the comparing may comprise comparing users who are currently experiencing the life events or steps, with one or more different users who are experiencing the same life events or steps. Additionally or optionally, the comparing may comprise comparing users who are currently experiencing the life events or steps, with one or more different users who are likely to experience in the future the same life events or steps. Additionally or optionally, the comparing may comprise comparing users who are likely to experience the life events or steps in the future, with one or more different users who are likely to experience in the future the same life events or steps.

The method may further comprise providing an electronic interface or platform for enabling the first and second users to connect with one another, after the first and second users are matched with one another. The electronic interface or platform may comprise graphical user interfaces. The graphical user interfaces (GUIs) may comprise timelines, milestones, and insights/recommendations. Any number of timelines, milestones and insights/recommendations may be contemplated. The GUIs may be rendered on a display screen on a user device. A GUI is a type of interface that allows users to interact with electronic devices through graphical icons and visual indicators such as secondary notation, in addition to text-based interfaces, typed command labels or text navigation. The actions in a GUI are usually performed through direct manipulation of the graphical elements. In addition to computers, GUIs can be found in hand-held devices such as MP3 players, portable media players, gaming devices and smaller household, office and industry equipment. The GUIs may be provided in a software, a software application, a web browser, etc. The GUIs may be displayed on a user device. Examples of such GUIs are illustrated in FIGS. 4 through 11, as described elsewhere herein.

A recommendation to the first user (e.g. for the first user to connect with a second user) may be provided on a graphical display of a first device associated with the first user. Similarly, a recommendation to the second user (e.g.

for the second user to connect with the first user) may be provided on a graphical display of a second device associated with the second user. The recommendations may be provided to the first and second users at substantially the same time. Alternatively, the recommendations may be provided to the first and second users at different time instances.

The method as disclosed herein may further comprise enabling the first and second users to communicate with one another via the electronic interface or platform, after the first and second users are connected with one another. The connection can be connected through wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples of wireless communication components can include a Wi-Fi receiver, a component for accessing a mobile data standard such as a 3G or 4G LTE data signal, or a Bluetooth receiver.

The electronic interface or platform may be configured to enable the first and second users to communicate with one another substantially in real-time.

The method may further comprise monitoring a duration, level, or frequency of communications between the first and second users after they are connected with one another. The duration of communication between the first and second users after they are connected with one another may be at least 1 day, 1 week, 1 month, 1 quarter, 1 year or longer. In some cases, the duration of communication between the first and second users after they are connected with one another may be at most 1 year, 1 quarter, 1 month, 1 week, 1 day or shorter. The level of communication between the first and second users after they are connected with one another may comprise the level of involvement in contribution of answers between the users. The frequency of communication between the first and second users after they are connected with one another may be once per day, once per week, once per month, once per quarter, or once per year.

The electronic interface or platform may be configured to allow the first and second users to connect by adding each other as a new contact. The electronic interface or platform may be a social network. A social network can be a social structure comprising at least one set of social entities (such as, e.g., individuals or organizations). The social network may have a set of dyadic ties or connections (or links) between these entities. Such ties or connections may be complex (e.g., first degree connections, second degree connections, third degree connections, one-to-one relationships, one-to-many relationships, many-to-one relationships, etc.). A social network can include various networks in which a user can interact with other users, such as a social group network, education network, and/or work network. A social network of a user can be characterized by, for example, a contacts list (e.g., address book, email contacts list) or a social media network (e.g., Facebook® friends list, Google+® friends list, LinkedIn® contacts, Twitter® Following list, Line® friends, etc.) of the user. For example, a social network of a user can be a contacts list for a messaging (e.g., chatting, instant messaging, etc.) service. The social networking system may comprise one or more processors and a memory communicatively coupled to the one or more processors to enable one or more online-based social networks between users. For example, for each user of the social networking system, the social networking system may store the user's contacts list and the user's social media network. A user that is a member of a social networking system may have a unique profile with the social networking system. The social networking system may further store and/or track the user's activities on the social networking system.

The electronic interface or platform may be configured to allow the first and second users to share comments, insights or experiences about a selected step with one another. The electronic interface or platform may be configured to allow the first and second users to add additional comments, insights or experiences about the selected step or other steps on the timeline for the life event. For example, a person going through a SLT of having been diagnosed with cancer may wonder how to proceed with treatment. A journey to overcome cancer thus begins. The individual can "ask" the community for advice about cancer treatment. Various members of the community may make comments regarding the cancer treatment. The individual can then select other members for further information or comments. The application or platform disclosed herein can also collect the comments as data and filter out the relevant information. For example, the relevant information may pertain to the specific type and stage of cancer that the person is going through. In addition, the application or platform disclosed herein may collect other relevant information on cancer treatment from reputable sources such as the American Cancer Society.

The electronic interface or platform may be configured to allow the first user to view the second user's experiences relating to the selected event, if the second user has already experienced the selected event. The electronic interface or platform may be configured to allow the first user to view the second user's experiences relating to the selected event, if the second user is currently experiencing the selected event.

The electronic interface or platform may be configured to allow the first and second users to view each other's experiences relating to the selected event, if both the first and second users have already experienced the selected event. The electronic interface or platform may be configured to allow the first and second users to view each other's experiences relating to the selected event, if both the first and second users are currently experiencing the selected event. The electronic interface or platform may be configured to allow the first and second users to view each other's experiences relating to the selected event, if both the first and second users are likely to experience the selected event.

The electronic interface or platform may be configured to allow the first user to view the second user's timeline and steps, and/or the second user to view the first user's timeline and steps. The electronic interface or platform may be configured to allow the first user to view changes to the second user's timeline as the second user undergoes the life event, or allow the second user to view changes to the first user's timeline as the first user undergoes the life event. The electronic interface or platform may be configured to allow the first and second user to view changes to each other's timeline as the first and second users respectively undergo the life event.

The method as disclosed herein may further comprise: (1) matching the second user with a first group of users who are likely to experience the selected step, and (2) matching the first user with a second group of users who have already experienced the selected step. The method may further comprise: (1) matching the second user with a first group of users who are experiencing the selected step, and (2) matching the first user with a second group of users who have already experienced the selected step. The method may further comprise: (1) matching the second user with a first group of users who have experienced the selected step, and (2) matching the first user with a second group of users who have already experienced the selected step.

The method may comprise providing an electronic interface or platform configured to allow (1) the first user to connect with one or more users from the second group, and/or (2) the second user to connect with one or more users from the first group. The method may further comprise (1) providing information about the second group of users on a graphical display of a first device associated with the first user, and/or (2) providing information about the first group of users on a graphical display of a second device associated with the second user. The first group may comprise a plurality of users that have experienced, are currently experiencing, or likely to experience the selected step. The second group may comprise a plurality of users that have experienced, are currently experiencing, or likely to experience the selected step. The user in the first group may be different from the user in the second group.

User Matching Methods Categories

Been-Follow/Follow-Been

In some embodiments, matching the plurality of users with one another may comprise matching (i) a first user who is likely to experience a selected step on the timeline in the future with (ii) a second user who has already experienced the selected step, or matching the second user with the first user. The method may further comprise, after the first and second users are matched with one another: (1) providing a recommendation to the first user to connect with the second user and obtain insights about the selected step from the second user; and/or (2) providing a recommendation to the second user to connect with the first user to share insights about the selected step with the first user.

For instance, a first user may be likely or looking to find a new job as an accountant in a month, and the second user had just found a new job as an accountant two weeks ago. The first user can be matched with the second user through the user matching method so the first user can obtain advice from the second user regarding how to find a job as an accountant.

Been-Been

In some embodiments, matching the plurality of users with one another may comprise matching (i) a first user who had already experienced a selected step on the timeline in the future for a life event with (ii) a second user who had also already experienced the selected step. The method may comprise, after the first and second users are matched with one another: providing a recommendation to the first and second users to connect with one another to share their personal experiences about the selected step.

For instance, both the first user and the second user have already overcome anxiety, and they are matched through the user matching platform. After the matching, the first user and the second user can share experience with each other regarding how they overcame anxiety.

Follow-Follow

In some embodiments, matching the plurality of users with one another may comprise matching (i) a first user who is likely to experience a selected step on the timeline for a life event with (ii) a second user who is also likely to experience the selected step. The method may further comprise, after the first and second users are matched with one another: providing a recommendation to the first and second users to connect with one another regarding the selected step.

For instance, both the first user and the second user are likely to relocate next month, and they are matched through the user matching platform. After the matching, the first user and the second user can share experience with each other regarding the preparation of the relocation.

In some instances, the recommendation to the first user may comprise a first suggested conversation starter to connect with the second user, and the recommendation to the second user may comprise a second suggested conversation starter to connect with the first user. The first suggested conversation starter may be personalized for the first user, and the second suggested conversation starter may be personalized for the second user. The first suggested conversation starter may be different from the second suggested conversation starter. The first and second suggested conversation starters may be the same. The method may further comprise matching the first and second users with a group of users who have already experienced the selected step.

In some embodiments, the method may further comprise: matching the first and second users with a group of users who are likely to experience the selected step. The method may further comprise providing an electronic interface or platform configured to allow the first and second users to connect with one or more users from the group of users. The method may further comprise providing information about the group of users on a graphical display of a device associated with each of the first and second users. The information about the group of users may comprise the number of the users in the group, the geographic locations of the user of the group, the pictures of the users in the group, the hobbies of the users in the group, and the life events each user in the group has been through.

Algorithm

In some embodiments, matching the plurality of users with one another may comprise, for each life event: generating, for a first user, a plurality of scores relative to a second user, wherein the first and second users are undergoing the same life event; and using the plurality of scores to determine a level of match of the second user to the first user.

The method may further comprise: determining whether to provide a recommendation of the second user to the first user based on the level of match. The method may further comprise: providing the recommendation to the first user when the level of match is equal to or above a threshold. The recommendation may not be provided to the first user when the level of match is below a threshold.

The second user may not be a current friend or contact of the first user. The second user may be new to the first user. In some instance, the first user and the second user may be provided in plurality. For example, the first user may comprise one or more users, and the second user may comprise one or more users. The plurality of scores may comprise a first score based on (i) a first set of steps experienced by the first user and (ii) a second set of steps experienced by the second user.

The first score may be calculated based on a percentage of (a) a number of common steps between the first and second sets of steps over (b) a number of steps in the first set for the first user. The plurality of scores may comprise a second score based on (i) a first set of steps experienced by the first user and (ii) a second set of steps that the second user is following and likely to experience. The second score may be calculated based on a percentage of (a) a number of common steps between the first and second sets of steps over (b) a number of steps in the first set for the first user. The plurality of scores may comprise a third score based on (i) a first set of steps that the first user is following and likely to experience and (ii) a second set of steps that are experienced by the second user. The third score may be calculated based on a percentage of (a) a number of common steps between the first and second sets of steps over (b) a number of steps in the first set for the first user. The plurality of scores may comprise a fourth score that is based on (i) first set of steps that the first user is following and likely to experience and (ii) a second set of steps that the second user is following and likely to experience. The fourth score may be calculated based on a percentage of (a) a number of common steps between the first and second sets of steps over (b) a number of steps in the first set for the first user. The first score, second score, third score, and fourth score may be calculated using in part a parameter that imposes a penalty on score(s) that have lower absolute numbers of common steps. The parameter may be used to enhance score(s) that have higher absolute numbers of common steps.

The method may further comprise: transforming the first score, second score, third score, and fourth score respectively into a first metric, a second metric, a third metric, and a fourth metric that are normalized with respect to one another. Statistical techniques may be used for the transformation. The statistical techniques may comprise linear regression, classification, resampling methods, subset selection, shrinkage, dimension reduction, nonlinear models, tree-based methods, support vector machines, and unsupervised learning the transformation of the scores into the metrics may allow score biases to be reduced.

The method may further comprise: comparing two or more of the first, second, third, and fourth metrics to determine the level of match of the second user to the first user. In some cases, the method may comprise: comparing only the first, second, and third metrics to determine the level of match of the second user to the first user. In some cases, the method may comprise: comparing all of the first, second, third, and fourth metrics to determine the level of match of the second user to the first user. In some cases, the method may comprise: comparing values of two or more of the first, second, third, and fourth metrics; and using the metric with the highest value to determine the level of match of the second user to the first user. The plurality of scores may be generated or updated substantially in real-time as the first user and/or the second user are experiencing different steps in the life event. The level of match may be determined or updated substantially in real-time as the first user and/or the second user are experiencing different steps in the life event.

In some embodiments, the method may comprise providing a matching algorithm. The matching algorithm may be optimized for relevancy. A match ranking algorithm may comprise an inventory step, signal step, and prediction step. The inventory step may comprise questions or queries regarding who is available, that the user has not met, and the user has been in steps on a timeline that other users are currently following. The signal step may comprise questions or queries regarding activity level, helpfulness to other users, persona type matching, community feedback, tone and language, and track record. The prediction step may comprise questions or queries regarding likelihood to connect, likelihood of starting a conversation, likelihood of liking/disliking, and likelihood of obtaining help advice. These indicators may be combined into a match relevancy score.

The 1:1 match success may be determined by one or more of the following factors: did the user connect; did they start a 1:1 conversation; first conversation engagement:number of messages, positive tone and language, length of time; interaction frequency; reaction to each other's public contributions; and referral to one another in group chats. The 1:group (i.e. one-to-many) match success for passive listeners may be determined by retention:return frequency; and engagement (e.g., reactions to contributions). The 1:group (i.e. one-to-many) match success for active participants may be determined by first conversation engagement (e.g., number of messages, positive tone and language, length of time); interaction frequency; and level of contribution.

The group chat features may comprise a plurality of details. The plurality of details may comprise: number of users per group, self-provisioning, public and private, moderated and unmoderated, suggested members, group hours, suggested groups, active indicator, group membership, groups by type, matching criteria, light bulb cycle, administrative role and rights, and moderator role and rights.

For number of users per group, the number of users that can be in a group may not be restricted. There may be optimal numbers of users per group. In some cases, there may not be optimal numbers of users per group. When a group grows to a point where it has so many users that the conversation degrades in quality, it may become difficult for users to follow and be overactive. In this situation, the user matching platform can: a) do nothing, and users can start other groups if they want a smaller, more intimate conversation that doesn't have big group issues; or b) intervene and prompt users to suggest that they form a new smaller group; or c) allow users to create private groups that require permission to join. This may cap the number of users allowed and make it easier for groups to minimize issues associated with large groups.

For self-provisioning, users can create their own new group chats. A group may include 3 or more people having a conversation. For public and private, users can select what type of group chat they want to create. For moderated and unmoderated, users can select if they want to have a moderator or not. For suggested members, administrative and moderators can see a list of suggested members who are a match for the group but aren't members. Match may be based upon any of the algorithms disclosed herein. For group hours, a group may be always on asynchronously. A group may also have synchronous capabilities which may change this dynamic. For suggested groups, users can see a list of groups that they're a match for in their "Your Matches." For active indicator, users, admins and moderators can see who is active in a group chat. For group membership, users, admins and moderators can see who is a member of a group chat. For group by type, the group may offer prefab groups for similar/learn ("SL"), similar/validate ("SV"), different/learn ("DL"), and different/validate ("DV"), and prompt to suggest that users join them.

For matching criteria, a user may be a match for a group chat if: 1) they have experienced one or more steps in a life event ("Been Theres") that align with the purpose of the group chat; 2) they are about to experience 1 or more steps in a life event ("Follows") that align with the purpose of the group chat. For light bulb cycle, chat contributions that have >5 (or any number) "Insightful" Light Bulb reactions may be added to a queue of Top Contributions. These Top Contributions may be added manually into the conversation by the admin/moderator when the conversation lags. For administrative role and rights, an administrator may be required for each group chat. The person who creates the group chat may be automatically assigned as the administrator until they relinquish that role and give it to another user. An admin can: have full moderation rights+responsibilities; delete the group chat; and merge the group chat with another group. The Top Contributions may be added to the conversation via Prompts without manual intervention from the admin/moderator. For moderator role and rights, a moderator may not be required for each group chat. The moderator can: add/delete/ban users; flag/delete content; participate in the conversation as a user; inject content into the conversation; invite new users to the conversation; manually add prompts to the conversation; and manually send quality control ("QC") messages 1:1 to each group participant.

The matching may comprise a plurality of details. The plurality of details may comprise matching criteria, training, and placement in product. For matching criteria, a user may be deemed to be a match for another user if: they share at least 1 "Been There"; they share at least 1 "Follow"; they have >3 (or any number) connections in common; they are participating in >2 (or any number) of the same group chats; their intent matches; their intent and quality control responses match; their personas match; they have >3 (or any number) of the same reactions (Insightful or Emotional reactions) within a group chat to the same contributions or content; they have ignored >10 (or any number) of the same suggested matches; they share at least 1 (or any number) "Been There" or "Follow" and they share the same location; they share the same stated Goals. If all other potential matches have been exhausted, then "New to platform" may match of users who have just joined. The new users may be served up in order of newest to oldest. A new member may correspond to a member that just joined within, for example the past 7 days. For training, the matching algorithm may be trained based upon user's responses to the suggested matches. For placement in product, the placement of the suggested matches (users and group chats) in several places in the product may be tested. The user matching platform may track which placements generate the best conversion (of suggestion to new connection) and then optimize the placements per user.

In some embodiments, the method may comprise matching a plurality of users. The matching can be based on where each user is on a timeline, which may include what each of the users either has experienced, is currently experiencing, or is likely to experience in the future. The matching may also be based on the messages or actions from the users.

For example, for a given life-journey and a first user A which participates in this journey, an algorithm (or "matching algorithm") may generate four user matching scores in respect to each other second user B. User A may be the user receiving the recommendation, and user B may be the potential recommendation candidate. These four scores may be based on a similar algorithm, but each captures a different aspect of the user pair-wise interaction. These scores may include (1) Been-Been (BB), (2) Been-Follow (BF), (3) Follow-Been (FB), and (4) Follow-Follow. Each of these scores can be calculated as a raw score or as a normalized score. The raw score calculation can provide a numerical value for each score. The normalized score calculation can normalize the raw scores so that the scores may be compared to each other. Any 1, 2, 3, or 4 of these scores can be used by the method to determine a match between user A and a user B.

In some instances the method may not allow the matching of users who have previously been matched, or users who are friends. In some of these instances, user B may be a friend to user A, user B may be a contact of user A, user B may be a previous friend of user A, or user B may be a previous contact of user A. In some of these cases, the scores based on the data from users A and B need not be calculated.

In some instances, to calculate these scores, the method may use user input metrics from the user input data. These user input metrics may include Been-There and Following. Been-There may be used to indicate that the user has previously experienced a step on a timeline. In contrast, Following may be used to indicate that the user is experiencing, expected to experience, or likely to experience a step on a timeline. Been-There and Following can be provided by the user. Using these metrics, the location of each user on a timeline can be determined. Examples of how to calculate raw scores and normalized scores are provided as follows.

Calculating the Raw Scores

Been-Been (BB) may be a score for a pair of users based on the percent intersection of the Been-There metric between User A and User B. In other words, this may be a score of the relation between user A, may have already experienced a selected step on a timeline, and user B, who may have already experienced the same selected step on a timeline. These shared experiences may influence the final score. This score may be calculated such that more shared experiences may result in a higher score and fewer shared experiences may result in a lower score. Additionally, the total number of Been-There steps, or the size of the Been-There metric, for user A may influence the BB score for user A. Thus, the experiences user A has had may influence the BB score for user A. In some instances, User A having more experiences may result in a higher score and a lower number leads to a lower score.

This score can be calculated as a raw score or a normalized score. The raw score may be the magnitude of the match of user B to user A, and may be normalized to calculate the normalized score, so that scores can be compared.

The raw score may be calculated for every user A as:

$$BB(A, B) = \frac{|\{x | x \in Been(A) \text{ and } x \in Been(B)\}|}{|Been(A)| + AbsCountCoef}$$

In this case, users A with a high BB score for a given user B may have experienced many of the same life-journey steps as user B.

Been-Follow (BF) may be a score for a pair of users based on the percent intersection of the Been-There metric of user A with the Following metric of user B. In other words, this may be a score of the relation between user A, who may have already experienced a selected step on a timeline, and user B, who may be likely to experience the same selected step on a timeline. These aligned experiences may influence the final score. The score may be calculated such that more aligned experiences between user A and user B may result in a higher score, and fewer shared experiences may result in a lower score. Additionally, the total number of Been-There steps, or the size of the Been-There metric, for user A can affect the score such that a higher number leads to a higher score and a lower number leads to a lower score. In some instances, this score may be calculated as a ratio of a number of common steps between the first user A and second user B, to the number of steps experienced by the first user A.

This score can be calculated as a raw score or a normalized score. The raw score may be the magnitude of the match of user B to user A, and may be normalized to calculate the normalized score, so that scores can be compared.

The raw score may be calculated for every user A as:

$$BF(A, B) = \frac{|\{x | x \in Been(A) \text{ and } x \in Follow(B)\}|}{|Been(A)| + AbsCountCoef}$$

In this case, users A with a high BF score for a given user B may have experienced many of the life-journey steps that user B may expect to experience soon.

Follow-Been (FB) may be a score for a pair of users based on the percent intersection of the Following metric of user A with the Been-There metric of user B. In other words, this may be a score of the relation between user A, who may be likely to experience a selected step on a timeline, and user B, who may have already experienced the same selected step on a timeline. This score can be calculated as a raw score or a normalized score, as described above. This score may be calculated such that more aligned experiences between user A and user B may result in a higher score, and fewer shared experiences may result in a lower score. Additionally, the total number of Following steps, or the size of the Following metric, for user A may affect the score such that a higher number leads to a higher score and a lower number leads to a lower score.

This score can be calculated as a raw score or a normalized score. The raw score may be the magnitude of the match of user B to user A, and may be normalized to calculate the normalized score, so that scores can be compared.

The raw score may be calculated for every user A as:

$$FB(A, B) = \frac{|\{x | x \in \text{Follow}(A) \text{ and } x \in \text{Been}(B)\}|}{|\text{Follow}(A)| + AbsCountCoef}$$

In this case, users A with a high FB score for a given user B may expect to experience many of the same life-journey steps that user B recently experienced.

Follow-Follow (FF) may be a score for a pair of users based on the percent intersection of the Following metric of user A with the Following metric of user B. In other words, this may be a score of the relation between user A, who may be likely to experience a selected step on a timeline, and user B, who may be likely to experience the same selected step on a timeline. This score can be calculated as a raw score or a normalized score, as described above. This score may be calculated such that a greater number of experiences which both users A and B may be likely to experience may result in a higher score, and fewer such experiences may result in a lower score. Additionally, the total number of Following steps, or the size of the Following metric, for user A may affect the score such that a higher number leads to a higher score and a lower number leads to a lower score.

This score can be calculated as a raw score or a normalized score. The raw score may be the magnitude of the match of user B to user A, and may be normalized to calculate the normalized score, so that scores can be compared.

The raw score may be calculated for every user A as:

$$FF(A, B) = \frac{|\{x | x \in \text{Follow}(A) \text{ and } x \in \text{Follow}(B)\}|}{|\text{Follow}(A)| + AbsCountCoef}$$

Users A with a high FF score for a given user B may expect to experience many of the same life-journey steps that user B may expect to experience.

In each of the above scores, there may be included in the denominator an "AbsCountCoef" term. This term may be a constant and may be included to penalize scores which can or are based on a low absolute number of shared steps. In some instances, AbsCountCoef may be set equal to 1. In some embodiments, the AbsCountCoef term may not be necessary or not included.

In some instances, the BB, BF, FB, and FF raw scores are transformed to BB, BF, FB, and FF Z-scores, where a Z-score can be a measure of how many standard deviations below or above the population mean a raw score is. The Z-score may be calculated as the ratio of the difference between the raw score and the mean score to the standard deviation of the score, for one of the BB, BF, FB, or FF scores. In this calculation, the mean and standard deviation may be calculated based on data from at least several users. This transformation may make these scores inter-comparable, and can be a method of normalizing the scores, although other methods of normalizing the scores are acceptable.

In some instances, 2, 3, or 4 of the Z-scores may be compared with each other. In these instances, one of the compared scores can indicate the most significant score for determining the user match. In a notable instance, the highest of the compared scores may indicate the most significant interaction type.

As the users experience different steps, the Been-There and Following metrics for those users may change. As such, the measure of the success of the match of one of users B to user A may change over time. Also, over time, different users B can be matched to user A as these metrics change. To account for this, these scores may be updated periodically or substantially in real time as the first user or the second user experiences different steps.

The scores as they are calculated above may not be symmetric in both ways. In other words, the BB score for user A compared with user B may not be equal to the BB score for user B compared with user A. Similarly, the BF score for user A compared with user B may not be equal for the BF score for user B compared with user A. Likewise, the FB score for user A compared with user B may not be equal for the FB score for user B compared with user A. Similarly, the FF score for user A compared with user B may not be equal to the FF score for user B compared with user A.

Overtime, the needs of user A and experiences of user B may change. Thus, use of older data could render the match irrelevant. To prevent this, the algorithm may use only recent data in the calculations of the BB, BF, FB, and FF scores, where recent data can include data collected in the past month, week, day, hour, or subset of these timescales. This application of only recent data may keep the user matching fresh and relevant.

Typically, when calculating the above described scores and providing matches of users A and B, the input data may be assumed to be clean. As a non-limiting example, deleted users are not included in the calculation. This may ensure that the matches provided to user A are useful and relevant.

Each user may be unique and can have a unique combination of life events. Thus, the method may or may not assume for one life event that other life events have occurred for a particular user. Thus, each life event may be considered separately. In other words, the BB, BF, FB, and FF scores can be calculated for one life event for user A independently of other life events that user A has experienced.

In some instances, the user matching may be based on only one of the scores for the pair of users A and B. In these instances, after one or more of the BB, BF, FB, and FF scores are calculated, and the calculated score with the highest value may be used to determine the match.

Calculating the Normalized Scores

In some implementations of the described methods, one or more normalized scores may be calculated. The normalized scores can be thought of as the final scores in some instances. The normalized score may be calculated as described below. In this embodiment, the raw scores are transformed into a z-score like metric to produce the normalized scores.

The normalization of the scores can introduce at least two major benefits. First, it can make the scores inter-comparable. Second, score biases can diminish. For example, if for a pair of users there may be a tendency to have a higher BB score than BF score, this tendency will be eliminated, and the scores will scale the same.

The normalized BB score can be calculated as the ratio of the difference between the raw score and the average of the set of raw scores to the standard deviation of the set of raw scores:

$$BB_{norm} = \frac{BB - P_{BB}}{\sqrt{P_{BB} * (1 - P_{BB}) + eps}}$$

where $$P_{BB} = \frac{\sum_{A \neq B} |\{x \mid x \in \text{Been}(A) \text{ and } x \in \text{Been}(B)\}|}{eps + \sum_{A \neq B} |\{x \in \text{Been}(A) \mid \text{Been}(A) \cap \text{Been}(B) \neq 0\}|}$$

and where $P_{BB}$ may be the average of the BB scores, and eps may be preventing division by zero. In one embodiment, eps has a default value of $10^{-6}$.

The other normalized scores can be similarly calculated as:

$$BF_{norm} = \frac{BF - P_{BF}}{\sqrt{P_{BF} * (1 - P_{BF}) + eps}}$$

$$FB_{norm} = \frac{FB - P_{FB}}{\sqrt{P_{FB} * (1 - P_{FB}) + eps}}$$

and $$FF_{norm} = \frac{FF - P_{FF}}{\sqrt{P_{FF} * (1 - P_{FF}) + eps}}$$

where:

$$P_{BF} = \frac{\sum_{A \neq B} |\{x \mid x \in \text{Been}(A) \text{ and } x \in \text{Follow}(B)\}|}{eps + \sum_{A \neq B} |\{x \in \text{Been}(A) \mid \text{Been}(A) \cap \text{Follow}(B) \neq 0\}|}$$

$$P_{FB} = \frac{\sum_{A \neq B} |\{x \mid x \in \text{Follow}(A) \text{ and } x \in \text{Been}(B)\}|}{eps + \sum_{A \neq B} |\{x \in \text{Follow}(A) \mid \text{Follow}(A) \cap \text{Been}(B) \neq 0\}|}$$

and $$P_{FF} = \frac{\sum_{A \neq B} |\{x \mid x \in \text{Follow}(A) \text{ and } x \in \text{Follow}(B)\}|}{eps + \sum_{A \neq B} |\{x \in \text{Follow}(A) \mid \text{Follow}(A) \cap \text{Follow}(B) \neq 0\}|}$$

To match the users, an algorithm can be implemented wherein one or more of the BB, BF, FB, and FF scores and/or one or more of the BBnorm, BFnorm, FBnorm, and FFnorm scores are calculated, wherein the first and second users are undergoing the same life event; and using the plurality of scores to determine a level of match of the second user to the first user.

The algorithm may further determine whether to provide a recommendation of the second user to the first user based on the level of match. This recommendation would suggest to the first user that they should connect with the second user, for example to gain insight on what to expect while going through the life event. In some implementations of the algorithm, if one or more of the scores may be below a threshold, a recommendation may not be provided. Similarly, in some implementations, if one or more of the scores may be above a threshold, a match may be provided.

In some methods, the match can be updated substantially in real time. This may be implemented to provide accurate and useful matches to users. For example, on Monday, user A may be highly likely to experience event E, while user B just successfully traversed event E. On Monday, user B may be an excellent match for user A, according to the FB score. However, on Wednesday, user A traverses event E. Thus, advice from user B to user A on how to handle event B may no longer be relevant to user A, and they are no longer an ideal match.

There can be several interpretations of "substantially in real time," and the chosen implementation may depend on computing power available, connectivity, input data availability, the pace at which the event or steps typically proceeds, or other factors. This may be updated constantly, every second, every minute, every hour, every day, every week, every month, every year, or other time scale appropriate for the event. Alternatively, matches may be updated based on a triggering event. The triggering event may be an input of the completion of the event from user A, a change in priority from either user, lack of activity for either user, or other reason.

Systems for User Matching

In an aspect, a computer-implemented system for matching between a plurality of users may comprise: a server in communication with a plurality of devices associated with the plurality of users; and a memory storing instructions that, when executed by the server, cause the server to perform operations comprising: receiving input data from the plurality of devices, wherein the input data comprises queries, comments or insights from different users relating to the one or more life events, wherein each life event comprises a plurality of different steps on a timeline; analyzing the input data to determine, for each user and life event, which steps on the timeline that each user (a) has experienced, (b) is currently experiencing, or (c) likely to experience in the future; and matching the plurality of users with one another, based on the life events and the steps that the users have experienced, are currently experiencing, or likely to experience in the future, in order to assist the users in navigating one or more life events.

The system may comprise a matching engine. The matching engine may be configured to receive a query from an end user. The user query may be provided to the matching engine using one or more user devices. In some instances, the user query may be provided in plural, and may comprise a plurality of user queries. The user query may include questions, comments, or statements made by one or more users. Different users may provide different queries, and the queries may relate to any subject matter. For example, a user may be going through a significant life transition (SLT), such as going to college, getting married, having children, starting a business, getting divorced, retirement, relocation, or diagnosed with a terminal illness, among others. In those instances, the user query may be indicative of the user's thoughts, feelings, moods, opinions, comments, worries, general questions regarding any of the above-mentioned SLTs, and/or specific questions regarding certain topics or milestones within a SLT. Any type or form of user query may be contemplated. The user query may include text, emoticons, pictures, photographs, videos, audio files, etc. The matching engine may be further configured to match different users by analyzing the queries. When the matching engine finds a match, the matching engine may provide signals to the user regarding the match. The matching engine may also be configured to receive an insight from a contributor. A contributor may be a person who has experience with a SLT, has gone through a SLT, or who is currently going through a SLT. The SLT may include going to college, getting married, having children, starting a business, getting divorced, retirement, relocation, or diagnosed with a terminal illness, among others. The insight may relate to the contributor's personal experience navigating one or more milestones of a SLT.

In some embodiments, end users may add questions about subjects they are interested in. The subjects may relate to SLTs, milestones in the SLTs, events, etc. The matching engine may be configured to receive questions from the end users. The matching engine may employ natural language processing (NLP) and machine learning methods to (1) categorize the questions into different subjects, (2) tag the questions, (3) find similar questions or existing answers to those questions, (4) match questions to other users or contributors who may be able to answer those questions, and/or (5) match different users by analyzing different questions.

In some embodiments, a machine learning methods may utilize one or more neural networks. A neural network may be a type of computational system that can learn the relationships between an input data set and a target data set. A neural network may be a software representation of a human neural system (e.g. cognitive system), intended to capture "learning" and "generalization" abilities as used by a human. A neural network may comprise a series of layers termed "neurons" or "nodes." A neural networks may comprise an input layer, to which data is presented; one or more internal, and/or "hidden," layers; and an output layer. A neuron may be connected to neurons in other layers via connections that have weights, which are parameters that control the strength of a connection. The number of neurons in each layer may be related to the complexity of a problem to be solved. The minimum number of neurons required in a layer may be determined by the problem complexity, and the maximum number may be limited by the ability of a neural network to generalize. Input neurons may receive data being presented and then transmit that data to the first hidden layer through connections' weights, which are modified during training. The node may sum up the products of all pairs of inputs and their associated weights. The weighted sum may be offset with a bias. The output of a node or neuron may be gated using a threshold or activation function. An activation function may be a linear or non-linear function. An activation function may be, for example, a rectified linear unit (ReLU) activation function, a Leaky ReLu activation function, or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

A first hidden layer may process data and transmit its result to the next layer through a second set of weighted connections. Each subsequent layer may "pool" results from previous layers into more complex relationships. Neural networks may be programmed by training them with a known sample set (data collected from one or more sensors) and allowing them to modify themselves during (and after) training so as to provide a desired output such as an output value. A trained algorithm may comprise convolutional neural networks, recurrent neural networks, dilated convolutional neural networks, fully connected neural networks, deep generative models, and Boltzmann machines.

Weighting factors, bias values, and threshold values, or other computational parameters of a neural network, may be "taught" or "learned" in a training phase using one or more sets of training data. For example, parameters may be trained using input data from a training data set and a gradient descent or backward propagation method so that output value(s) that a neural network computes are consistent with examples included in training data set.

The number of nodes used in an input layer of a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of node used in an input layer may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller. In some instance, the total number of layers used in a neural network (including input and output layers) may be at least about 3, 4, 5, 10, 15, 20, or greater. In other instances, the total number of layers may be at most about 20, 15, 10, 5, 4, 3 or less.

In some instances, the total number of learnable or trainable parameters, e.g., weighting factors, biases, or threshold values, used in a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of learnable parameters may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller.

A neural network may comprise a convolutional neural network. A convolutional neural network may comprise one or more convolutional layers, dilated layers or fully connected layers. The number of convolutional layers may be between 1-10 and dilated layers between 0-10. The total number of convolutional layers (including input and output layers) may be at least about 1, 2, 3, 4, 5, 10, 15, 20, or greater, and the total number of dilated layers may be at least about 1, 2, 3, 4, 5, 10, 15, 20, or greater. The total number of convolutional layers may be at most about 20, 15, 10, 5, 4, 3 or less, and the total number of dilated layers may be at most about 20, 15, 10, 5, 4, 3 or less. In some embodiments, the number of convolutional layers is between 1-10 and fully connected layers between 0-10. The total number of convolutional layers (including input and output layers) may be at least about 1, 2, 3, 4, 5, 10, 15, 20, or greater, and the total number of fully connected layers may be at least about 1, 2, 3, 4, 5, 10, 15, 20, or greater. The total number of convolutional layers may be at most about 20, 15, 10, 5, 4, 3 or less, and the total number of fully connected layers may be at most about 20, 15, 10, 5, 4, 3 or less.

A convolutional neural network (CNN) may be deep and feed-forward artificial neural networks. A CNN may be applicable to analyzing visual imagery. A CNN may comprise an input, an output layer, and multiple hidden layers. Hidden layers of a CNN may comprise convolutional layers, pooling layers, fully connected layers and normalization layers. Layers may be organized in 3 dimensions: width, height and depth.

Convolutional layers may apply a convolution operation to an input and pass results of a convolution operation to a next layer. For processing images, a convolution operation may reduce the number of free parameters, allowing a network to be deeper with fewer parameters. In a convolutional layer, neurons may receive input from only a restricted subarea of a previous layer. Convolutional layer's parameters may comprise a set of learnable filters (or kernels). Learnable filters may have a small receptive field and extend through the full depth of an input volume. During a forward pass, each filter may be convolved across the width and height of an input volume, compute a dot product between entries of a filter and an input, and produce a 2-dimensional activation map of that filter. As a result, a network may learn filters that activate when it detects some specific type of feature at some spatial position in an input.

Pooling layers may comprise global pooling layers. Global pooling layers may combine outputs of neuron clusters at one layer into a single neuron in the next layer. For example, max pooling layers may use the maximum value from each of a cluster of neurons at a prior layer; and average pooling layers may use an average value from each of a cluster of neurons at the prior layer. Fully connected layers may connect every neuron in one layer to every neuron in another layer. In a fully-connected layer, each neuron may receive input from every element of a previous layer. A normalization layer may be a batch normalization layer. A batch normalization layer may improve a performance and stability of neural networks. A batch normalization layer may provide any layer in a neural network with inputs that are zero mean/unit variance. Advantages of using batch normalization layer may include faster trained networks, higher learning rates, easier to initialize weights, more activation functions viable, and simpler process of creating deep networks.

A neural network may comprise a recurrent neural network. A recurrent neural network may be configured to receive sequential data as an input, such as consecutive data inputs, and a recurrent neural network software module may update an internal state at every time step. A recurrent neural network can use internal state (memory) to process sequences of inputs. A recurrent neural network may be applicable to tasks such as handwriting recognition or speech recognition, next word prediction, music composition, image captioning, time series anomaly detection, machine translation, scene labeling, and stock market prediction. A recurrent neural network may comprise fully recurrent neural network, independently recurrent neural network, Elman networks, Jordan networks, Echo state, neural history compressor, long short-term memory, gated recurrent unit, multiple timescales model, neural turning machines, differentiable neural computer, neural network pushdown automata, or any combination thereof.

A trained algorithm may comprise a supervised or unsupervised learning method such as, for example, SVM, random forests, clustering algorithm (or software module), gradient boosting, logistic regression, and/or decision trees. Supervised learning algorithms may be algorithms that rely on the use of a set of labeled, paired training data examples to infer the relationship between an input data and output data. Unsupervised learning algorithms may be algorithms used to draw inferences from training data sets to output data. Unsupervised learning algorithm may comprise cluster analysis, which may be used for exploratory data analysis to find hidden patterns or groupings in process data. One example of unsupervised learning method may comprise principal component analysis. Principal component analysis may comprise reducing the dimensionality of one or more variables. The dimensionality of a given variables may be at least 1, 5, 10, 50, 100, 200, 300, 400, 500, 600, 700, 800, 900, 1000, 1100, 1200 1300, 1400, 1500, 1600, 1700, 1800, or greater. The dimensionality of a given variables may be at most 1800, 1600, 1500, 1400, 1300, 1200, 1100, 1000, 900, 800, 700, 600, 500, 400, 300, 200, 100, 50, 10 or less.

A statistical based algorithm may be obtained through statistical techniques. In some embodiments, statistical techniques may comprise linear regression, classification, resampling methods, subset selection, shrinkage, dimension reduction, nonlinear models, tree-based methods, support vector machines, unsupervised learning, or any combination thereof.

A linear regression may be a method to predict a target variable by fitting the best linear relationship between a dependent and independent variable. The best fit may mean that the sum of all distances between a shape and actual observations at each point is the least. Linear regression may comprise simple linear regression and multiple linear regression. A simple linear regression may use a single independent variable to predict a dependent variable. A multiple linear regression may use more than one independent variables to predict a dependent variable by fitting a best linear relationship. In some embodiments, the matching engine may be configured to categorize insights automatically to one or several domains or milestones using, for example, NLP methods and/or machine learning methods for multi-class and multi-label text categorization.

In some embodiments, the matching engine may be further configured to retrieve data stored in a database. The data may include lists of questions and answers relating to SLTs that are obtained from reputable/reliable websites, or the like. For example, if a SLT relates to cancer, the matching engine may retrieve questions and answers from a reputable website, such as a website operated by the American Cancer Society.

The system may also comprise a recommendation engine. The recommendation engine can recommend one or more different users to a particular user. The recommended people may be users of the user matching platform. The recommended people may be someone who have experienced, are experiencing, or are about to experience same life events or steps with the user. The recommendation engine may also be configured to map the community wisdom to the milestones or steps on the user's timeline, so as provide personalized recommendations to the user for each milestone or step. The recommendation engine may be capable of predicting the user's needs based on the user query, as previously described. In some embodiments, the recommendation engine can predict the user's needs based on: (1) the user's profile, (2) information obtained directly or indirectly from the user, (3) user's action (or inaction) regarding certain matters, and/or (4) user's interaction with other users. The recommendation engine can determine similarity based on parameters including the users' age, ethnicity, geographical location, type of SLT and milestones, income, personality, spending habits, etc.

A non-transitory computer-readable storage medium including instructions that, when executed by a server, cause the server to perform operations may comprise: receiving input data from the plurality of devices, wherein the input data comprises queries, comments or insights from different users relating to the one or more life events, wherein each life event comprises a plurality of different steps on a timeline; analyzing the input data to determine, for each user and life event, which steps on the timeline that each user (a) has experienced, (b) is currently experiencing, or (c) likely to experience in the future; and matching the plurality of users with one another, based on the life events and the steps that the users have experienced, are currently experiencing, or likely to experience in the future, in order to assist the users in navigating one or more life events.

The non-transitory computer readable medium may be operatively coupled with components for transmitting the result. Components for transmitting can include wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples for wireless communication components can include a Wi-Fi receiver, a component for accessing a mobile data standard such as a 3G or 4G LTE data signal, or a Bluetooth receiver. All these data in the non-transitory computer readable medium may be collected and archived to build a data warehouse.

Applications Example 1 (Diagnosis with Cancer)

For example, a person going through a SLT of having been diagnosed with cancer may wonder about how to proceed with treatment. A journey to overcome cancer thus begins. The individual can try to find someone in the community for advice about cancer treatment and how to manage this illness. Various members of the community may have experiences regarding cancer treatment and how to manage the illness. Even before the individual joins the community, the application or platform can collect the information of the various members who are already members of the community and have experiences regarding the cancer treatment as data, and can filter out the relevant information. To find someone in the community for advice about cancer treatment, the individual may answer a set of questions provided by the application. During the questioning and answering process, the application can navigate its database to find a match to the individual. The individual may then choose to add the match as a new contact and start to communicate with the match. The matched user can contribute his/her wisdom regarding cancer treatment or how to manage to the illness, to the individual. For example, the matched user can inform the individual on the types of cancer treatment, recommend a suitable type of cancer treatment for the user, suggest medical providers that fit the user's budget/needs, provide advice on side effects resulting from the cancer treatment, as well as other non-clinical aspects of the cancer treatment (e.g., impact on family, finances, job, etc.). Accordingly, the individual is then given the "wisdom" of the matched user through the application or platform.

Applications Example 2 (Preparing for Loss of a Loved One)

A person going through a SLT of losing a loved one may wonder about how to brace the family together during those difficult times, how to inform friends and family about the loss, and how to prepare for the funeral. A journey of preparing for the above thus begins. The individual can try to find someone in the community for advice about how to deal with loss of a loved one. Various members of the community may have experiences regarding the loss of a loved one. Even before the individual joins the community, the application or platform can collect the information of the various members who are already member of the community and have experiences regarding loss of a loved one as data, and filter out the relevant information. To find someone in the community who can provide advice about loss of a loved one, the individual may answer a set of questions provided by the application. During the questioning and answering process, the application or platform can navigate its database to find a match to the individual. The individual may then choose to add the match as a new contact and start to communicate with the match. The matched user can contribute his/her wisdom regarding the loss of a loved one to the individual. For example, the matched user can inform the individual about various aspects of managing the loss of a loved one. Accordingly, the individual is then provided the "wisdom" of the matched user through the application or platform.

Next, various embodiments of the invention will be described with reference to the drawings.

FIG. 1 illustrates an exemplary network layout 100 in accordance with some embodiments. In one aspect, network layout 100 may include user device 102, server 104, network 106, database(s) 108, and user matching system(s) 110. Each of the components 102, 104, 108, and 110 may be operatively connected to one another via network 106 or any type of communication links that allows transmission of data from one component to another. The user matching system can be provided as part of an event navigation system, or separately from an event navigation system. Examples of event navigation systems are described in U.S. Pat. No. 9,710,757, which is incorporated herein in its entirety User device 102 may be, for example, one or more computing devices configured to perform one or more operations consistent with the disclosed embodiments. For example, user device 102 may be a computing device that can display one or more webpages. User device 102 can include, among other things, desktop computers, laptops or notebook computers, mobile devices (e.g., smart phones, cell phones, personal digital assistants (PDAs), and tablets), and wearable devices (e.g., smartwatches). User device 102 can also include any other media content player, for example, a set-top box, a television set, a video game system, or any electronic device capable of providing or rendering data. User device 102 may include known computing components, such as one or more processors, and one or more memory devices storing software instructions executed by the processor(s) and data.

In certain embodiments, one or more users may operate user device 102 to perform one or more operations consistent with disclosed embodiments. Alternatively, a user may operate one or more user devices 102 to perform one or more operations consistent with disclosed embodiments. A user as described herein may refer to an individual, a group of individuals, a support group comprising a group of individuals, a common interests group comprising a group of individuals, etc. The support group may be, for example, a group of people sharing their experiences how dealing with a significant life transition (e.g., diagnosed with a terminal illness, going through a divorce, etc.). The common interests group may be, for example, a group of people who have common goals or interests or a common timeline (e.g., going to college, or upcoming retirement, etc.). A user may be registered or associated with an entity that provides services associated with one or more operations performed by the disclosed embodiments. For example, the user may be a registered user of an entity (e.g., a company, an organization, an individual, etc.) that provides one or more of servers 104, database(s) 108, and/or user matching system(s) 110 to perform operations for assisting the user in navigating through events happening in the user's life, the operations being consistent with certain disclosed embodiments. The events may be related to significant life transitions (SLTs), as described below.

User device 102 may be configured to receive input from one or more users. A user may provide may provide an input to user device 102 using an input device, for example, a keyboard, a mouse, a touch-screen panel, voice recognition and/or dictation software, or any combination of the above. The user input may include questions, comments, or statements made by one or more users. Different users may provide different input, and the input may relate to any subject matter. For example, a user may be going through a significant life transition (SLT), such as going to college, getting married, having children, starting a business, getting divorced, retirement, relocation, or diagnosed with a terminal illness, among others. In those instances, the user's input may be indicative of the user's thoughts, feelings, moods, opinions, general questions regarding any of the abovementioned SLTs, and/or specific questions regarding certain topics within a SLT.

In some embodiments, a plurality of user devices 102 may be provided. One or more users may be associated with each user device 102. Alternatively, one or more devices 102 may be associated with each user. The disclosed embodiments are not limited to any specific relationships or affiliations between user(s) of device 102 and an entity, person(s), or entities providing server 104, database(s) 108, and user matching system(s) 110.

Server 104 may be one or more server computers configured to perform one or more operations consistent with disclosed embodiments. In one aspect, server 104 may be implemented as a single computer, through which user device 102 is able to communicate with other components of network layout 100 illustrated in FIG. 1. In some embodiments, user device 102 may communicate with server 104 through network 106. In other embodiments, server 104 may communicate on behalf of user device 102 with user matching system(s) 110 or database(s) 108 through network 106. In some embodiments, server 104 may embody the functionality of one or more of user matching system(s) 110. In some embodiments, user matching system(s) 110 may be implemented inside and/or outside of server 104. For example, user matching system(s) 110 may be software and/or hardware components included with server 104 or remote from server 104.

In some embodiments, user device 102 may be directly connected to server 104 through a separate link (not shown in FIG. 1). In certain embodiments, server 104 may be configured to operate as a front-end device configured to provide access to one or more user matching system(s) 110 consistent with certain disclosed embodiments. Server 104 may, in some embodiments, utilize user matching system(s) 110 to process user input from user device 102 in order to match the user with other members in the community. Server 104 may be configured to search, retrieve, and analyze data and information stored in database(s) 108. The data and information may include questions, answers, comments, and insights relating to different SLTs, milestones and/or the user's needs. While FIG. 1 illustrates server 104 as a single server, in some embodiments, multiple devices may implement the functionality associated with server 104.

Server 104 may include a web server, an enterprise server, or any other type of computer server, and can be computer programmed to accept requests (e.g., HTTP, or other protocols that can initiate data transmission) from a computing device (e.g., user device 102) and to serve the computing device with requested data. In addition, server 104 can be a broadcasting facility, such as free-to-air, cable, satellite, and other broadcasting facility, for distributing data. Server 104 may also be a server in a data network (e.g., a cloud computing network).

Server 104 may include known computing components, such as one or more processors, one or more memory devices storing software instructions executed by the processor(s), and data. Server 104 can have one or more processors and at least one memory for storing program instructions. The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods can be implemented in hardware components or combinations of hardware and software such as, for example, ASICs, special purpose computers, or general purpose computers. While FIG. 1 illustrates server 104 as a single server, in some embodiments, multiple devices may implement the functionality associated with server.

Network 106 may be a network that is configured to provide communication between various components of network layout 100 depicted in FIG. 1. Network 106 may be implemented, in some embodiments, as one or more networks that connect devices and/or components in network layout 100 for allowing communication between them. For example, as one of ordinary skill in the art will recognize, network 106 may be implemented as the Internet, a wireless network, a wired network, a local area network (LAN), a Wide Area Network (WANs), Bluetooth, Near Field Communication (NFC), or any other type of network that provides communications between one or more components of network layout 100. In some embodiments, network 106 may be implemented using cell and/or pager networks, satellite, licensed radio, or a combination of licensed and unlicensed radio. Network 106 may be wireless, wired, or a combination thereof.

User matching system(s) 110 may be implemented as one or more computers storing instructions that, when executed by processor(s), process user input from user device 102 in order to determine the user's milestones and needs, and to match the user to someone who have experienced, are experiencing, or are likely to experience the life events that the user is interested in. User matching system(s) 110 may search, retrieve, and analyze data and information stored in database(s) 108. The data and information may include questions, comments, and insights relating to different SLTs, milestones and/or the user's needs. In some embodiments, server 104 may be the computer in which user matching system(s) 110 are implemented.

However, in some embodiments, at least some of user matching system(s) 110 may be implemented on separate computers. For example, user device 102 may send a user input to server 104, and server 104 may connect to user matching system(s) 110 over network 106 to retrieve, filter, and analyze data from database(s) 108. In other embodiments, user matching system(s) 110 may represent software that, when executed by processor(s), perform processes for determining the user's needs, and matching the user to someone who have experienced, are experiencing, or are likely to experience the life events that the user is interested in.

For example, server 104 may access and execute user matching system(s) 110 to perform one or more processes consistent with the disclosed embodiments. In certain configurations, user matching system(s) 110 may be software stored in memory accessible by server 104 (e.g., in memory local to server 104 or remote memory accessible over a communication link, such as network 106). Thus, in certain aspects user matching system(s) 110 may be implemented as one or more computers, as software stored on a memory device accessible by server 104, or a combination thereof. For example, one user matching system(s) 110 may be a computer executing one or more matching techniques, and another user matching system(s) 110 may be software that, when executed by server 104, performs one or more user matching techniques.

The user matching system(s) 110 can assist in matching the user to someone who have experienced, are experiencing, or are likely to experience the life events that the user is interested in. As previously described, such events may be related to significant life transitions (SLTs), for example, going to college, getting married, having children, starting a business, getting divorced, retirement, relocation, or diagnosed with a terminal illness, among others. User matching system(s) 110 may be configured to perform user matching for the user using a plurality of ways. For example, one of user matching system(s) 110 may store and/or execute software that performs an algorithm for processing user input, identifying an event from the user input, determining relevant milestone(s) and need(s) associated with the event, and finding a match for the user. Another of user matching system(s) 110 may store and/or execute software that performs an algorithm for defining and classifying a plurality of topics relating to those milestone(s) and need(s). Another of user matching system(s) 110 may store and/or execute software that performs an algorithm for searching and extracting questions stored in one of database(s) 108 relating to those topics/milestone(s). Another of user matching system(s) 110 may store and/or execute software that performs an algorithm for searching and extracting insights and comments stored in one of database(s) 108 relating to those topics or milestone(s). Another of user matching system(s) 110 may store and/or execute software that performs an algorithm for filtering the questions and insights, and matching the filtered questions/insights to the user's needs/milestones. Another of user matching system(s) 110 may store and/or execute software that performs an algorithm for sorting the matched insights/questions, and providing personalized recommendations to the user based on the user's milestones, timeline and needs. Another of user matching system(s) 110 may store and/or execute software that performs an algorithm for matching the user to someone who have experienced, are experiencing, or are likely to experience the life events that the user is interested in. The disclosed embodiments may be configured to implement user matching system(s) 110 such that a variety of algorithms may be performed for performing one or more user matching techniques. Although a plurality of user matching system(s) 110 have been described for performing the above algorithms, it should be noted that some or all of the algorithms may be performed using a single user matching system 110, consistent with disclosed embodiments.

User device 102, server 104, and user matching system(s) 110 may be connected or interconnected to one or more database(s) 108. Database(s) 108 may be one or more memory devices configured to store data. Additionally, database(s) 108 may also, in some embodiments, be implemented as a computer system with a storage device. In one aspect, database(s) 108 may be used by components of network layout 100 to perform one or more operations consistent with the disclosed embodiments.

In one embodiment, database(s) 108 may comprise storage containing a variety of data sets consistent with disclosed embodiments. For example, database(s) 108 may include, for example, data from the internet. The data may include lists of questions and answers relating to SLTs that may be obtained from reputable/reliable websites, or the like. For example, if a SLT relates to cancer, the questions and answers may be obtained from a reputable website operated by the American Cancer Society. In some embodiments, database(s) 108 may include crowd-sourced data comprising comments and insights relating to SLTs obtained from internet forums and social media websites. The Internet forums and social media websites may include personal and/or group blogs, Facebook™, Twitter™, Reddit™, etc. Additionally, in some embodiments, database(s) 108 may include crowd-sourced data comprising comments and insights relating to SLTs, whereby those comments and insights are directly input by one or more contributors into the user matching system(s) 110. The crowd-sourced data may contain up-to-date or current information on SLTs, how to handle SLTs, milestones in each SLT, etc. The crowd-sourced data may be provided by other users or contributors who have experience with those SLTs. For example, those users or contributors may be currently undergoing a SLT, about to complete a SLT, or completed a SLT. It is noted that those users or contributors may be at different phases within a SLT.

In certain embodiments, one or more database(s) 108 may be co-located with server 104, may be co-located with one another on network 106, or may be located separately from other devices (signified by the dashed line connecting one of database(s) 108). One of ordinary skill will recognize that the disclosed embodiments are not limited to the configuration and/or arrangement of database(s) 108.

Any of user device 102, server 104, database(s) 108, or user matching system(s) 110 may, in some embodiments, be implemented as a computer system. Additionally, while network 106 is shown in FIG. 1 as a "central" point for communications between components of system 100, the disclosed embodiments are not so limited. For example, one or more components of network layout 100 may be interconnected in a variety of ways, and may in some embodiments be directly connected to, co-located with, or remote from one another, as one of ordinary skill will appreciate. Additionally, while some disclosed embodiments may be implemented on server 104, the disclosed embodiments are not so limited. For instance, in some embodiments, other devices (such as user matching system(s) 110 and/or database(s) 108) may be configured to perform one or more of the processes and functionalities consistent with the disclosed embodiments, including embodiments described with respect to server 104.

Although particular computing devices are illustrated and networks described, it is to be appreciated and understood that other computing devices and networks can be utilized without departing from the spirit and scope of the embodiments described herein. In addition, one or more components of network layout 100 may be interconnected in a variety of ways, and may in some embodiments be directly connected to, co-located with, or remote from one another, as one of ordinary skill will appreciate.

Figure 2:
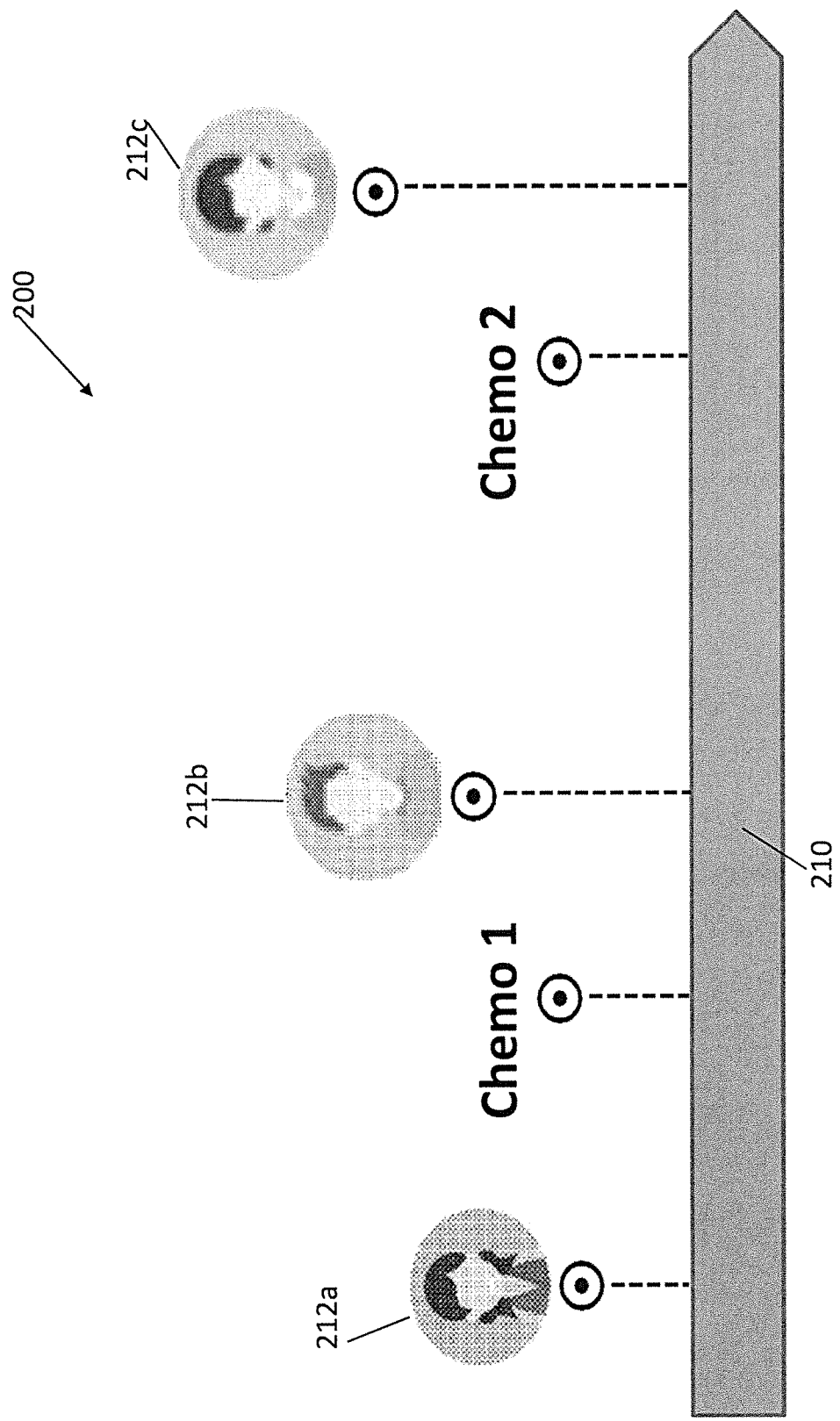
FIG. 2 illustrates an exemplary timeline window, in accordance with some embodiments.

FIG. 2 illustrates an exemplary timeline window 200 in accordance with some embodiments. Window 200 may be indicative of a timeline of a SLT, whereby a plurality of different users, feeds, and milestones are provided along the timeline. In other words, window 200 may represent a map of users and milestones along the timeline.

In FIG. 2, a timeline 210 is depicted. The timeline may be associated with a SLT or life event. The chronology order of the timeline may extend from left to right. A plurality of users 212a, 212b, and 212c and a plurality of milestones or steps (e.g., Chemo 1 and Chemo 2) may be displayed along the timeline. Users can tag, bookmark, forward, comment, delete, or 'like' a feed. As shown in FIG. 2, user 212a has yet to go through milestone Chemo 1, user 212b has already gone through milestone Chemo 1 but has yet to go through milestone Chemo 2, and user 212c has already gone through both milestones Chemo 1 and Chemo 2. Thus, user 212c is furthest along the SLT journey (possibly the most experienced), whereas user 212a may have just embarked on the SLT journey (possibly the least experienced). Users 212a, 212b, and 212c can anticipate which and when the milestones on the SLT journey are, by looking at the timeline and comparing their present positions relative to the milestones. During the matching process, user 212a may be matched to user 212b because user 212b may provide insights regarding Chemo 1 to the user 212b. Similarly, user 212a can also be matched to user 212c because user 212c may provide insights regarding Chemo 1 and Chemo 2 to user 212a. Likewise, user 212b can also be matched to user 212c because user 212c may provide insights regarding Chemo 2 to the user 212b.

Figure 3:
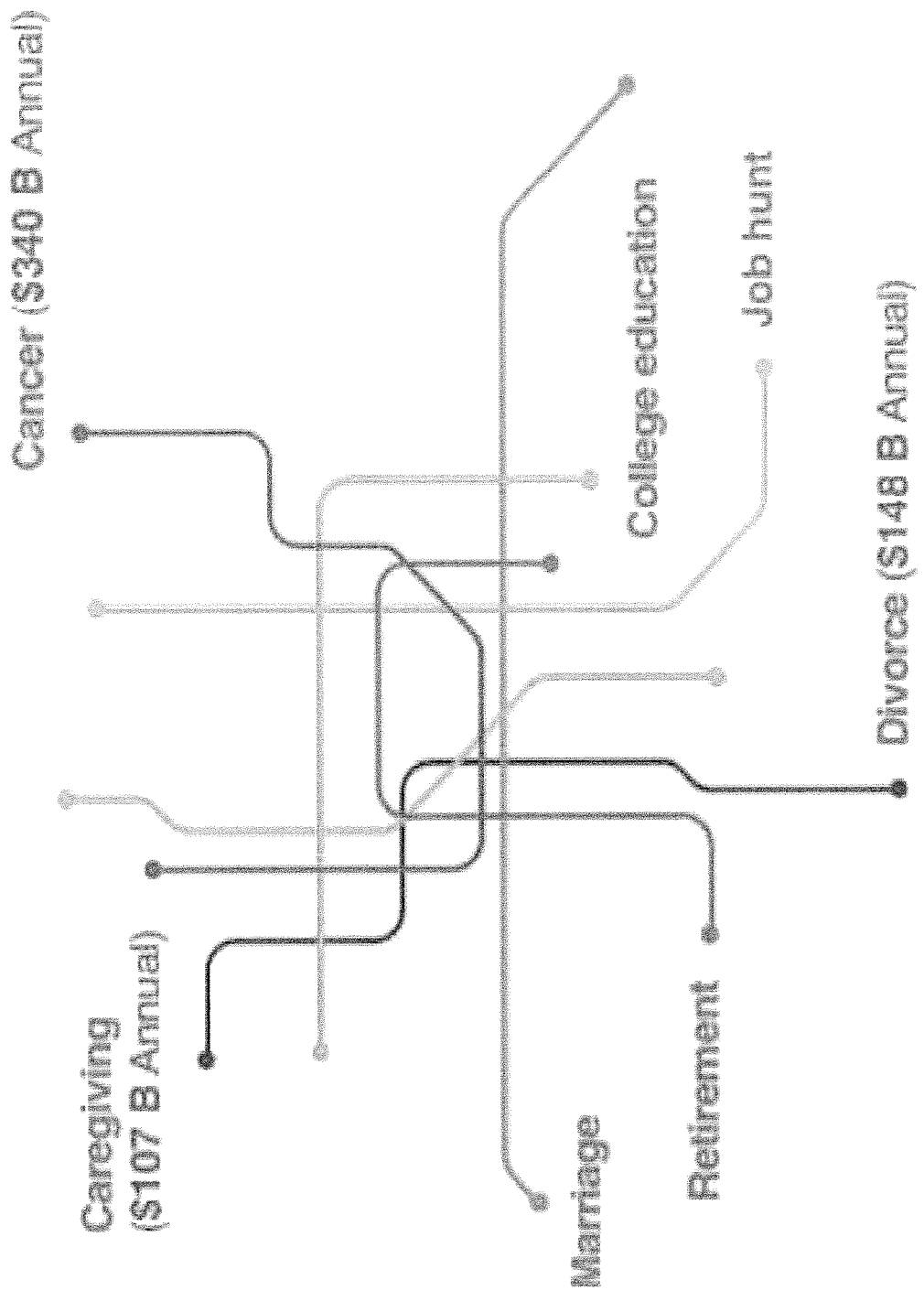
FIG. 3 illustrates an exemplary SLT map, in accordance with some embodiments.

FIG. 3 illustrates an exemplary SLT map 300 in accordance with some embodiments. Map 300 may include a plurality of SLTs such as college education, job hunt, marriage, divorce, retirement, a terminal illness (e.g., cancer), and/or caregiving. Each SLT may be represented by a timeline of a different color. For example, caregiving may be represented by a red timeline, and cancer may be represented by a purple timeline. It is noted that any type of visual scheme comprising different shapes, colors, icons, etc. can be used to illustrate the different SLTs. In some cases, the SLT timelines may be interconnected to one another. For example, job hunt may be preceded by college education, and divorce may be preceded by marriage. A user may experience some or all of these SLTs at different stages of their lives. In some instances, more than one SLT may occur during a same stage of the user's life (e.g., terminal illness occurring during retirement).

Figure 4:
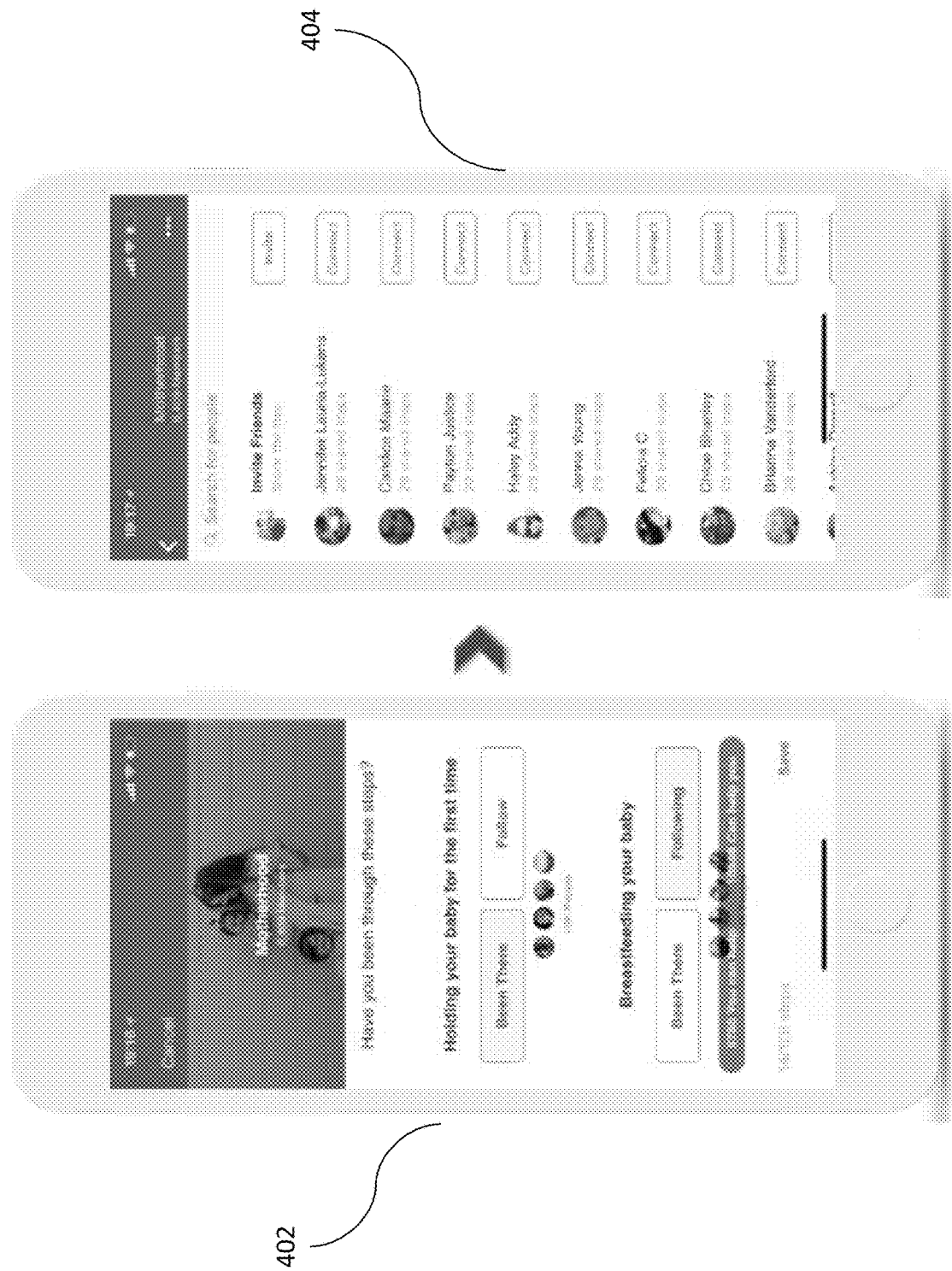
FIG. 4 illustrates exemplary user interfaces, in accordance with some embodiments.

FIG. 4 illustrates exemplary user interfaces 402 and 404 in accordance with some embodiments. In the example of FIG. 4, the user interface 402 may comprise a plurality of questions corresponding to one or more milestones for the user to answer. The answers to these questions for the one or more milestones may allow the user matching platform to uncover the user's experience and help the user to discover his/her match. For instance, the user interface 402 may comprise a plurality of milestones or steps related to motherhood. The milestones may comprise "holding your baby for the first time" and "breastfeeding your baby." The number of milestones may be at least 1, 5, 10, 15, 20, 25, 30, 35, 40, 45, 50 or greater. In some cases, the number of milestones may be at most 50, 45, 40, 35, 30, 25, 20, 15, 10, 5, or less. The choices the user can pick may comprise "been there" or "follow." Based on the choices that user makes, the user matching platform may show the user a list of people who have experienced some or all of the milestones that the user is interested in. For example, the user interface 404 shows a list of at least 9 people who have experienced some or all of the milestones that the user is interested in. The people in the list may be arranged from top to bottom based on the number of shared steps with the user the person having the most number of shared steps may be positioned near the top of the viewing screen to signify that the person is likely to be closest match. In the example of FIG. 4, the person, Jennifer in the user interface 404, may be arranged near the top of the list in user interface 404 because Jennifer has the most number of shared steps with the user. The user may invite the at least 9 people (or any number of recommended matches) in the user interface 404 to be friends with the user. If the user connects with any of the at least 9 people as a friend, the user may start communication with the person.

Figure 5:
FIG. 5 illustrates exemplary user interfaces, in accordance with some further embodiments.

FIG. 5 illustrates exemplary user interfaces 502 and 504 in accordance with some embodiments. In the example of FIG. 5, the user may use the user matching platform to find other people who have experienced a career change. The user interfaces 502 and 504 may comprise a plurality of questions corresponding to one or more milestones for the user to answer. The answers to these questions may allow the user matching platform to uncover the user's experience and help the user to discover his/her match. For instance, the user interfaces 502 and 504 may comprise a plurality of milestones, including "seeking a real change," "finding your purpose," "becoming passionate about a cause," "getting recruited," and "witnessing a traumatic situation." The choices the user can pick may comprise "been there" or "follow." When selecting the choices, the user can also provide his/her own insights of the experience by adding one or more steps that might have been missed. After the user selects the choices, the user may view on the user interfaces as to how many people the user can help or provide guidance to, and conversely how many people the user can receive help or guidance from. For instance, in user interface 502, after the user selects that he/she has "been there" for seeing a real change and finding the purpose, the user can see from the bottom of the user interface 502 that the user may be able to help or provide guidance to 5239 people, and there are 652 people who may be able to help or provide guidance to the user. The user can also save/store the findings or search results by selecting the save bottom on the right bottom of the user interface 502. Similarly, in user interface 504, after the user selects that he/she has "been there" for becoming passionate about a cause and getting recruited, and "follows" witnessing a traumatic situation, the user can see from the bottom of the user interface 504 that the user may be able to help or provide guidance to 478 people, and conversely there are 181 people who may be able to help or provide guidance the user. The user can also save/store the findings or search results by selecting the save bottom on the right bottom of the user interface 504.

Figure 6:
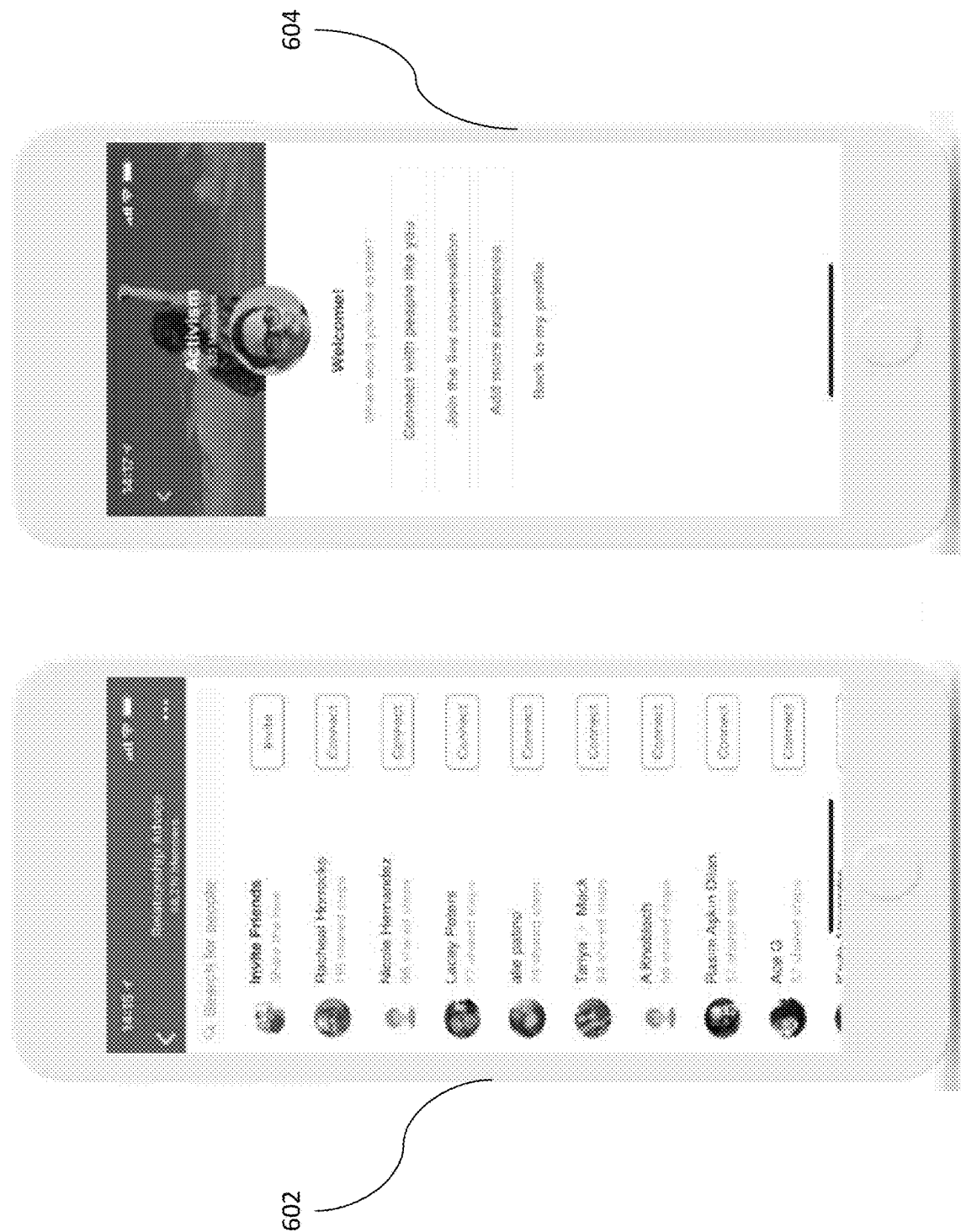
FIG. 6 illustrates exemplary user interfaces, in accordance with some further embodiments.

FIG. 6 illustrates exemplary user interfaces 602 and 604 in accordance with some embodiments. In the example of FIG. 6, the user may have already selected the choices to a plurality of questions corresponding to one or more milestones regarding relationship advice. The user may then use the user matching platform to find people who can provide relationship advice. The user matching platform may show the user a list of people who have experienced some or all of the milestones that the user has experienced regarding relationship advice. For example, the user interface 602 shows a list of at least 9 people who have experienced some or all of the milestones that the user has experienced during relationships. The list of people may be arranged from top to bottom based on the number of the shared steps with the user the person having the most number of shared steps may be positioned near the top of the viewing screen to signify that the person is likely to be closest match. The person, Rachel as shown in the user interface, may be arranged near the top of the list in user interface 602 because Rachel has the most number of shared steps with the user. The user may invite one or more people in the list (on the user interface 604) to be a friend. If the user connects with any of the people on the list as a friend, the user may start communicating with the person to learn from or share wisdom with the person. The user interface may comprise a couple of selections when the user first logs into the user matching platform. For instance, in the user interface 604, when logging in, the user may select among the options including "connect with people like you," "join the live conversation," "add more experiences," and "back to my profile."

Figure 7:
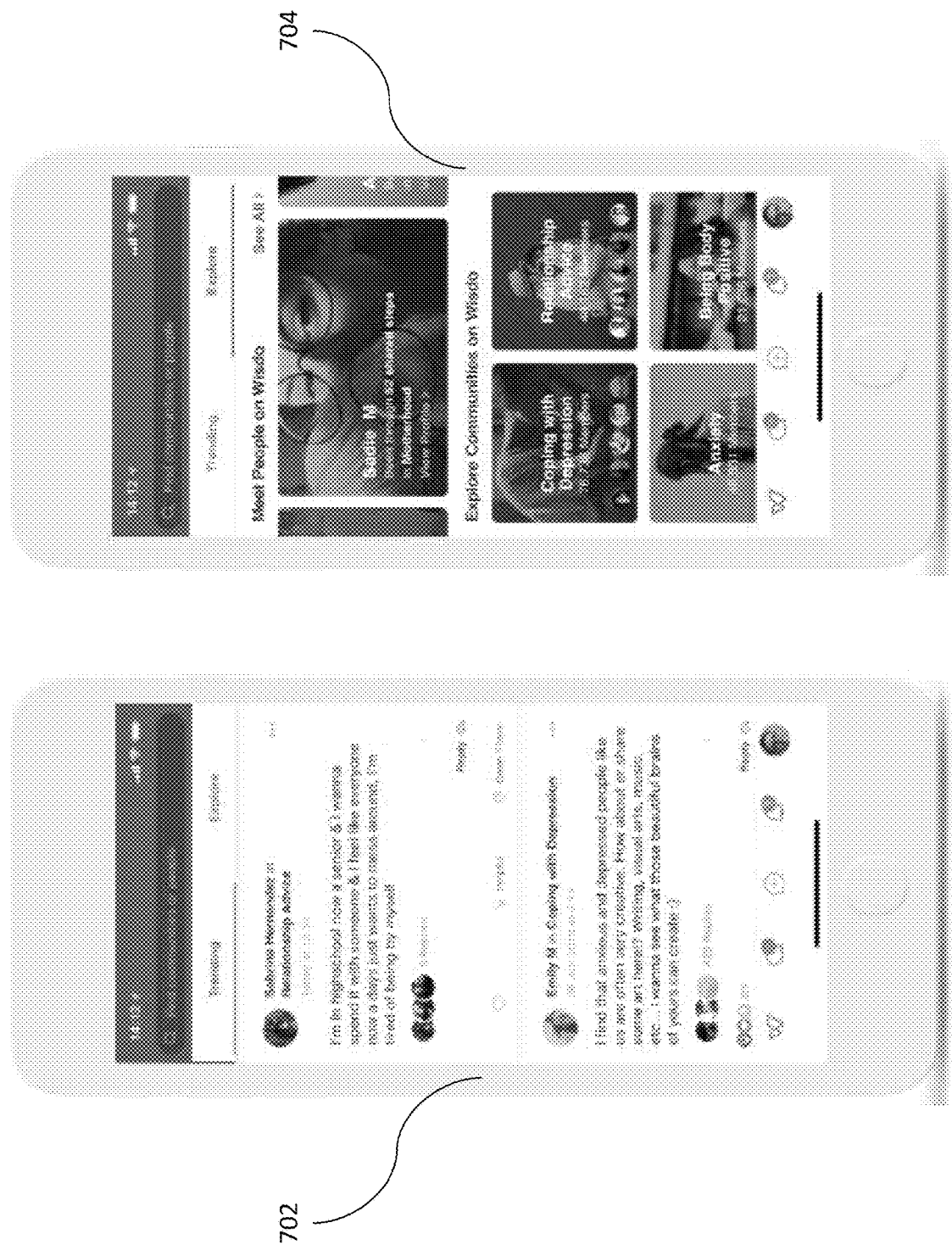
FIG. 7 illustrates exemplary user interfaces, in accordance with some further embodiments.

FIG. 7 illustrates exemplary user interfaces 702 and 704 in accordance with some embodiments. In the example of FIG. 7, the user matching platform may provide recommendations to the user through trending or explore tabs. The user may be able to see trending information regarding any SLT provided by others. For instance, in user interface 702, Sabrina is providing relationship advice to others and 5 other people have replied, and Emily is providing information on how to cope with depression, and 429 other people have replied. The user may also be able to explore other interesting communities and information. For instance, in user interface 704, the user may see the communities he/she is able to explore, and the communities may include coping with depression, relationship advice, anxiety, and being body positive.

Figure 8:
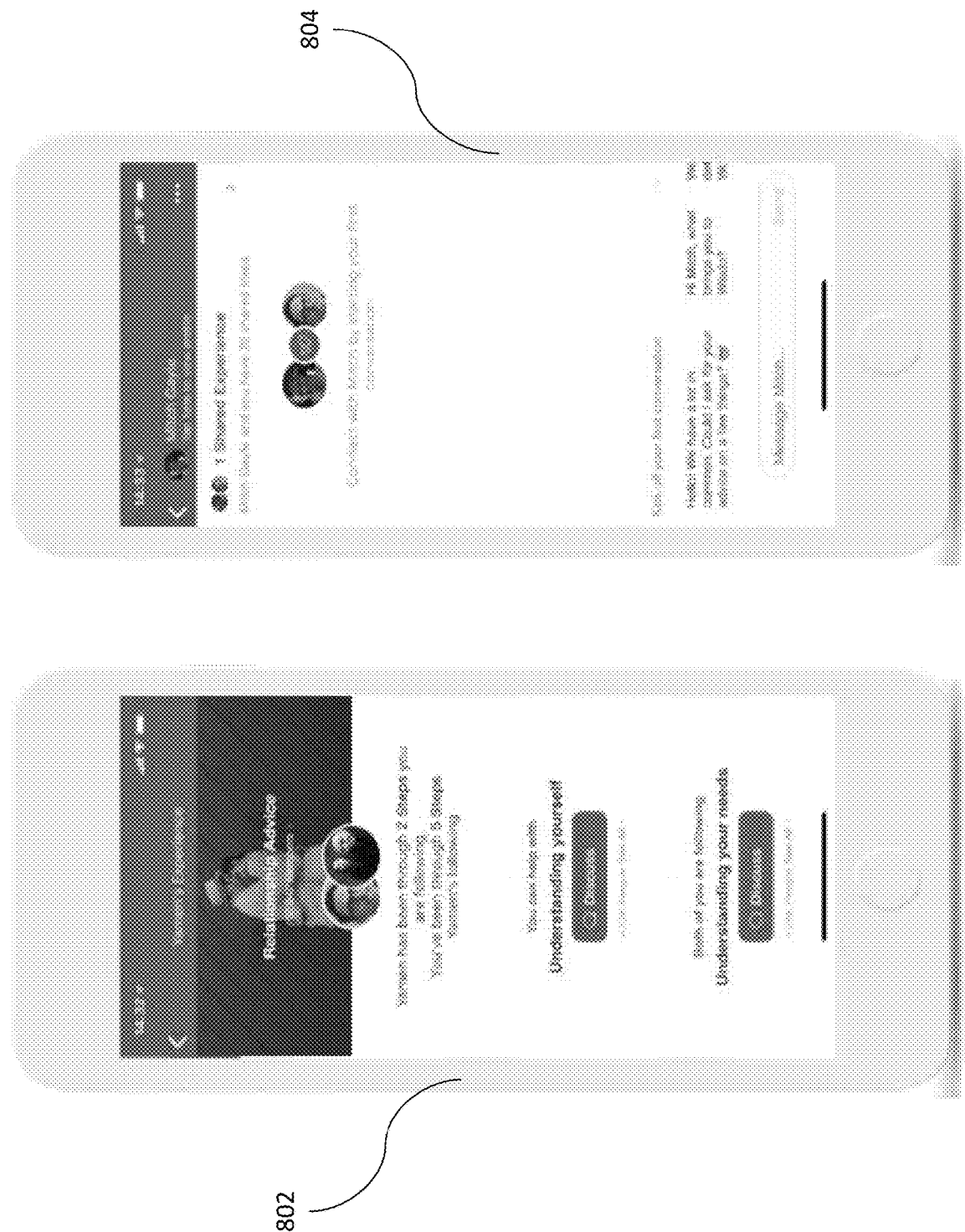
FIG. 8 illustrates an exemplary insights curation list, in accordance with some embodiments.

FIG. 8 illustrates exemplary user interfaces 802 and 804 in accordance with some embodiments. The user matching platform may provide comparison between two users. In the example of FIG. 8, the user may see the profile of others in the user matching platform. For instance, in the user interface 802, the user can see the profile of Yamen regrading Yamen's experiences. In this example, Yamen has been thorough 2 steps that the user is following, and conversely the user has been through 5 steps that Yamen is following. The user can also see that he/she can help Yamen regarding the step "understanding yourself," and both of the user and Yamen are following the step "understanding the needs." In FIG. 8, the user can also connect with other users who share some or all of the milestones with the user regarding an SLT. For instance, in the user interface 804, the user may connect to Mitch and is able to start a communication with Mitch. During the communication, the user can ask Mitch questions regarding the milestones of the SLT, or Mitch can ask the user questions regarding the milestone of the SLT.

Figure 9A:
FIG. 9A illustrates exemplary user interfaces regarding matching users through a buddy program, in accordance with some embodiments.
Figure 9B:
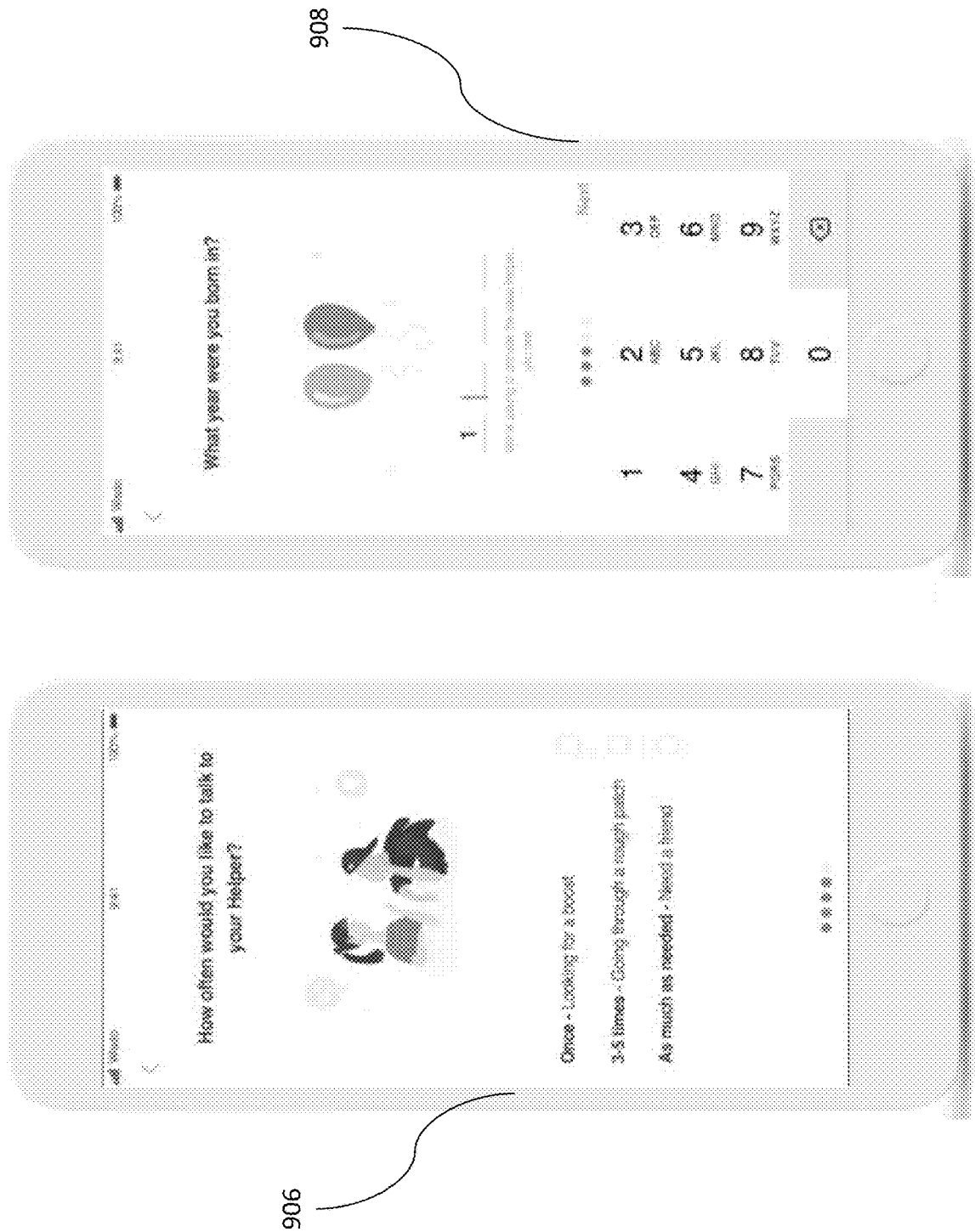
FIG. 9B illustrates some other exemplary user interfaces regarding matching users through a buddy program, in accordance with some embodiments.
Figure 9C:
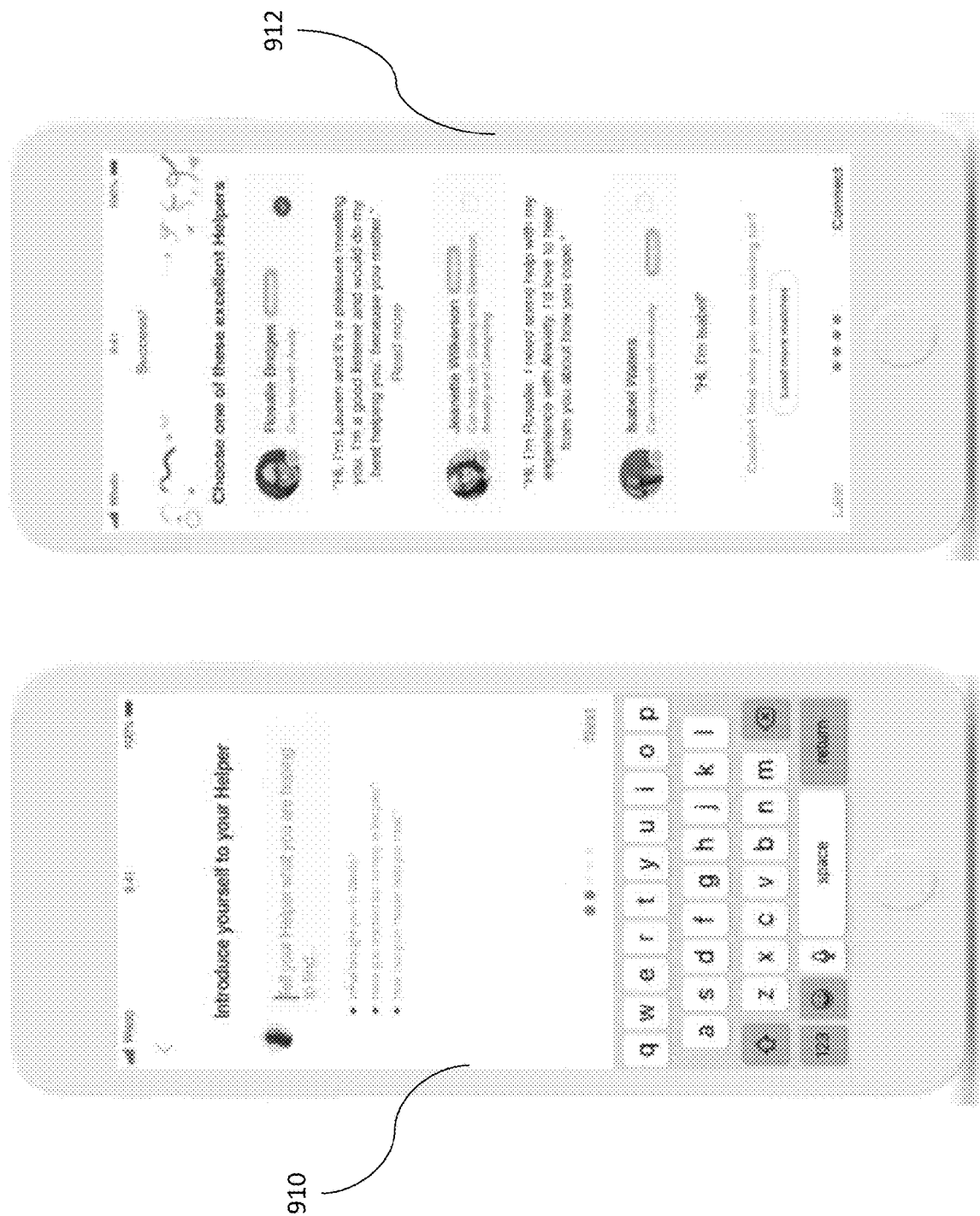
FIG. 9C illustrates some other exemplary user interfaces regarding matching users through a buddy program, in accordance with some embodiments.

FIGS. 9A-9C illustrates exemplary user interfaces regarding matching of users through a buddy program. In the example of FIGS. 9A-9C, the user may go through a plurality of user interfaces to find a match through a buddy program. For instance, in the first user interface 902, the user is asked by the user matching platform to join the buddy program. If the user selects "join today," the user may see the next user interface 904 to select which experience to talk about. In the user interface 904, the user can select one or more options including depression, addiction, motherhood, and anxiety. In the next user interface 906, the user matching platform may ask the user how often the user would like to talk to his/her helper (e.g. mentor), and the user may select once, 3-5 times, or as much as needed. In the next user interface 908, the user matching platform may ask the user to enter his/her personal information, including, birthday, personality, city of birth, and hobbies. In the next user interface 910, the user matching platform may ask the user to introduce himself/herself to the helper (e.g. mentor). The introduction may comprise information regarding why the user has joined the user matching platform, whether the user has reached out for help in the past, and how and in what ways the helper (e.g. mentor) can help the user the most. The next user interface 912 may allow the user to choose one of a plurality of helpers (e.g. mentors).

Figure 10:
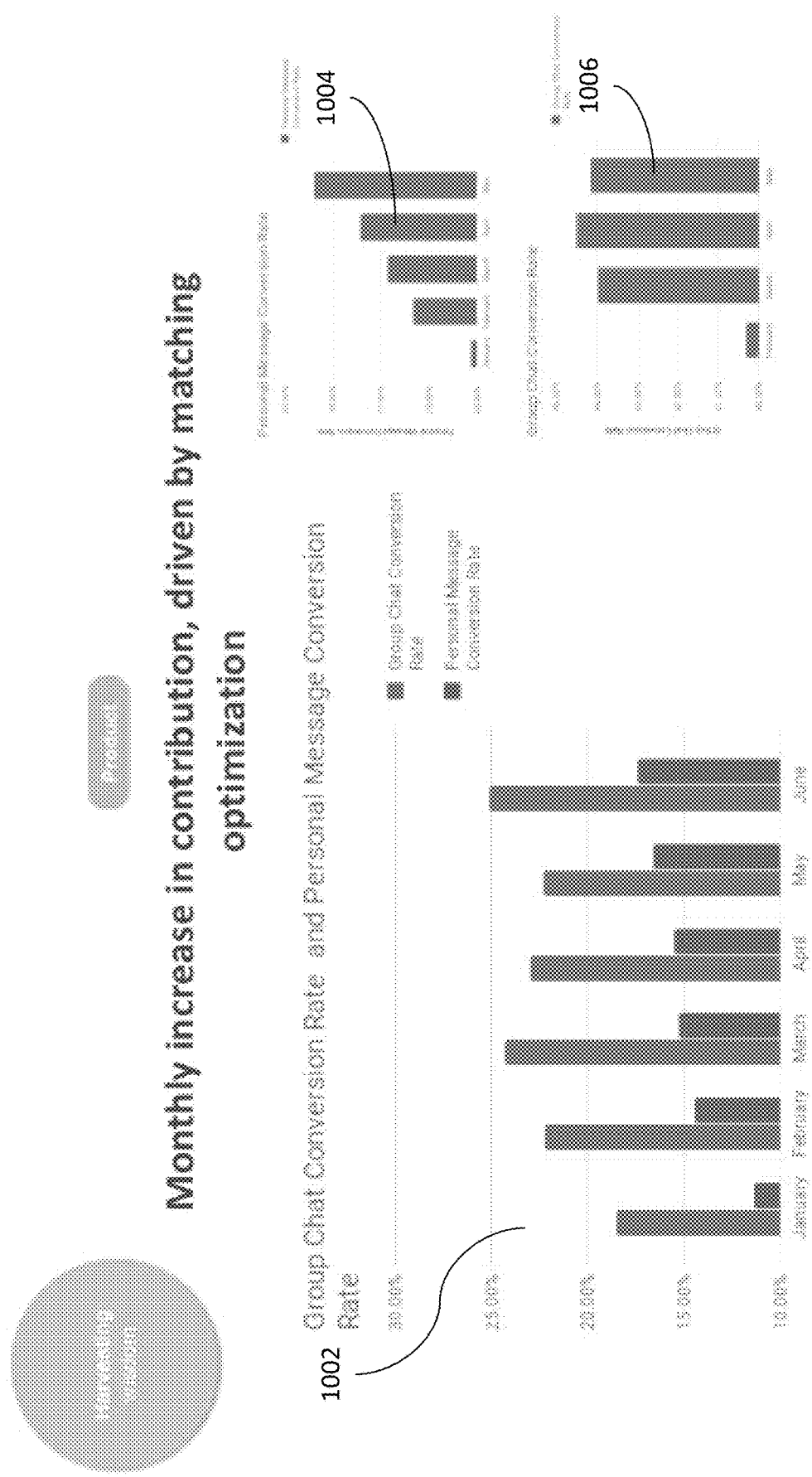
FIG. 10 shows an example of monthly increase in contribution, driven by matching optimization.

FIG. 10 shows an example of monthly increase in contribution, driven by matching optimization. In chart 1002, the personal message conversion rate is shown to increase between January and June. In chart 1004, the personal message conversion rate is shown to increase from January to May. In chart 1006, the group chat conversion rate is shown to increase from February to May.

Figure 11:
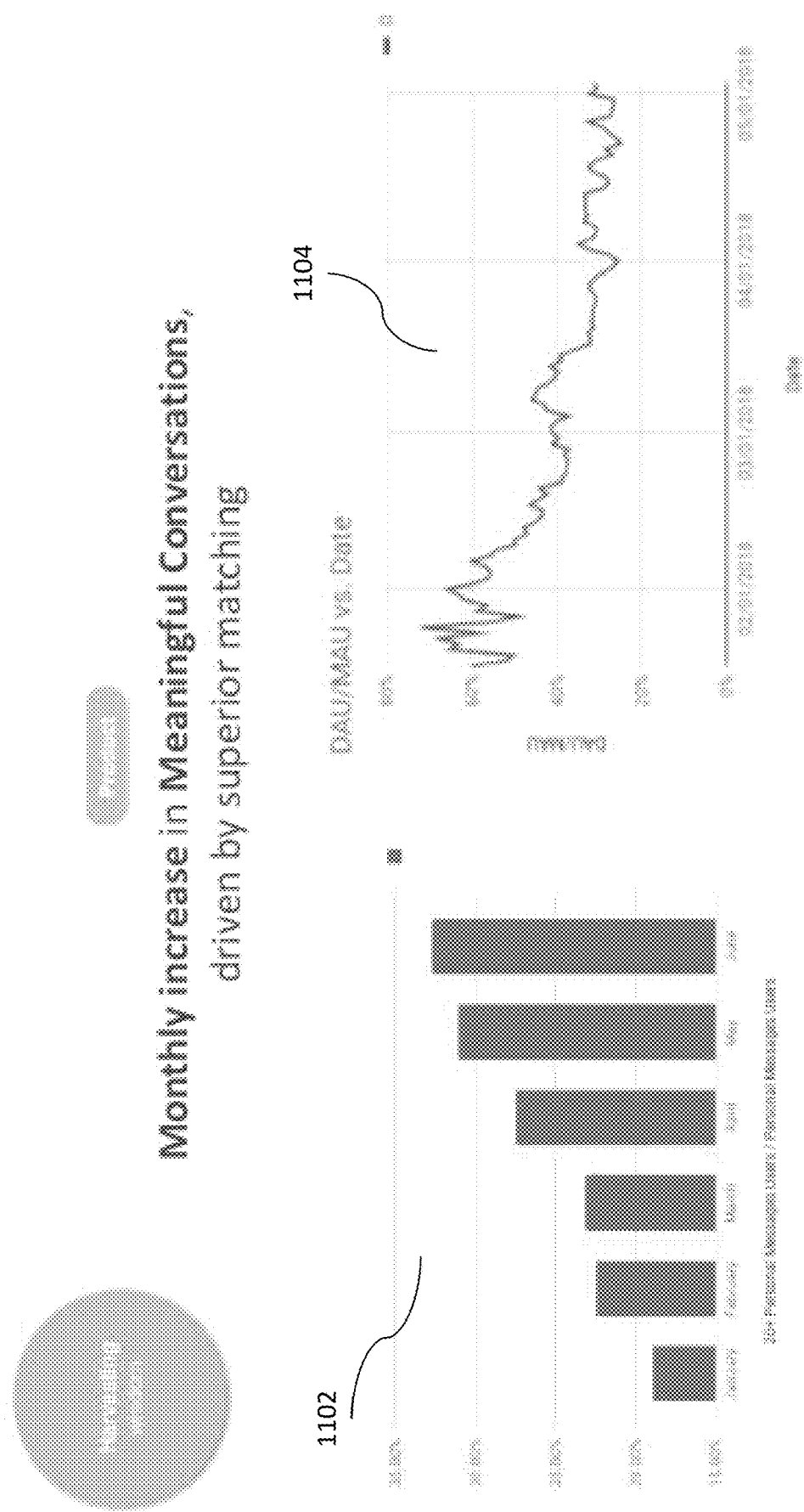
FIG. 11 shows an example of monthly increase in meaningful conversations, driven by superior matching.

FIG. 11 shows an example of monthly increase in meaningful conversations, driven by superior matching. In chart 1102, the percentage of personal message users aged 20 years or older in total personal message users is shown to increase from January to June. In chart 1104, the daily active users (DAU) to monthly active users (MAU) ratio is shown to decrease from February to May.

Figure 12:
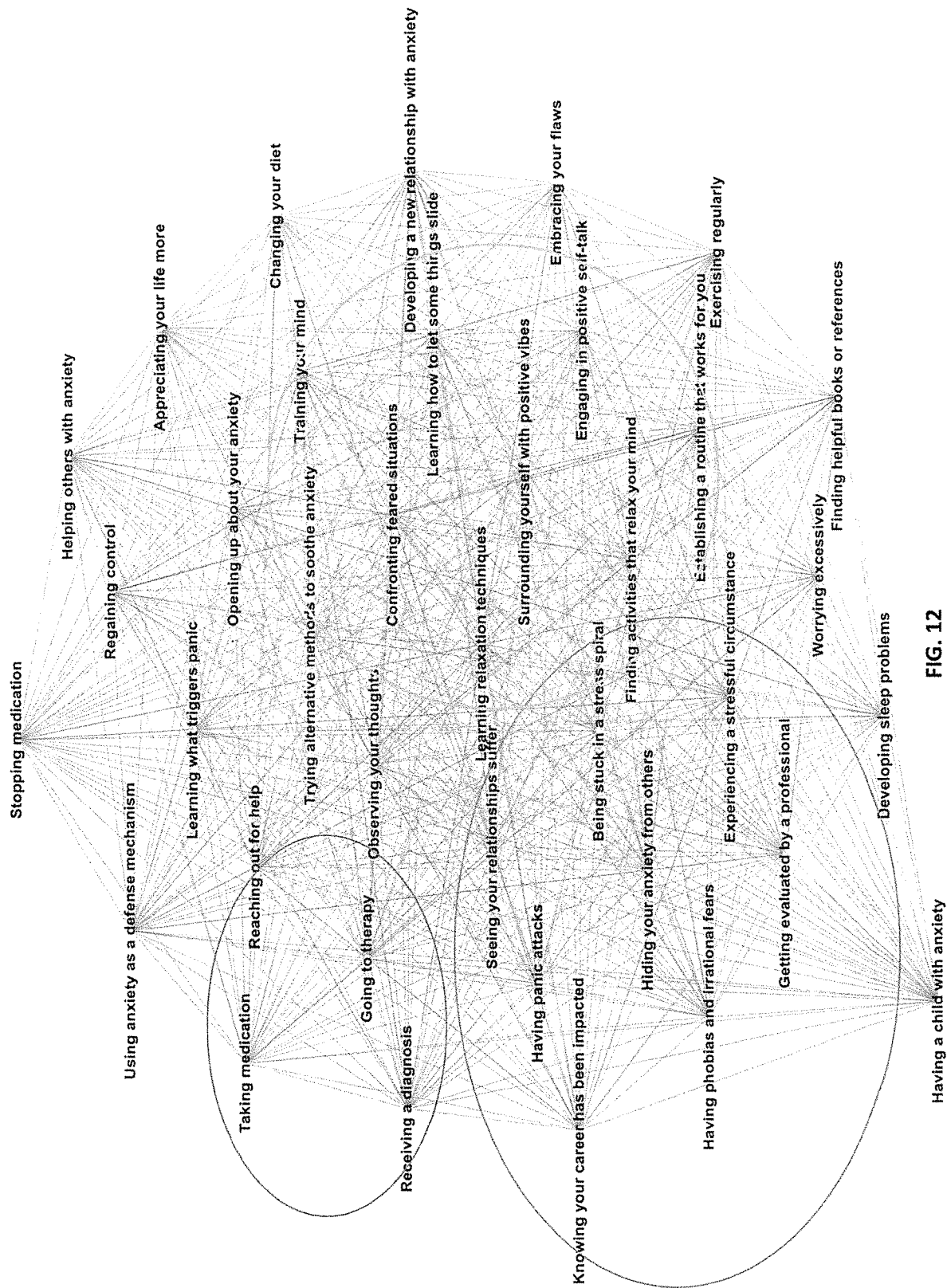
FIG. 12 shows exemplary connections among different steps regarding anxiety.

FIG. 12 shows exemplary connections among different steps regarding anxiety. In FIG. 12, the different steps may comprise stopping medication, helping others with anxiety, regaining control, using anxiety as a defense mechanism, learning what triggers panic, appreciating your life more, opening up about your anxiety, changing your diet, reaching out for help, trying alternative methods to soothe anxiety, going to therapy, receiving a diagnosis, observing your thoughts, confronting feared situations, developing a new relationship with anxiety, learning how to let something slide, learning relaxation techniques, seeing your relationship suffer, having panic attacks, surrounding yourself with positive vides, knowing your career has been impacted, being stuck in a stress spiral, engaging in positive self-talk, finding activities that relax your mind, hiding your anxiety from others, having phobias and irrational fears, establishing a routine that works for you, experiencing a stressful circumstances, exercising regularly, getting evaluated by a professional, worrying excessively, finding helpful books or references, developing sleep problems, a child with anxiety, among others. The different steps may be interconnected in a multiple of ways or possibilities.

Figure 13:
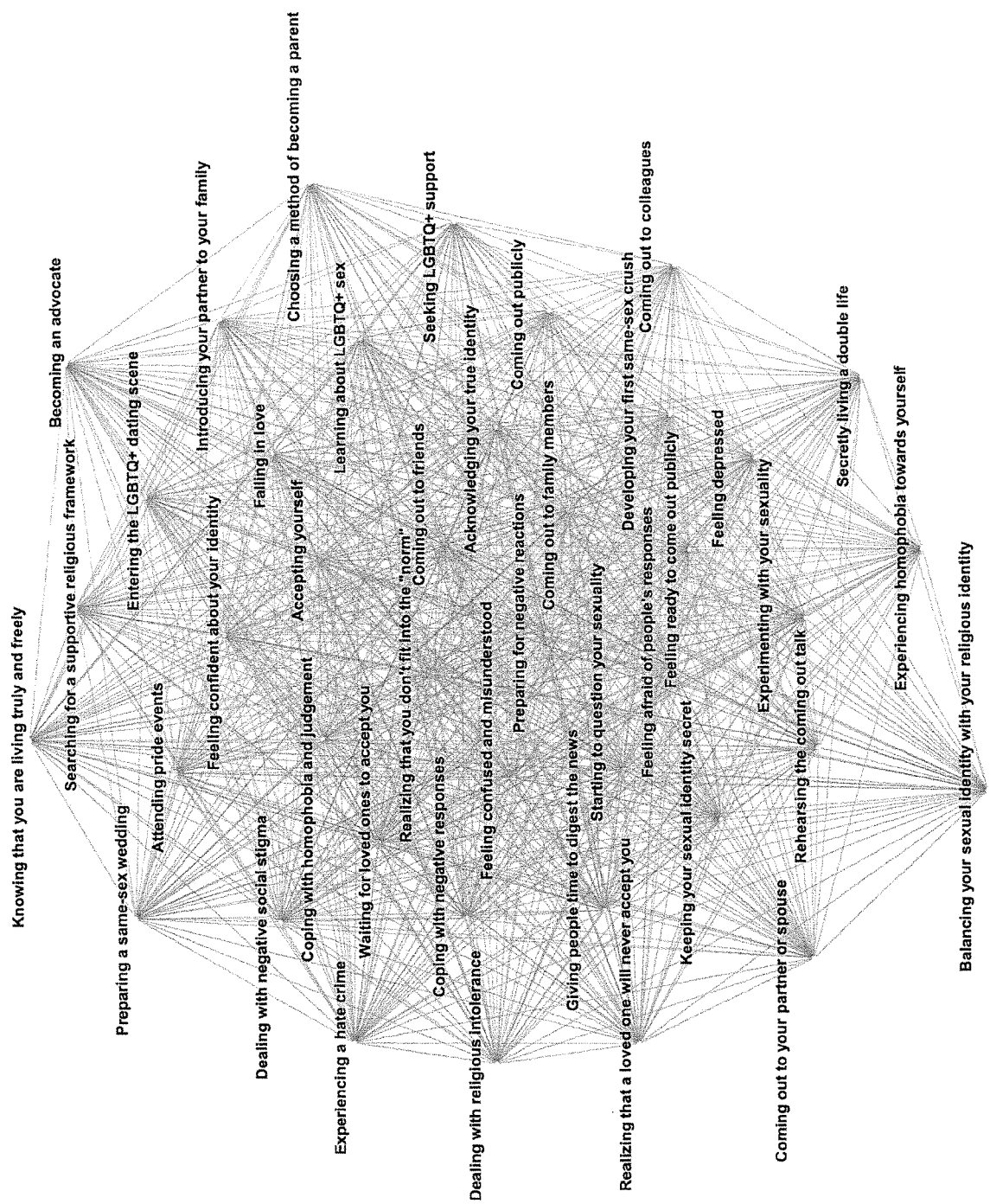
FIG. 13 shows exemplary connections among different steps regarding lesbian, gay, bisexual, and transgender ("LGBTQ")

FIG. 13 shows exemplary connections among different steps regarding lesbian, gay, bisexual, and transgender ("LGBTQ"). In FIG. 13, the different steps may comprise knowing that you are living truly and freely, searching for a supportive religious framework, becoming an advocate, preparing a same sex wedding, entering the LGBTQ dating scene, attending pride events, feeling confident about your identity, introducing your partner to your family, dealing with negative social stigma, falling in love, coping with homophobia and judgement, accepting yourself, choosing a method of becoming a parent, waiting for loved ones to accept you, learning about LGBTQ sex, realizing that you do not fit into the norm, coming out to friends, experiencing hate crime, coping with negative responses, seeking LGBTQ support, dealing with religious intolerance, feeling confused and misunderstood, acknowledging your true identity, preparing for negative reactions, coming out to family members, coming out publicly, giving people time to digest the news, starting to question your sexuality, realizing a loved one will next accept you, feeling afraid of people's responses, developing your first same sex crush, coming out to colleagues, feeling ready to come out publicly, keeping your sexual identity secret, feeling depressed, coming out to your partner or spouse, experimenting with your sexuality, rehearsing that coming out talk, secretly living a double life, experience homophobia towards yourself, balancing your sexual identity with your religious identity, among others. The different steps may be interconnected in a multiple of ways or possibilities.

Figure 14:
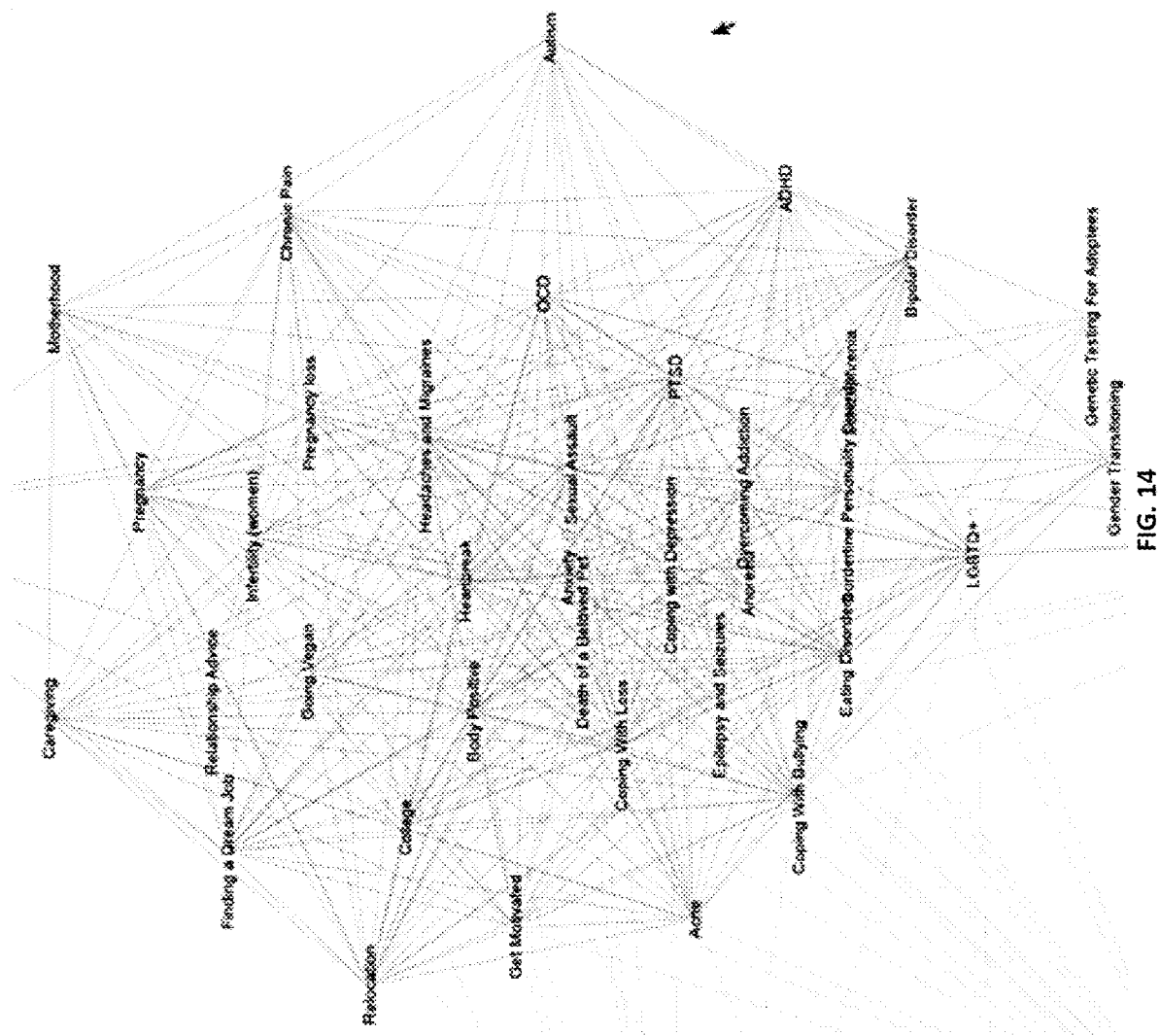
FIG. 14 shows exemplary connections provided by predictive methods.

FIG. 14 shows exemplary connections provided predictive methods. In FIG. 14, the connections may be represented by the solid lines. The connections may be discovered by artificial intelligence predictive methods. The connections may demonstrate subsequent experiences. The connections may predict subsequence steps at an accuracy of at least 2, 3, 4, 5, 6, 7, 8, 9, or 10 times more accurate than traditional methods. For instance, the subsequent experience of college may be anxiety, subsequent experience of finding dream job may be relationship advice, and the subsequent experience of caregiving may be body positive. In another example, the subsequent step of choosing a pediatrician may be recovering from birth, the subsequent step of coming out to friends may be coming out to colleagues, and the subsequent step of balancing studies and personal life may be worrying excessively. In FIG. 12, the connections may be demonstrated among events such as caregiving, motherhood, pregnancy, relationship advice, infertility, going vegan, pregnancy loss, chronic pain, autism, dream job, college, body positive, heartbreak, headaches and migraines, ADHD, OCD, relocation, get motivated, acne, coping with bullying, death of a beloved pet, anxiety, sexual assault, coping with depression, epilepsy and seizures, overcoming addiction, eating disorder, LGBTQ, gender transitioning, genetic testing for adoptees, and bipolar disorder.

Figure 15:
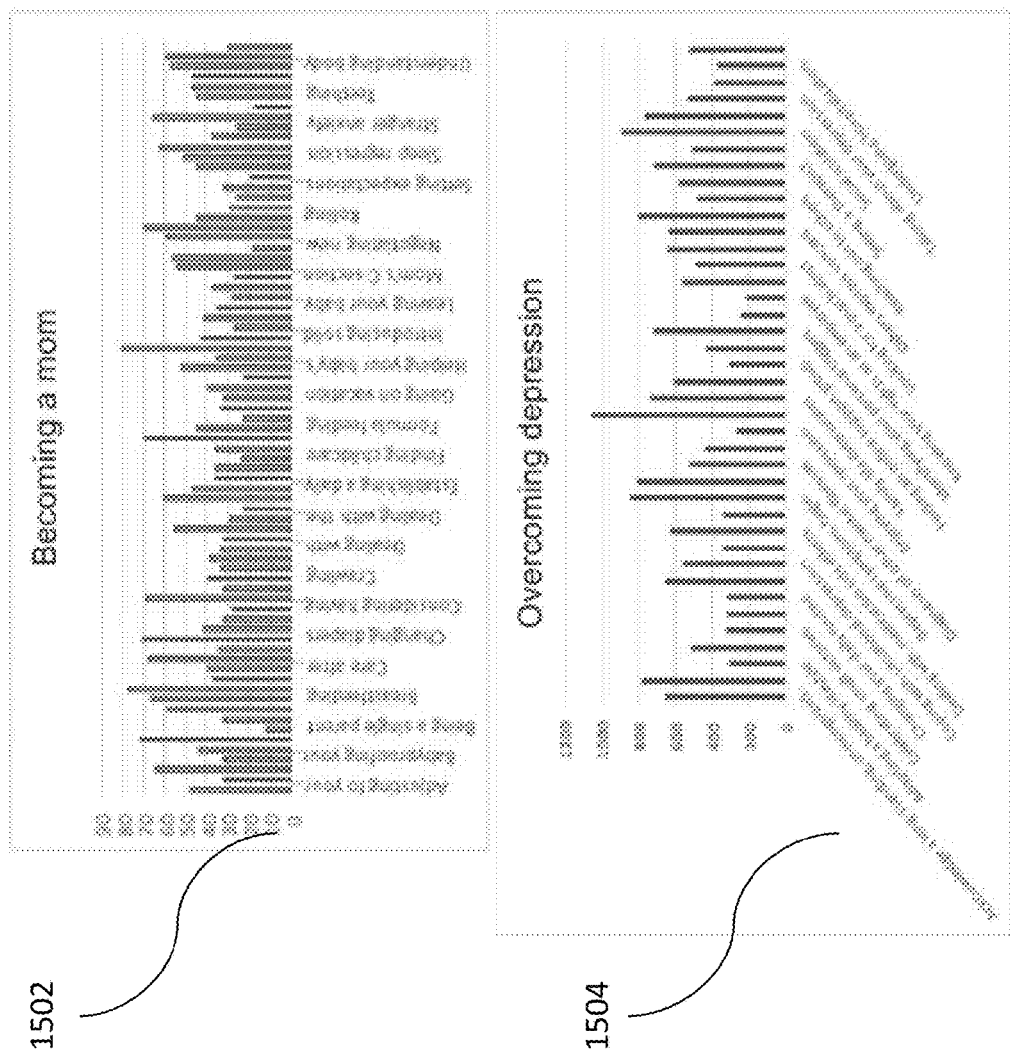
FIG. 15 shows an example of life's most intense junctions.

FIG. 15 shows an example of life's most intense junctions. In each chart 1502 or 1504, the bar shape in the chart may represent the intensity of each step in each life event. For instance, in chart 1502, the intensity of breastfeeding may be around 80 in the life event of becoming mom, and in chart 1504, the intensity of seeing a therapist is around 700 in the life event of overcoming depression.

Figure 16:
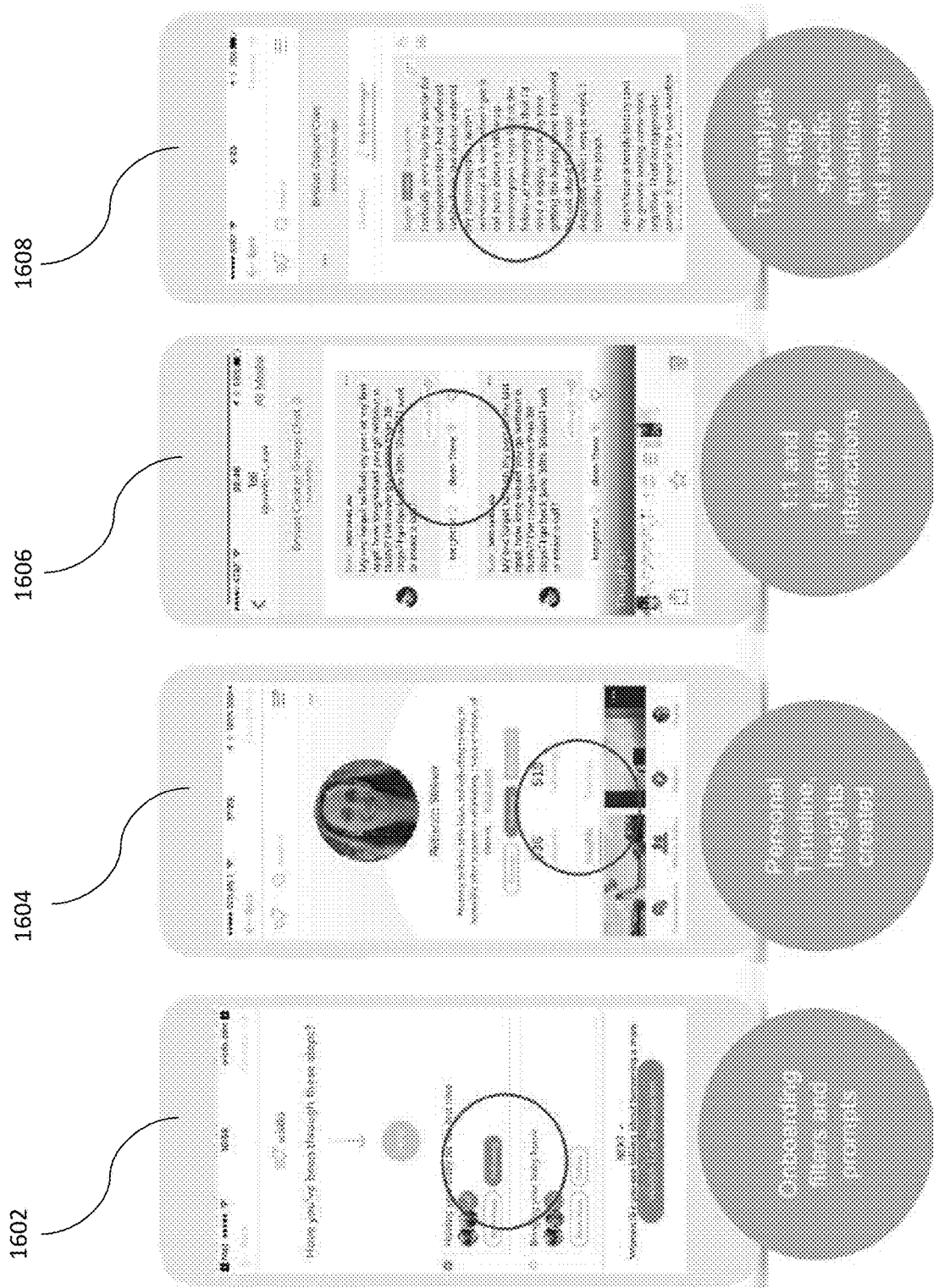
FIG. 16 shows an example of finding someone "have been" to becoming a mom.

FIG. 16 shows an example of finding someone "have been" to becoming a mom. In FIG. 16, determining where users "have been" and where they are heading may comprise onboarding filters and prompts 1602, creating personal timeline and insights 1604, 1:1 and 1:group interactions 1606, and test analysis regarding step specific questions and answers 1608. There may be step specific questions to be answered by the user, for example: what is a tip you would give to working moms of young kids; anyone have a preemie; is the baby supposed to be rolling over, or trying to pull up; my 9 year old is asking about sex, and is there a good sex education book I should use; I've tried everything to help put my four year old to sleep, including giving her so much orange foods she had an orange tinge. Anyone got a tip; I was taken by surprise the other day by the first sex-ed question (how did the baby get into your tummy?) from my 4 year old! What should I say; what helped you gals through the transition of becoming a new mommy; is there anyone in Colorado that is a stay at home mom; when did you all start your babies on solids; should I get my son a phone; and what are the pros and cons.

If the life event is overcoming depression, the step specific questions to be answered by the user may comprise: do you think women are more likely than men to neglect their mental state; summer, did you try homeopathic treatments that can soothe yours attacks; anxiety can definitely encourage depressive episodes for me so I feel your pain; has anyone here ended up with a cognitive impairment due to ECT; has anyone found Depakote to cause anger side effects; how do you all help a spouse understand that I'll never "get over it", and all I can do is manage the depression/anxiety; TMS didn't work. Pretty nervous about it but considering ECT. Does anyone have experience with it; so has anyone here been this bad and found your way back again? How; and sometimes I put on some loud music and either sing along or dance it out. It distracts and shifts moods sometimes and is good for bouncing back.

Figure 17A:
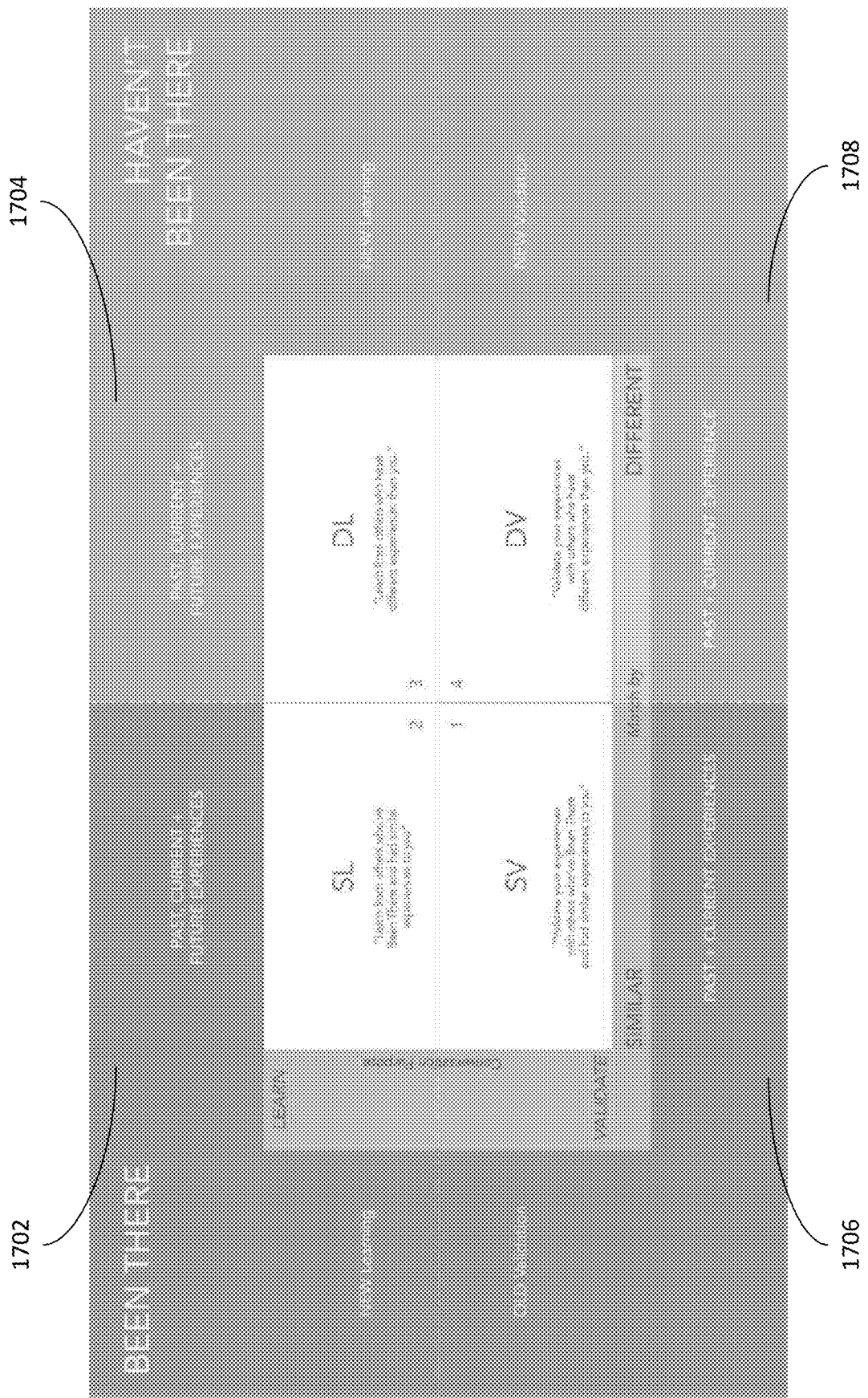
FIG. 17A shows exemplary methods used by the user matching platform, in accordance with some embodiments.

FIG. 17A shows exemplary methods used by the user matching platform, in accordance with some embodiments. Four different methods, 1702, 1704, 1706, and 1708, are presented in FIG. 17. The method 1702 may be related to "similar/learn" (SL), which means the user may learn from others who have been there and had similar experiences to the user. The method 1702 may comprise the following steps: matching the user with people who have similar experiences with the user, determining that the purpose of the conversation is to learn something about the new experiences, determining that the match has been there at the same steps as the user, and determining that the conversation is dealing with past, current and future experiences. The method 1704 may be related to "different/learn" (DL), which means the user may learn from others who had different experiences from the user. The method 1704 may comprise the following steps: matching the user with people who have different experiences with the user, determining that the purpose of the conversation is to learn something about the new experiences, determining that the match has not been there at the same steps as the user, and determining that the conversation is dealing with past, current and future experiences. The method 1706 may be related to "similar/validate" (SV), which means the user may validate his/her experiences with others who have been there and had similar experiences to the user. The method 1706 may comprise the following steps: matching the user with people who have similar experiences with the user, determining that the purpose of the conversation is to validate the past experiences of the user, determining that the match has been there at the same steps as the user, and determining that the conversation is dealing with past and current experiences. The method 1708 may be related to "different/validate" (DV), which means the user may validate his/her experiences with other who have had different experiences than the user. The method 1708 may comprise the following steps: matching the user with people who have different experiences with the user, determining that the purpose of the conversation is to validate the past experiences of the user, determining that the match has not been there at the same steps as the user, and determining that the conversation is dealing with past and current experiences.

FIG. 17B shows an example of conversations coded by type. In FIG. 17B, 75 pages of a Breast Cancer group chat are analyzed. The user matching platform may categorize what type of Conversation Purpose and Match (SV/SL/DL/DV) are in the group chat. The user matching platform may count the instances of each type and recorded it below in the ASK columns. The user matching platform may also count/record how many Answers/Replies these different types of questions may generate (this is shown in the ANSWER column). The conversations may include greetings, introductions, comments, statements and general replies that aren't tied to the type of Conversation Purpose and Match. These may be recorded in the OTHER category.

Figure 18:
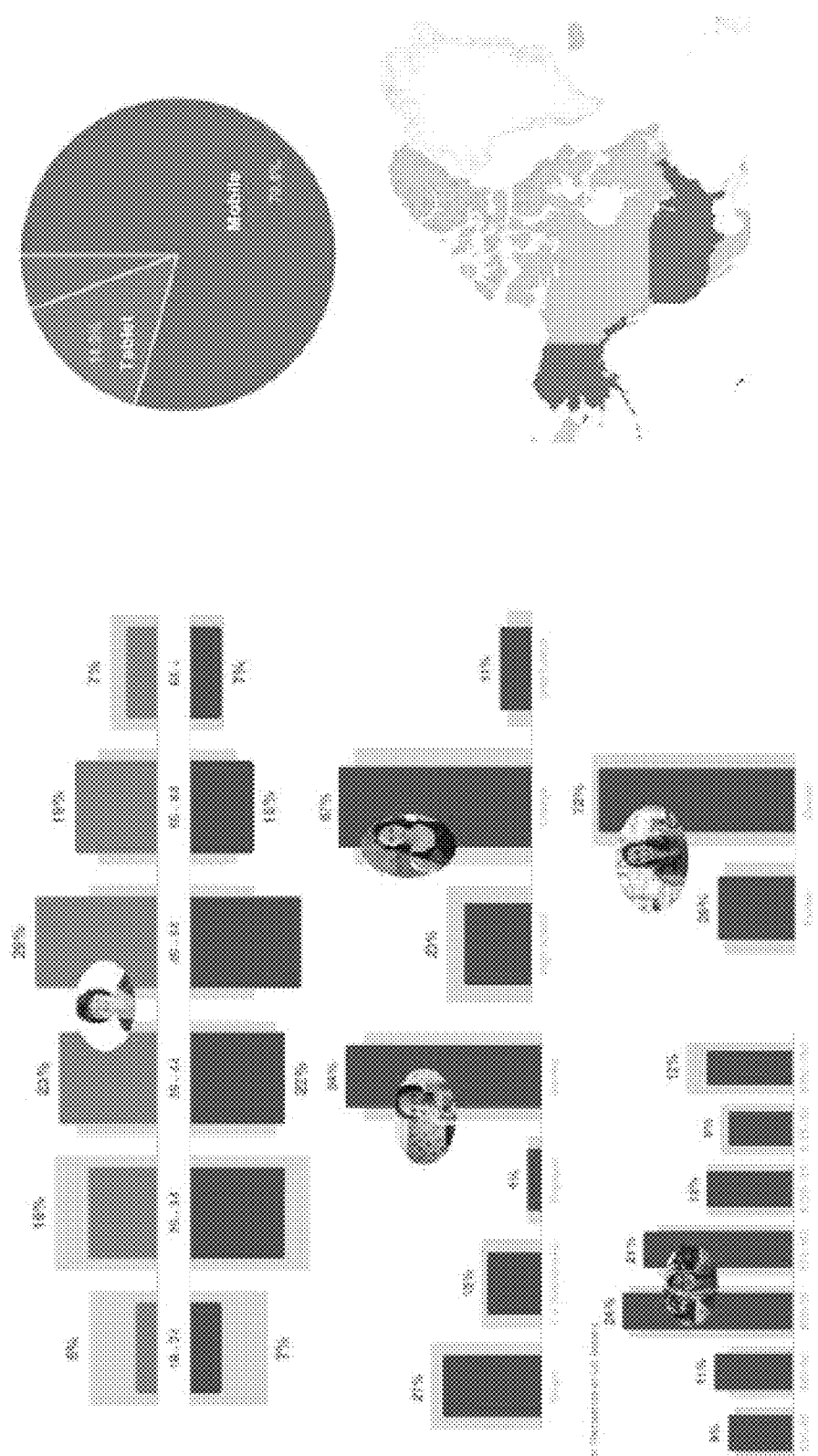
FIG. 18 shows an example of user base.

FIG. 18 shows an example of user base. The users may be largely from US college educated women, who are married, in their middle age, and hold average income.

FIG. 19 shows an example of emotional states of the users. The matrix may denote the key emotional state and drive for the different personas.

FIGS. 20A-20B show an example of persona sensitive notification cycle for Kirsten. In the FIGS. 20A-20B, Kirsten may respond best to notifications that feed her underlying intent and mirror her emotional state; and Kirsten may respond best to prompts that model certain behaviors demonstrated in the figures.

Computer Control Systems

Figure 21:
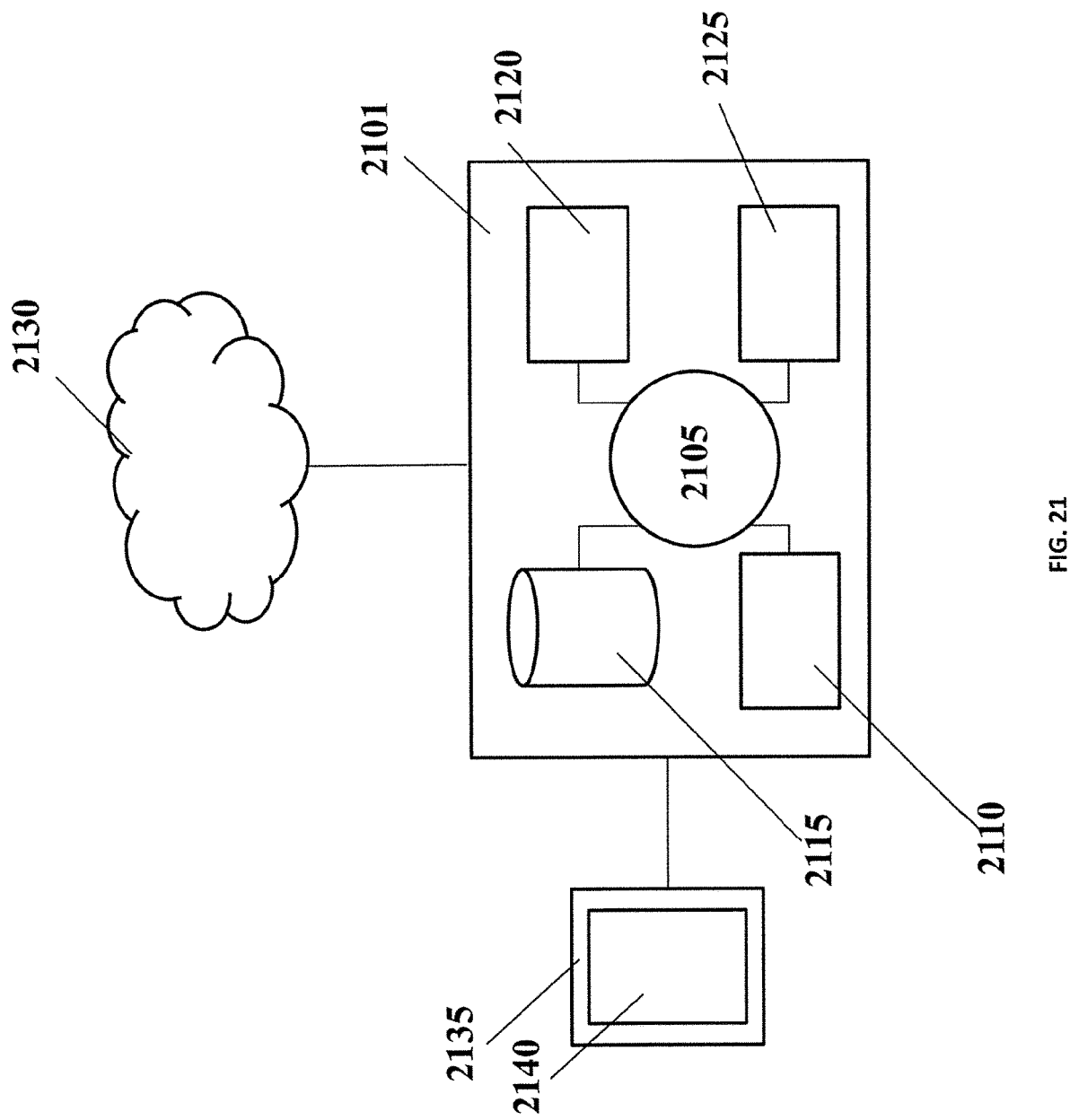
FIG. 21 shows a computer control system that is programmed or otherwise configured to implement methods provided herein.

The present disclosure provides computer control systems that are programmed to implement methods of the disclosure. FIG. 21 shows a computer system 2101 that is programmed or otherwise configured to implement a method for assisting a user in user matching. As previously described, such events may be related to significant life transitions (SLTs), for example, going to college, getting married, having children, starting a business, getting divorced, retirement, relocation, or diagnosed with a terminal illness, among others. The computer system 2101 can store and/or execute software that performs an algorithm for processing user input, identifying an event from the user input, determining relevant milestone(s) and need(s) associated with the event, and matching user with someone who has experienced, is experiencing, or is likely to experience the same life event. The computer system 2101 can be an electronic device of a user or a computer system that is remotely located with respect to the electronic device. The electronic device can be a mobile electronic device.

The computer system 2101 includes a central processing unit (CPU, also "processor" and "computer processor" herein) 2105, which can be a single core or multi core processor, or a plurality of processors for parallel processing. The computer system 2101 also includes memory or memory location 2110 (e.g., random-access memory, read-only memory, flash memory), electronic storage unit 2115 (e.g., hard disk), communication interface 2120 (e.g., network adapter) for communicating with one or more other systems, and peripheral devices 2125, such as cache, other memory, data storage and/or electronic display adapters. The memory 2110, storage unit 2115, interface 2120 and peripheral devices 2125 are in communication with the CPU 2105 through a communication bus (solid lines), such as a motherboard. The storage unit 2115 can be a data storage unit (or data repository) for storing data. The computer system 2101 can be operatively coupled to a computer network ("network") 2130 with the aid of the communication interface 2120. The network 2130 can be the Internet, an internet and/or extranet, or an intranet and/or extranet that is in communication with the Internet. The network 2130 in some cases is a telecommunication and/or data network. The network 2130 can include one or more computer servers, which can enable distributed computing, such as cloud computing. The network 2130, in some cases with the aid of the computer system 2101, can implement a peer-to-peer network, which may enable devices coupled to the computer system 2101 to behave as a client or a server.

The CPU 2105 can execute a sequence of machine-readable instructions, which can be embodied in a program or software. The instructions may be stored in a memory location, such as the memory 2110. The instructions can be directed to the CPU 2105, which can subsequently program or otherwise configure the CPU 2105 to implement methods of the present disclosure. Examples of operations performed by the CPU 2105 can include fetch, decode, execute, and writeback.

The CPU 2105 can be part of a circuit, such as an integrated circuit. One or more other components of the system 2101 can be included in the circuit. In some cases, the circuit is an application specific integrated circuit (ASIC).

The storage unit 2115 can store files, such as drivers, libraries and saved programs. The storage unit 2115 can store user data, e.g., user preferences and user programs. The computer system 2101 in some cases can include one or more additional data storage units that are external to the computer system 2101, such as located on a remote server that is in communication with the computer system 2101 through an intranet or the Internet.

The computer system 2101 can communicate with one or more remote computer systems through the network 2130. For instance, the computer system 2101 can communicate with a remote computer system of a user (e.g., an end user, a contributor, a curator, an entity, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2101 via the network 2130.

Methods as described herein can be implemented by way of machine (e.g., computer processor) executable code stored on an electronic storage location of the computer system 2101, such as, for example, on the memory 2110 or electronic storage unit 2115. The machine executable or machine readable code can be provided in the form of software. During use, the code can be executed by the processor 2105. In some cases, the code can be retrieved from the storage unit 2115 and stored on the memory 2110 for ready access by the processor 2105. In some situations, the electronic storage unit 2115 can be precluded, and machine-executable instructions are stored on memory 2110.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 2101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2101 can include or be in communication with an electronic display 2135 that comprises a user interface (UI) 2140 for providing, for example, a user portal for user matching. A user can view timelines, journeys, milestones, events, steps, topics, insights, forums, etc. via the portal. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2105. For example, the algorithm may be configured to process user input, identify an event from the user input, determine relevant milestone(s) and need(s) associated with the event, and match the user with people who have experienced, are currently experiencing, or likely to experience in the future the life event of the user. The algorithm may also be configured to define and classify a plurality of topics relating to those milestone(s) and need(s). The algorithm may also be configured to search and extract questions stored in one or more database(s) relating to those topics/milestone(s). The algorithm may also be configured to search and extract insights and comments stored in one or more database(s) relating to those topics or milestone(s). The algorithm may also be configured to filter the questions and insights, and match the filtered questions/insights to the user's needs/milestones. The algorithm may also be configured to sort the matched insights/questions, and provide personalized recommendations to the user based on the user's milestones, timeline and needs. The algorithm may also be configured to match the user with people who have experienced, are currently experiencing, or likely to experience in the future the life event of the user. A variety of algorithms may be performed for performing one or more user matching techniques.

EXAMPLES

These examples are provided for illustrative purposes only and not to limit the scope of the claims provided herein.

Example 1: Calculation of the Raw Scores

In this example, two scenarios are considered, and been-there been there (BB) scores are calculated.

Scenario 1: User A has indicated "Been-There" in 4 steps, and user B has indicated "Been-There" in at least 2 steps, including 2 of the steps indicated by user A. In other words, 50% of the steps are shared by users A and B. The AbsCountCoef term is set to 1 for this example. In this case, the BB raw score would be calculated as described above, such that:

$BB = 2/4 + 1 = 2/5$

Notice that the value of BB is not equal to the fraction of shared steps, and that the value of BB is independent of the number of steps taken by user B.

Scenario 2: User A has indicated "Been-There" in 8 steps, and user B has indicated "Been-There" in at least 4 steps, including 4 of the steps indicated by user A. In other words, 50% of the steps are shared by users A and B. The AbsCountCoef term is set to 1 for this example. In this case, the BB raw score would be calculated as described above, such that:

$$BB = \frac{4}{8+1} = 4/9$$

Notice that the value of BB is again not equal to the fraction of shared steps, and that the value of BB is independent of the number of steps taken by user B. However, notice that the score is also not the same as the BB score in scenario 1, even though the fraction of shared steps is the same. In fact, it is larger, because more total steps are shared by users A and B.

Example 2: User Parameters

Figure 22:
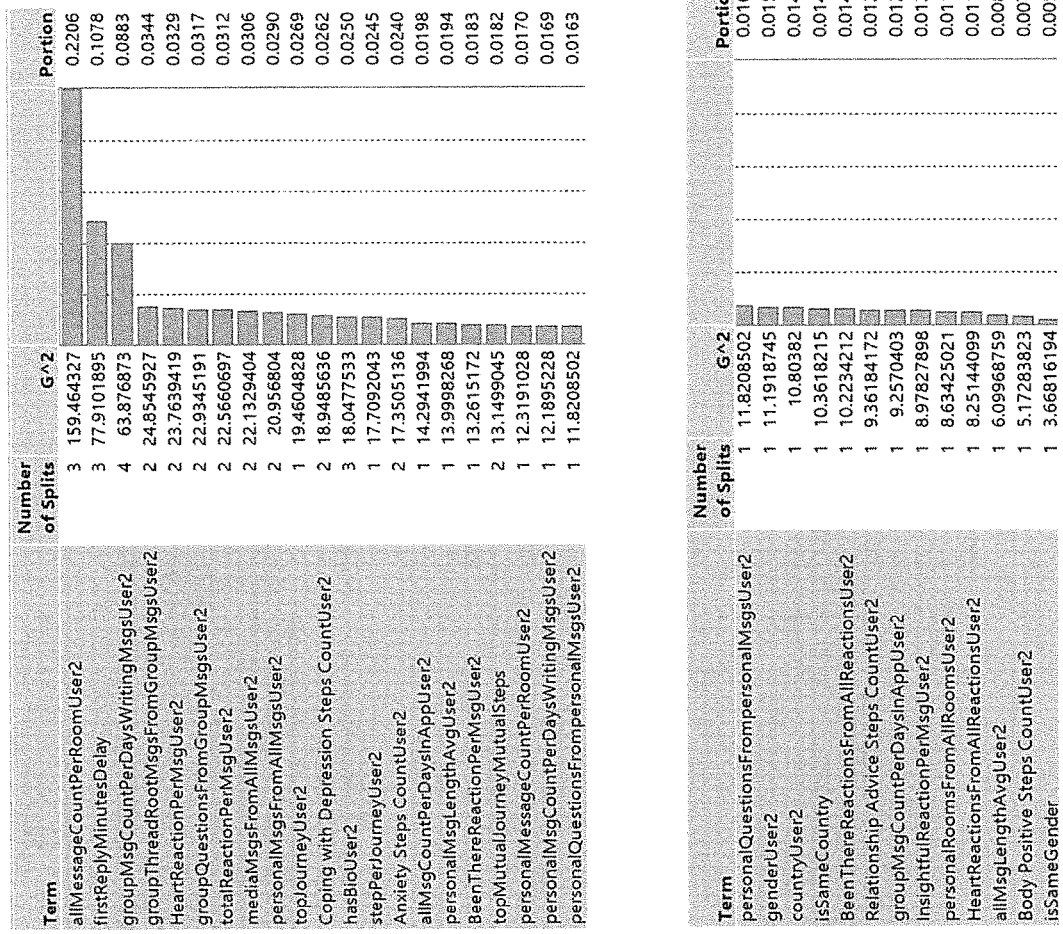
FIG. 22 illustrates the statistics of the match success of a match between a second user and a first user as a function of a plurality of features.

In one example, while using the application or platform, users may have created profiles, followed journeys, events and timelines, joined groups, messaged other users, and replied to other users. Users may also have indicated their anxiety, how they coped with ailments including depression, and asked questions. Any one or more of these may be a measure of how good a match is. To probe this, match success, as determined by conversation progression, can be determined based on a variety of parameters. User parameters, or features, analyzed may include the average of the total number of messages a user posted per chat room that the user is active in, the typical amount of time it takes the user to reply to a message in minutes, the average number of messages posted in a chat room per day, the total number of threads the user started, the total number of heart reactions from the user, the total number of questions the user posed to a group, the total number of times the user reacted to another user, the total number of media messages as a fraction of all messages the user sent, the total number of personal messages as a fraction of all messages the user sent, the most active journey the user is active in, the number of steps the user has traversed with regards to coping with depression, whether or not the user has filled out a biography or profile information, the typical number of steps the user has completed per journey, the typical number of steps the user indicates feeling anxious about, the typical number of messages sent in the app per day, the average length of personal messages sent by the user, the total number of Been-There reactions submitted by the user, the total number of mutual steps the user shares with a matched user in the journey for which they were matched, the typical number of messages the user wrote on days the user wrote messages, the total number of personal questions the user asked in response to personal messages, the gender of the user, the country the user resides in, whether a matched user resides in the same country as the user, the portions of all the user's reactions which are of the type "Been-There", the total number of relationship advice steps the user has traversed, the total number of group messages the user participated in per day the user was logged into the app, the typical number of insightful reactions the user has for each user they are matched with, the number of personal rooms the user is in, the proportion of the user's reactions which are heart reactions, the typical message length of messages written by the user, the total number of body positive steps the user has traversed, and whether or not the user is the same gender as the user they are interacting with. These were all calculated from the perspective of user B, or the user who was recommended as the match. Features may be compiled and arranged based on the match success of matches with such features, A G-test can be implemented to determine how valuable the user is as a match. In general, a higher $G^2$ value indicates better value as a match. In other words, features with higher $G^2$ values are more indicative of how good the match is compared to features with lower $G^2$ values. Examples of such data are shown in FIG. 22. In this data set, the average of the total number of messages a user posted per chat room that the user is active in was most indicative of how good that user is as a match suggestion. In this example, the average of the total number of messages the user posted per chat room that the user is active in was the most predictive of match success.

Example 3: Thread Initiators vs. Repliers

While using the application or platform, users can initiate and reply to threads to message and respond to other users. The methods described herein can be used to determine if a match was more successful or less successful, based on a thread initiator or a thread replier that was suggested as user B. Here, thread initiators are users who frequently initiate threads, and thread repliers are users who frequently reply to threads initiated by others.

Figures 23A, 23B, 23C:
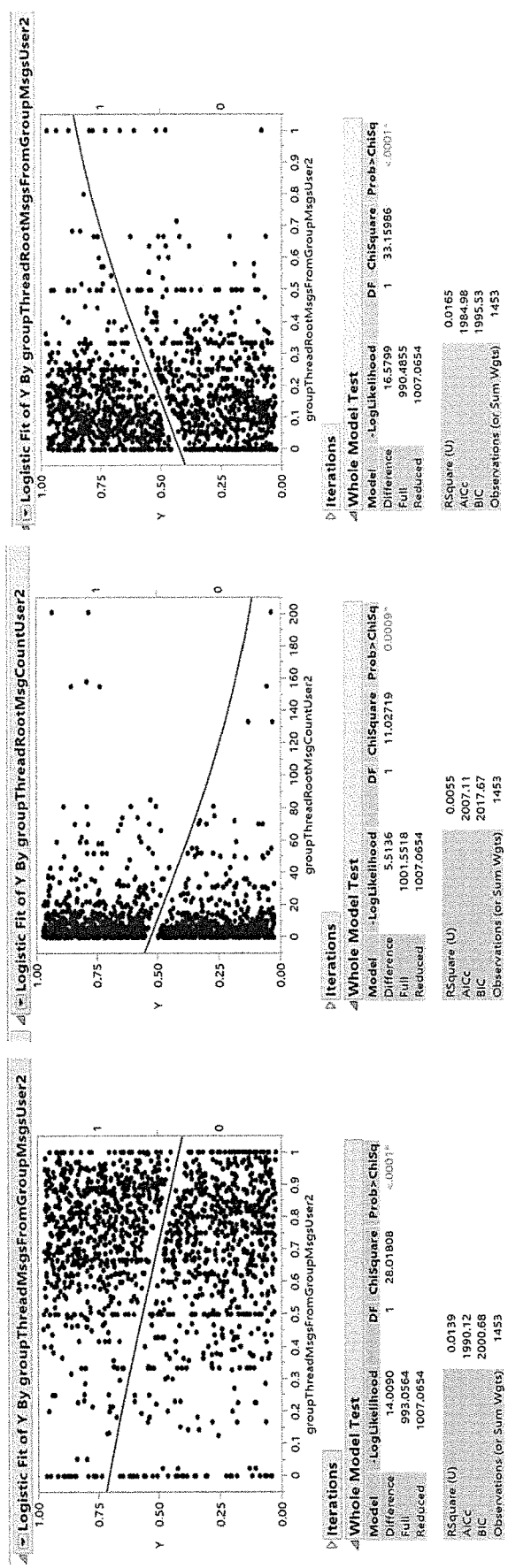

Data for each user can be plotted as the success of matches involving that user as a function of the average number of threads the user replied to (e.g. FIG. 23A), the closeness of a user as a match versus the total number of threads the user started (e.g. FIG. 23B), and the closeness of a user as a match versus the average number of threads the user started (e.g. FIG. 23C). A chi-squared analysis can be performed to determine closeness of match based on each horizontal axis parameter. In this example, the average number of threads the user started was most indicative of a successful match. In other words, users who started more threads on average in groups they were part of were more valuable as matches for other users, than users who started fewer threads on average.

Example 4: Top Journey

In this example, the platform can determine which users are more valuable to each other if their top journey is the same, where the top journey is the major journey or life event they are going through at the moment. The platform can also determine know if this metric is the same for each journey.

To measure the above, for a plurality of users, the platform can count the number of worst conversations and best conversations, where the conversations were between two users sharing the same top journey. The platform can tally the total number of conversations, total number of worst conversations, total number of top conversations, and the percentage of conversations which were top conversations, etc. In the above method, a higher percentage of conversations which are top conversations is indicative that the journey for which the metric is calculated has a higher user matching success rate when both users share the journey as their top journey. An example of the data is shown in FIG. 24, which indicates that the heartbreak journey relies heavily on the users sharing the journey as a top journey for a good match, while the body positive journey relies least heavily on the users sharing the journey as a top journey for a good match.

Example 5: Role of Gender in Determining Goodness of Match

Figure 25:
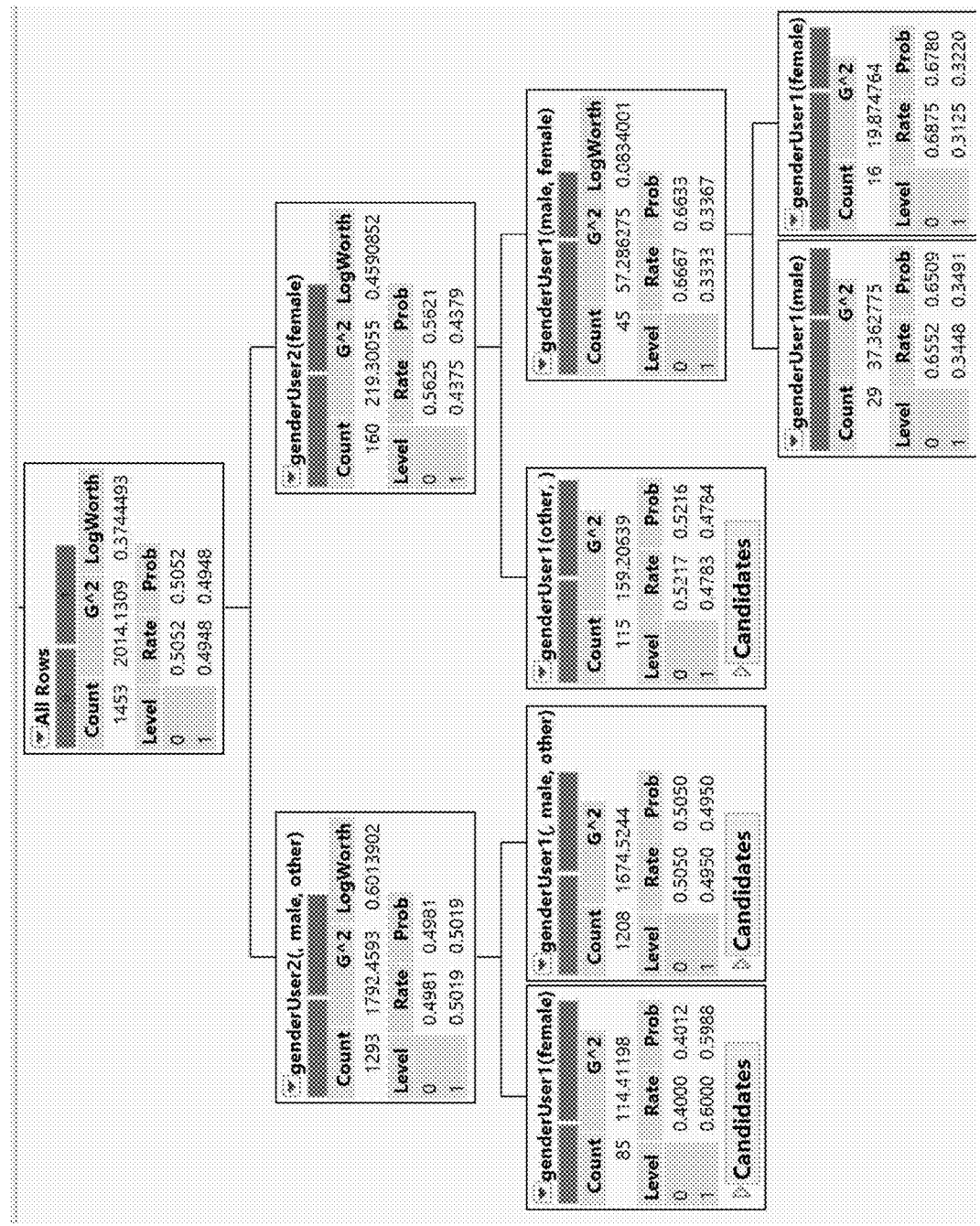
FIG. 25 illustrates conversation initiation and reply statistics based on user gender.

In this example, the platform can determine whether male or female users were more valuable when proposed as a match to a different user as measured by initiation of conversations. To this end, for users using an app implemented with one or more of the matching algorithms described herein, the platform can tally the number of male and female users which were recommended as a match, as well as the genders of the users they were matched to. The platform can tally the numbers and average lengths of such conversations, and noted who initiated each conversation. The platform can apply a chi square analysis, and determine that conversations initiated by a female and accepted by a male were twice as valuable than conversations initiated by a male and accepted by a female. The data for this example is depicted in FIG. 25.

Example 6: Role of a Completed Biography in Determining Goodness of Conversation In this example, the platform can determine whether the recommended user had completed a biography associated with their account in an application or platform. A method as described herein can be used to recommend the user to another user. Here, the platform can determine if completion of a biography is associated with matching of conversation between the two users.

To this end, the platform can assign each user B who was recommended as a match for one or more users A a score of 1 or 0, where 1 indicated that user B had completed the biography, and 0 indicated that user B had not completed the biography. Additionally, conversations that user B was involved in with one of users A were assigned a score of 1 or 0, where 1 indicates a good conversation and 0 indicates a bad conversation.

Figure 26:
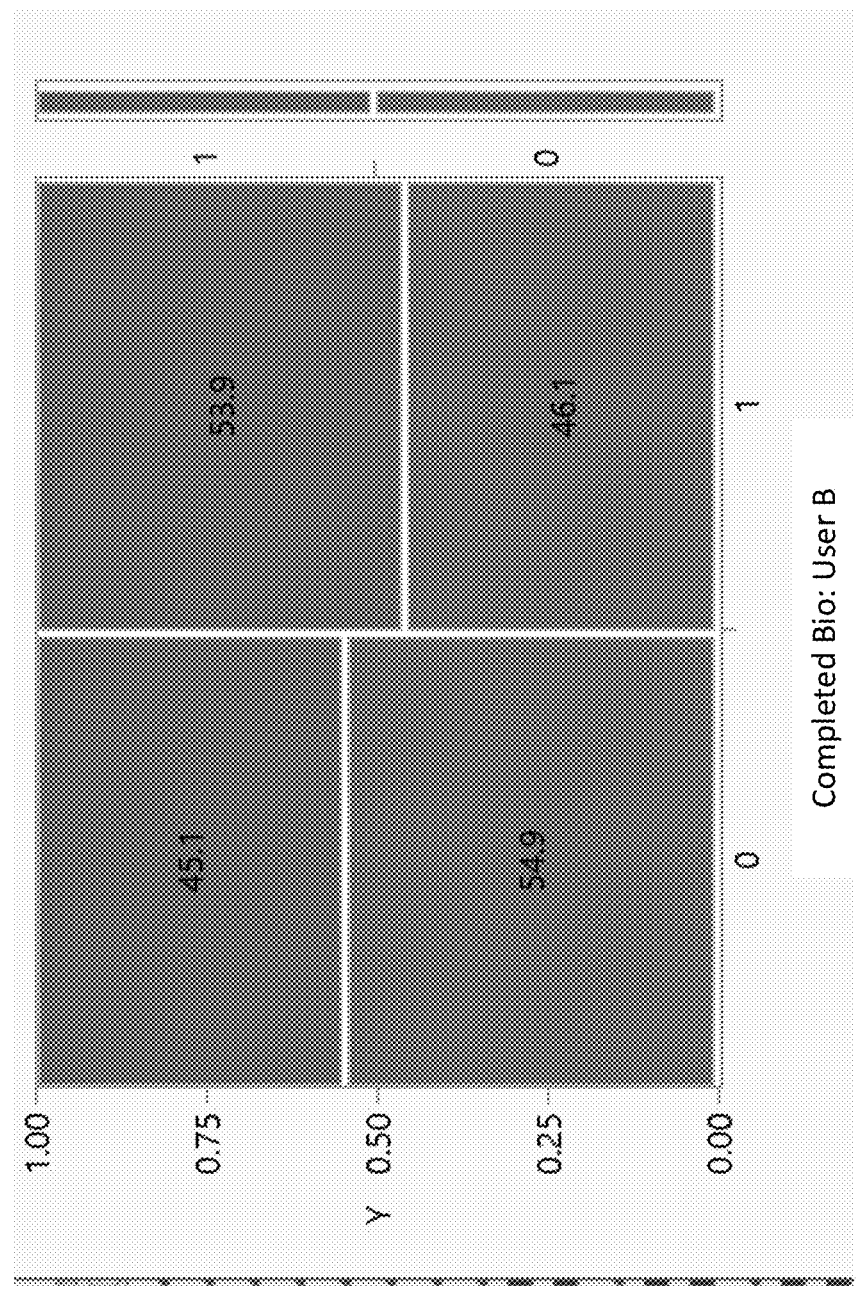
FIG. 26 illustrates an example of the relationship between the completion of a biography and the closeness of conversation between the two users.

These values can be represented in a mosaic plot. An example of the data is shown in FIG. 26. The X axis indicates whether or not the user B has a biography completed. The Y axis ranges from 0 to 1, and represents the fraction of the total number of conversations. The numbers inside each square indicate the percentage of good conversations for a given user B. The red boxes indicate bad conversations, and the red boxes indicate good conversations. For example, for users B with a biography completed, 53.9 percent of the conversations were good, based on the data set used.

In this example, the platform can determine that user B completing a biography is significantly linked to a good conversational outcome.

Example 7: Role of User Country in Determining Closeness of Conversation

In this example, the platform can determine the country of residence of the recommended user in an application or platform. A method as described herein can be used to recommend a user to another user. Here, the platform can determine if the country of residence may be associated with matching of conversation between the two users.

To this end, the platform can determine for a plurality of users B, who had been recommended to users A, what their countries of residence were, etc. Additionally, conversations that users B were involved in with one of users A may be assigned a score of 1 or 0, where 1 indicated a good conversation and 0 indicated a bad conversation.

Figure 27:
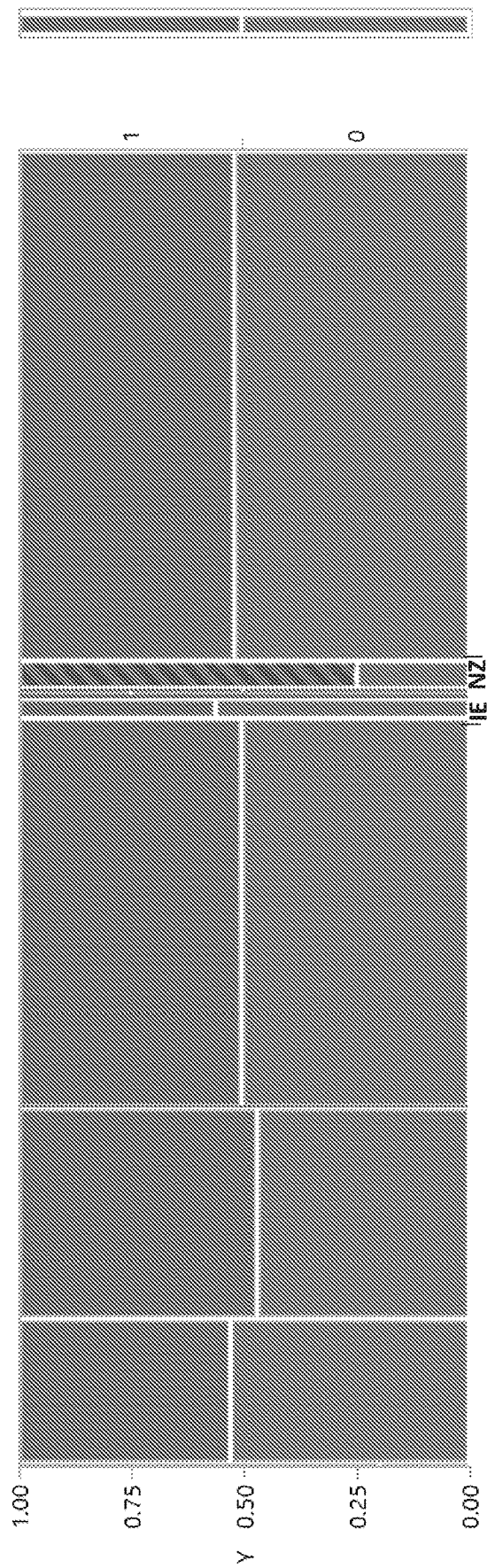
FIG. 27 illustrates the relationship between country of residence of the recommended user in an application or platform wherein a method described herein was used to recommend the user to another user was and the goodness of conversation between two users.

These values can be represented in a mosaic plot, as shown in FIG. 27. The X axis indicates the country of origin of the users B, and includes United Arab Emirates, Australia, Canada, Great Britain, Ireland, New Zealand, the United States, and other countries. The Y axis ranges from 0 to 1, and represents the fraction of the total number of conversations. The red boxes indicate bad conversations, and the red boxes indicate good conversations.

From the data in this example, the platform can determine that for users in most regions, country of residence has little impact on goodness of conversation. However, the platform can also determine that for users B in a certain region (e.g. New Zealand (NZ)), there may be significantly more good conversations by percentage than for users B in other countries.

Example 8: Heart Reactions are Linked to Top Users

Here, the platform can determine whether top users could be predicted by the types of reactions they indicated in an app. A method as described herein can be used to recommend a user to another user. To this end, the platform can determine the match success from matching a user (on a scale of 0 to 1) compared with four metrics, where the four metrics were average number of total reactions the user indicated per message, the average number of heart reactions the user indicated per message, the average number of Been-There reactions the user indicated per message, and the total number of insightful reactions the user indicated per message.

Figure 28:
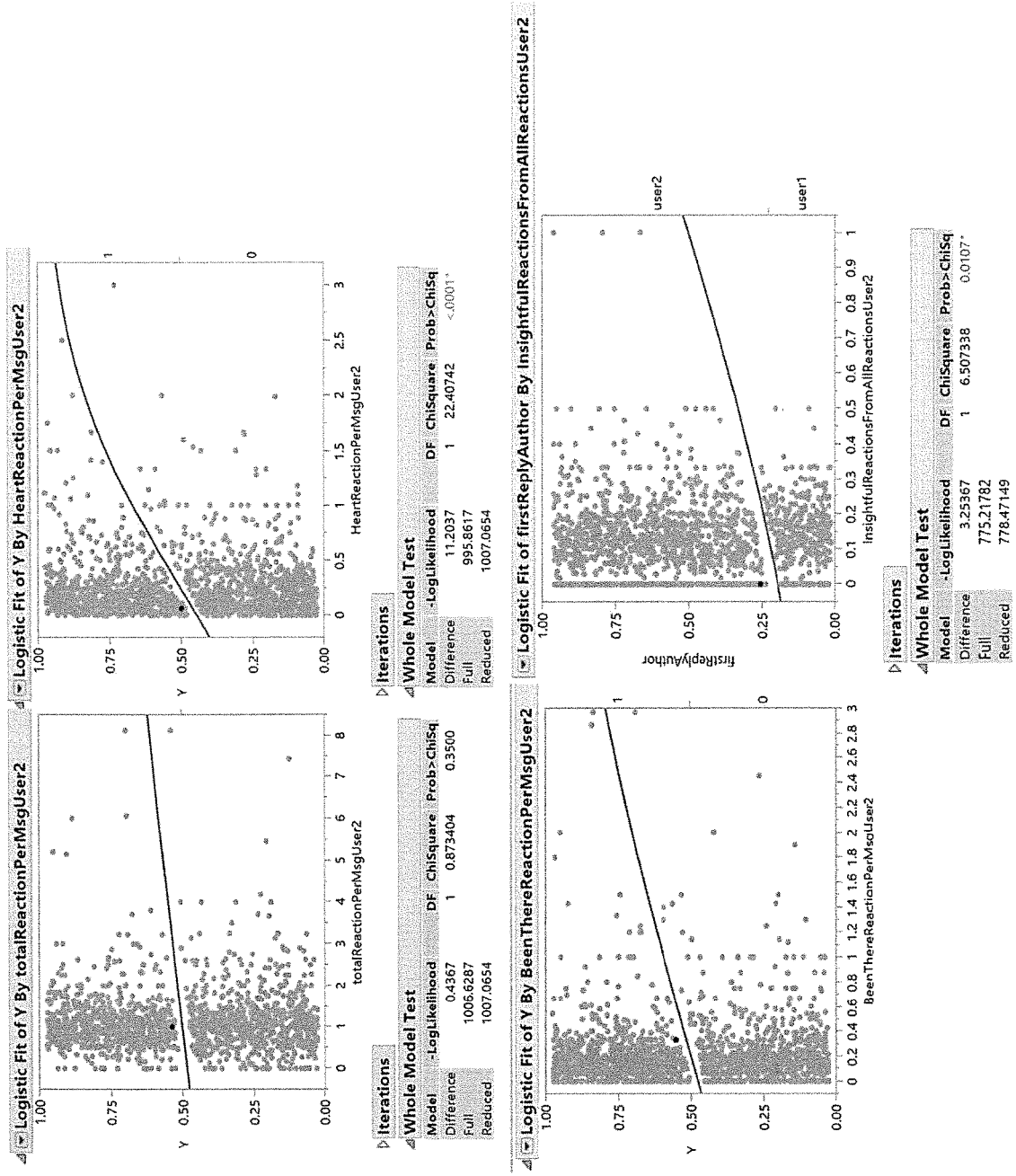
FIG. 28 illustrates the quality of a user as a function of four metrics.

The data can be plotted, and a Chi Squared analysis can be applied, and a logistic fit can be fitted to the data and drawn onto the plots, as shown in FIG. 28. Here, a steeper line of fit indicates that as the metrics on the x axis increase, the quality of the user also increases. For example, the data may indicate that users who use the heart reaction more often on average are more likely to be a top user than a user who uses the heart reaction less often on average.

FIG. 22 illustrates the statistics of the match success of matches of a second user to a first user, or how valuable the second user is as a match. Included features may include, for example:
  allMessageCountPerRoomUser2=the average of the total number of messages a user posted per chat room that the user is active in,
  firstReplyMinutesDelay=the typical amount of time it takes the user to reply to a message in minutes,
  groupMsgCountPerDaysWritingMsgsUser2=the average number of messages posted in a chat room per day,
  groupThreadRootMsgsFromGroupMsgsUser2=the total number of threads the user started in a group,
  HeartReactionPerMsgUser2=the total number of heart reactions from the user,
  groupQuestionsFromGroupMsgsUser2=the total number of questions the user posed to a group,
  totalReactionPerMsgUser2=the total number of times the user reacted to another user,
  mediaMsgsFromAllMsgsUser2=the total number of media messages as a fraction of all messages the user sent,
  personalMsgsFromAllMsgsUser2=the total number of personal messages as a fraction of all messages the user sent,
  topJourneyUser2=the most active journey the user is active in,
  CopingwithDepressionStepsCountUser2=the number of steps the user has traversed with regards to coping with depression,
  hasBioUser2=whether or not the user has filled out a biography or profile information,
  stepPerJourneyUser2=the typical number of steps the user has completed per journey,
  AnxietyStepsCountUser2=the typical number of steps the user indicates feeling anxious about,
  allMsgCountPerDaysInAppUser2=the typical number of messages sent in the app per day,
  personalMsgLengthAvgUser2=the average length of personal messages sent by the user,
  BeenThereReactionPerMsgUser2=the total number of Been-There reactions submitted by the user,
  topMutualJourneyMutualSteps=the total number of mutual steps the user shares with a matched user in the journey for which they were matched,
  PersonalMessageCountPerRoomUser2=typical number of messages the user wrote in chat rooms they were in,
  personalMessageCountPerDaysWritingMsgsUser2=the typical number of messages the user wrote on days the user wrote messages,
  PersonalQuestionsFromPersonalMsgsUser2=the total number of personal questions the user asked in response to personal messages,
  genderUser2=the gender of the user,
  CountryUser2=the country the user resides in,
  isSameCountry=whether a matched user resides in the same country as the user,
  BeenThereReactionsFromAllReactionsUser2=the portions of all the user's reactions which are of the type "Been-There",
  RelationshipAdviceStepsCountUser2=the total number of relationship advice steps the user has traversed,
  groupMsgCountPerDaysInAppUser2=the total number of group messages the user participated in per day the user was logged into the app, InsightfulReactionPerMsgUser2=the typical number of insightful reactions the user has for each user they are matched with, PersonalRoomsFromAllRoomsUser2=the number of personal rooms the user is in, HeartReactionsFromAllReactionsUser2=the proportion of the user's reactions which are heart reactions, allMsgLengthAvgUser2=the typical message length of messages written by the user, BodyPositiveSpetsCoutUser2=the total number of body positive steps the user has traversed, and IsSameGender=whether or not the user is the same gender as the user they are interacting with.

FIGS. 23A through 23C illustrate for a plurality of users the suitability of that user as a match versus the average number of threads the user replied to (FIG. 23A), the suitability of that user as a match versus the total number of threads the user started (FIG. 23B), and the goodness of that user as a match versus the average number of threads the user started (FIG. 23C). A chi-square analysis is performed for each dataset, and a fit representative of the suitability of match with increasing horizontal axis value is shown.

FIG. 24 illustrates data representing importance of users sharing a top journey when determining suitability of match. The platform can tally the total number of conversations, total number of worst conversations, total number of top conversations, and the percentage of conversations which were top conversations. In this method, a higher percentage of conversations which are top conversations is indicative that the journey for which the metric is calculated has a higher user matching success rate when both users share the journey as their top journey. The data indicates that the heartbreak journey may rely heavily on the users sharing the journey as a top journey for a good match, while the body positive journey may rely least heavily on the users sharing the journey as a top journey for a good match.

FIG. 25 illustrates the relationship between gender and conversation value. A comparison of male and female users with respect to which users tend to start more valuable conversations can be performed. In this example, the platform can tally the numbers and average lengths of such conversations, and noted who initiated each conversation. The platform can apply a chi square analysis, and determine that in this example, conversations initiated by a female and accepted by a male were twice as valuable than conversations initiated by a male and accepted by a female.

FIG. 26 shows the relationship between the completion of a biography and the closeness of conversation between the two users. Thus, the platform can assign each user B who was recommended as a match for one or more users A a score of 1 or 0, where 1 indicated that user B had completed the biography, and 0 indicated that user B had not completed the biography. Additionally, conversations that user B were involved in with one or more of users A were assigned a score of 1 or 0, where 1 indicated a good conversation and 0 indicated a bad conversation. These values were represented in a mosaic plot as shown here. The Y axis ranges from 0 to 1, and represents the fraction of the total number of conversations. The numbers inside each square indicate the percentage of conversations for a given user B score. The red boxes indicate bad conversations, and the red boxes indicate good conversations. For example, for users B with a biography completed, 53.9 percent of the conversations were good, based on the data set used.

FIG. 27 shows the relationship between country of residence of the recommended user in an app. A method as described herein can be used to recommend a user to another user, and the closeness of conversation between two users. The X axis indicates the country of origin for a plurality of users B, and includes the United Arab Emirates, Australia, Canada, Great Britain, Ireland, New Zealand, the United States, and other countries. The Y axis ranges from 0 to 1, and represents the fraction of the total number of conversations. The red boxes indicate bad conversations, and the red boxes indicate good conversations.

FIG. 28 illustrates how user certain metrics may be used to describe user value. Shown is an example of the values of a plurality of users (on a scale of 0 to 1) as a function of four metrics, where the four metrics are average number of total reactions the user indicated per message, the average number of heart reactions the user indicated per message, the average number of Been-There reactions the user indicated per message, and the total number of insightful reactions the user indicated per message. The data can be plotted, and a Chi Squared analysis can be applied, and a logistic fit can be fitted to the data and drawn onto the plots.

While preferred embodiments of the present invention have been shown and described herein, it will be obvious to those skilled in the art that such embodiments are provided byway of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for matching between two or more users of a plurality of users, the method comprising:

receiving input data from a plurality of devices associated with the plurality of users, wherein the input data comprises information related to one or more life events, wherein each life event comprises one or more different steps on a timeline;

analyzing the input data to determine, for each user and life event, which step(s) on the timeline each user (a) has experienced, (b) is currently experiencing, or (c) is to experience in the future; and matching the at least two users of the plurality of users, based on steps comprising at least one of: (a) matching a first user, who is to experience a selected step on the timeline in the future with a second user, who has already experienced the selected step; (b) matching a first user, who has already experienced a selected step on the timeline for a life event with a second user, who has also already experienced the selected step; and (c) matching a first user, who is to experience a selected step on the timeline for a life event with a second user, who is also to experience the selected step; wherein the at least one of steps (a)-(c) further comprises (d)

matching the second user with a first group of users who are to experience the selected step, and (e) matching the first user with a second group of users who have already experienced the selected step.

2. The method of claim 1, wherein receiving the input data comprises crowdsourcing the input data from the users.

3. The method of claim 1, wherein matching the two or more users comprises comparing the users to one another based on steps on individual timelines of each user.

4. The method of claim 1, further comprising at least one of: providing a recommendation to the first user to connect with the second user and obtain insights about the selected step from the second user; providing a recommendation to the second user to connect with the first user to share insights about the selected step with the first user; and providing a recommendation to the first and second users to connect with one another in relation to the selected step.

5. The method of claim 4, further comprising: providing an electronic interface for enabling the first and second users to connect with one another, wherein the electronic interface is adapted to execute an application, configured to allow the first and second users to share one or more data elements pertaining to a selected step on a timeline of a life experience with one another, and wherein shared one or more data elements are selected from a list consisting of: comments, insights or experiences about the selected step.

6. The method of claim 5, further comprising: monitoring at least one of a duration, a level and a frequency of communication between the first user and the second user.

7. The method of claim 5, wherein the application is configured to perform at least one of:
allow the first and second users to add additional comments, insights or experiences about the selected step or other steps on the timeline for the life event;
allow the first user to view the second user's experiences relating to the selected event, if the second user has already experienced the selected event;
allow the first and second users to view each other's experiences relating to the selected event, if both the first and second users have already experienced the selected event;
allow the first user to view the second user's timeline and steps, and/or the second user to view the first user's timeline and steps;
allow the first user to view changes to the second user's timeline as the second user undergoes the life event, or allow the second user to view changes to the first user's timeline as the first user undergoes the life event; and
allow the first and second user to view changes to each other's timeline as the first and second users respectively undergo the life event.

8. The method of claim 4, wherein the recommendation to the first user comprises a first suggested conversation starter to connect with the second user, and the recommendation to the second user comprises a second suggested conversation starter to connect with the first user.

9. The method of claim 8, wherein the first suggested conversation starter is personalized for the first user, and wherein the second suggested conversation starter is personalized for the second user.

10. The method of claim 1, further comprising: providing an electronic interface or platform configured to allow (1) the first user to connect with one or more users from the second group, and/or (2) the second user to connect with one or more users from the first group.

11. A computer-implemented method for matching between two or more users of a plurality of users, the method comprising:
receiving input data from a plurality of devices associated with the plurality of users, wherein the input data comprises information related to one or more life events, wherein each life event comprises one or more different steps on a timeline;
analyzing the input data to determine, for each user and life event, which step(s) on the timeline each user (a) has experienced, (b) is currently experiencing, or (c) is to experience in the future; and
matching the at least two users of the plurality of users, comprising, for each life event:
generating, for a first user, a plurality of scores relative to a second user, wherein the and second users are undergoing the same life event;
using the plurality of scores to determine a level of match of the second user to the first user; and
determining whether to provide a recommendation of the second user to the first user based on the level of match.

12. The method of claim 11, wherein the plurality of scores comprises a first score based on (i) a first set of steps experienced by the first user and (ii) a second set of steps experienced by the second user.

13. The method of claim 12, wherein the plurality of scores comprises a second score based on (i) a first set of steps experienced by the first user and (ii) a second set of steps that the second user is following and to experience.

14. The method of claim 13, wherein the plurality of scores comprises a third score based on (i) a first set of steps that the first user is following and to experience and (ii) a second set of steps that are experienced by the second user.

15. The method of claim 14, wherein the plurality of scores comprises a fourth score that is based on (i) first set of steps that the first user is following and to experience and (ii) a second set of steps that the second user is following and to experience.

16. The method of claim 15, wherein the first score is calculated based on a percentage of (a) a number of common steps between the first and second sets of steps over (b) a number of steps in the first set for the first user, and wherein the second score is calculated based on a percentage of (a) a number of common steps between the first and second sets of steps over (b) a number of steps in the first set for the first user, and wherein the third score is calculated based on a percentage of (a) a number of common steps between the first and second sets of steps over (b) a number of steps in the first set for the first user, and wherein the fourth score is calculated based on a percentage of (a) a number of common steps between the first and second sets of steps over (b) a number of steps in the first set for the first user.

17. A computer-implemented system for matching between a plurality of users, comprising:
a server in communication with a plurality of devices associated with the plurality of users; and
a non-transitory computer-readable memory associated with the server, wherein computer-readable instructions are stored, that, when executed by the server, cause the server to perform operations comprising:
receiving input data from the plurality of devices, wherein the input data comprises queries, comments or insights from different users relating to the one or more life events, wherein each life event comprises a plurality of different steps on a timeline;
analyzing the input data to determine, for each user and life event, which steps on the timeline that each user (a) has experienced, (b) is currently experiencing, or (c) to experience in the future; and matching the plurality of users with one another, based on comprising at least one of: (a) matching a first user, who is to experience a selected step on the timeline in the future with a second user, who has already experienced the selected step; (b) matching a first user, who has already experienced a selected step on the timeline for a life event with a second user, who has also already experienced the selected step; and (c) matching a first user, who is to experience a selected step on the timeline for a life event with a second user, who is also to experience the selected step; wherein the at least one of steps (a)-(c) further comprises (d) matching the second user with a first group of users who are to experience the selected step, and (e) matching the first user with a second group of users who have already experienced the selected step.

* * * * *